(12) United States Patent
Robles Toth et al.

(10) Patent No.: US 11,857,170 B2
(45) Date of Patent: Jan. 2, 2024

(54) METHODS AND DEVICES FOR REPAIRING CARTILAGE DEFECTS

(71) Applicant: Vericel Corporation, Cambridge, MA (US)

(72) Inventors: Felix Ernesto Robles Toth, Duxbury, MA (US); Robert Bruce Mackinnon, III, Carver, MA (US); Lester H. Fehr, Hampton, NH (US)

(73) Assignee: Vericel Corporation, Cambridge, MA (US)

( * ) Notice: Subject to any disclaimer, the term of this patent is extended or adjusted under 35 U.S.C. 154(b) by 0 days.

(21) Appl. No.: 18/117,245

(22) Filed: Mar. 3, 2023

(65) Prior Publication Data

US 2023/0277163 A1 Sep. 7, 2023

Related U.S. Application Data

(60) Provisional application No. 63/316,920, filed on Mar. 4, 2022.

(51) Int. Cl.
  *A61B 10/02* (2006.01)
  *A61B 17/34* (2006.01)
(52) U.S. Cl.
  CPC .......... *A61B 10/02* (2013.01); *A61B 17/3468* (2013.01)
(58) Field of Classification Search
  CPC combination set(s) only.
  See application file for complete search history.

(56) References Cited

U.S. PATENT DOCUMENTS

| 6,547,719 | B1 | 4/2003 | Atala et al. |
| 8,241,298 | B2 | 8/2012 | Sengun et al. |
| 11,246,577 | B2 * | 2/2022 | Gombrich .......... A61B 10/0291 |
| 2003/0012805 | A1 | 1/2003 | Chen |
| 2003/0211604 | A1 | 11/2003 | E. Brown |
| 2008/0268053 | A1 | 10/2008 | Geistlich et al. |
| 2009/0016997 | A1 | 1/2009 | Hathaway et al. |

(Continued)

FOREIGN PATENT DOCUMENTS

| WO | WO-2005/079881 A1 | 9/2005 |
| WO | WO-2006/008748 A2 | 1/2006 |

(Continued)

OTHER PUBLICATIONS

Abe, S. et al., Alloreactivity and immunosuppressive properties of articular chondrocytes from osteoarthritic cartilage, J Orthop Surg (Hong Kong), 24(2):232-9 (2016).

(Continued)

*Primary Examiner* — Sameh R Boles
(74) *Attorney, Agent, or Firm* — Choate, Hall & Stewart LLP; Peter A. Flynn; Qing Hua Wang

(57) ABSTRACT

The present disclosures describe devices and methods to repair cartilage defects using arthroscopic surgical methods. The disclosed devices include a cannula assembly including a cannula body, a dam seal sub-assembly disposed proximally from the cannula body, and an obturator inserted coaxially through both the cannula body and the dam seal sub-assembly; an articulated arthroscopic cutting tool; a ring curette; a square curette; a rake curette; a matrix shuttle delivery device for delivering a cell-seeded support matrix including chondrocytes; and an applicator tool.

16 Claims, 46 Drawing Sheets

(56) References Cited

U.S. PATENT DOCUMENTS

| | | |
|---|---|---|
| 2009/0186062 A1 | 7/2009 | Spector et al. |
| 2011/0274729 A1 | 11/2011 | Collins |
| 2012/0230966 A1 | 9/2012 | Crawford et al. |
| 2013/0226314 A1 | 8/2013 | Li et al. |
| 2014/0163695 A1 | 6/2014 | Orr et al. |
| 2015/0025311 A1 | 1/2015 | Kadan et al. |
| 2017/0100434 A1 | 4/2017 | Majumdar |
| 2019/0015209 A1 | 1/2019 | Seifert et al. |
| 2020/0022815 A1 | 1/2020 | Sengun et al. |

FOREIGN PATENT DOCUMENTS

| | | |
|---|---|---|
| WO | WO-2012/158952 A1 | 11/2012 |
| WO | WO-2019/113558 A1 | 6/2019 |
| WO | WO-2023/022941 A1 | 2/2023 |
| WO | WO-2023/168080 A1 | 9/2023 |

OTHER PUBLICATIONS

Adkisson, H.D. 4th et al., The potential of human allogeneic juvenile chondrocytes for restoration of articular cartilage, Am J Sports Med, 38(7):1324-33 (2010).

Alsalameh, S. et. al., Antigenicity and accessory cell function of human articular chondrocytes, J Rheumatol, 18(3):414-21 (1991).

Biant, L. C. et al., Cell Viability in Arthroscopic Versus Open Autologous Chondrocyte Implantation, Am J Sports Med, 45(1):77-81 (2017).

Brittberg, M. Autologous chondrocyte transplantation, Clinical Orthop, 367S:S147-S155 (1999).

Brittberg, M. et al., Matrix-Applied Characterized Autologous Cultured Chondrocytes Versus Microfracture: Five-Year Follow-up of a Prospective Randomized Trial, Am J Sports Med, 46(6):1343-1351 (2018).

Cheuk, Y. C. et al., Use of allogeneic scaffold-free chondrocyte pellet in repair of osteochondral defect in a rabbit model, J Orthop Res, 29(9):1343-50 (2011).

Frisbie, DD et. al,, A comparative study of articular cartilage thickness in the stifle of animal species used in human pre-clinical studies compared to articular cartilage thickness in the human knee, Vet Comp Orthop Traumatol, 19(3):142-6 (2006).

Hendrich, C. et al., Cartilage Surgery and Future Perspectives, Springer-Verlag Berlin Heidelberg 2003, 204 pages, https://doi.org/10.1007/978-3-642-19008-7.

Huey, D. J. et al., Immunogenicity of bovine and leporine articular chondrocytes and meniscus cells, Tissue Eng Part A, 18(5-6):568-75 (2012).

Hyc, A. et. al., Immunological response against allogeneic chondrocytes transplanted into joint surface defects in rats, Cell Transplant, 6(2): 119-24 (1997).

International Search Report for PCT/US2022/040207, 5 pages (dated Jan. 5, 2023).

International Search Report for PCT/US2018/64629 (Compositions and Methods for Repairing Cartilage Defects, filed Dec. 7, 2018), issued by ISA/US, 3 pages (dated Mar. 21, 2019).

Jones, K. J. and Cash, B. M., Matrix-Induced Autologous Chondrocyte Implantation With Autologous Bone Grafting for Osteochondral Lesions of the Femoral Trochlea, Arthrosc Tech., 8(3):e259-e266 (2019).

Lohan, P. et al., Culture expanded primary chondrocytes have potent immunomodulatory properties and do not induce an allogeneic immune response, Osteoarthritis Cartilage, 24(3):521-33 (2016).

Muinos-Lopez, E. et al., Cryopreservation Effect on Proliferative and Chondrogenic Potential of Human Chondrocytes Isolated from Superficial and Deep Cartilage, The Open Orthopaedics Journal, 6:150-159 (2012).

Nixon, A.J. et al., A chondrocyte infiltrated collagen type I/III membrane (MACI implant) improves cartilage healing in the equine patellofemoral joint model, Osteoarthritis and Cartilage, 23:648-660 (2015).

Pereira, R. C. et al., Human articular chondrocytes regulate immune response by affecting directly T-cell proliferation and indirectly inhibiting monocyte differentiation to professional antigen-presenting cells, Front Immunol, 24(7):415 (2016).

Shangkai, C. et al., Transplantation of allogeneic chondrocytes cultured in fibroin sponge and stirring chamber to promote cartilage regeneration. Tissue Eng, 13(3):483-92 (2007).

Standard guide for in vivo assessment of implantable devices intended to repair or regenerate articular cartilage (https://www.astm.org/Standards/F2451.htm).

Warwick, R. et al., Report of the 17th International Congress of the European Association of Tissue Banks (EATB) held jointly with the 17th Annual Congress of the British Association for Tissue Banking (BATB) including EATB/BATB/American Association of Tissue Banks (AATB) Cardiovascular Symposium, Cell Tissue Bank, 11:107-154 (2010).

Weinand, C. et al., Healing potential of transplanted allogeneic chondrocyte of three different sources in lesions of avascular zone of the meniscus: a pilot study, Arch Orthop Trauma Surg, 126(9):599-605 (2006).

Written Opinion for PCT/2022/040207, 9 pages (dated Jan. 5, 2023).

Written Opinion for PCT/US2018/64629 (Compositions and Methods for Repairing Cartilage Defects, filed Dec. 7, 2018), issued by ISA/US, 17 pages (dated Mar. 21, 2019).

International Search Report for PCT/US2023/014503, 6 pages (dated Jul. 11, 2023).

Written Opinion for PCT/2023/014503, 9 pages (dated Jul. 11, 2023).

* cited by examiner

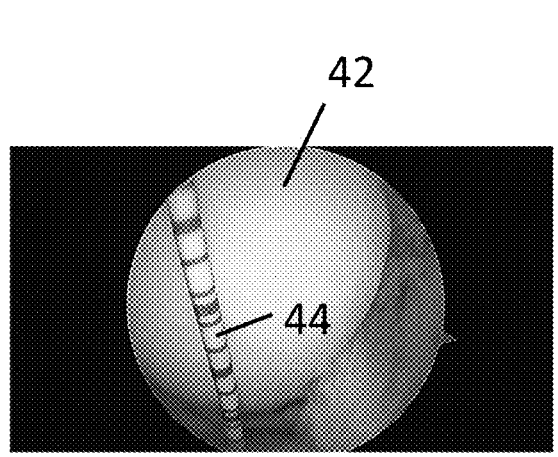
FIG. 2A
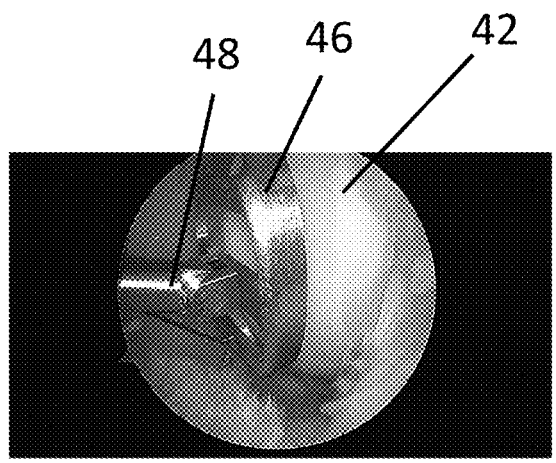
FIG. 2B
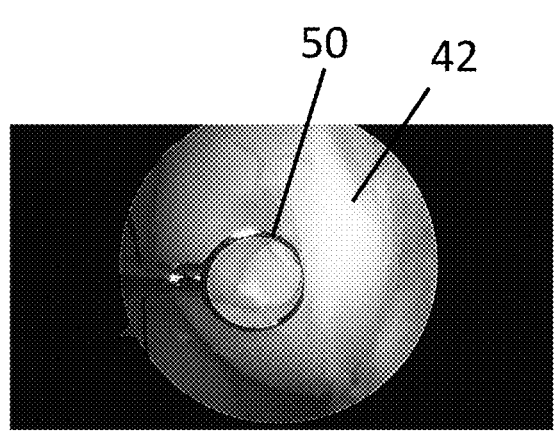
FIG. 2C
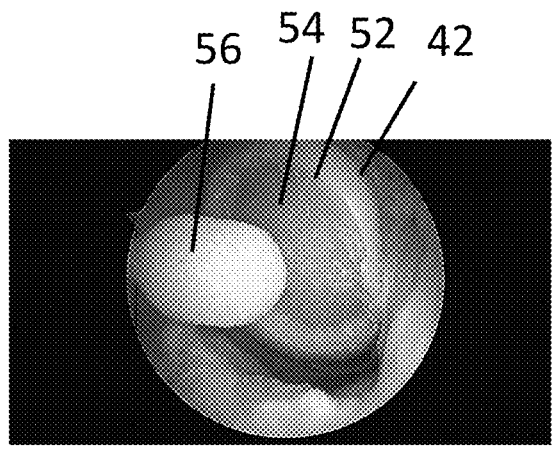
FIG. 2D
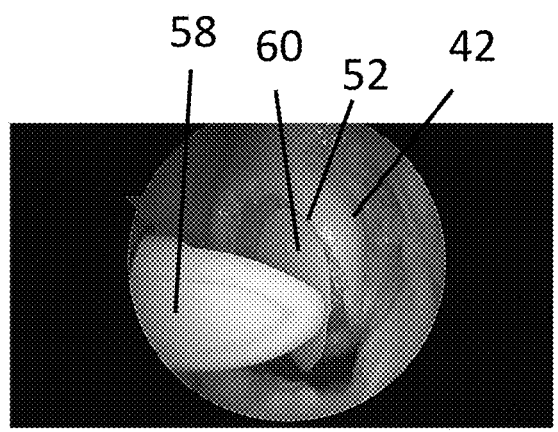
FIG. 2E
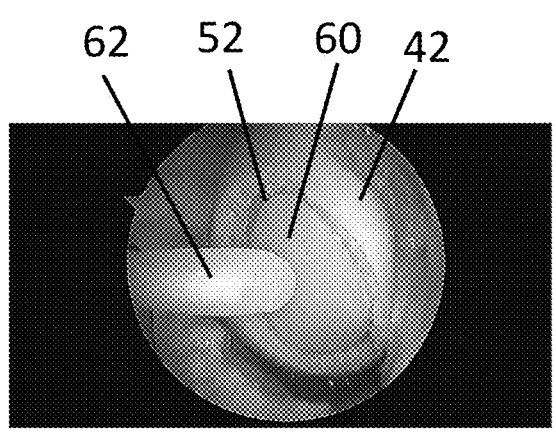
FIG. 2F
FIG. 2

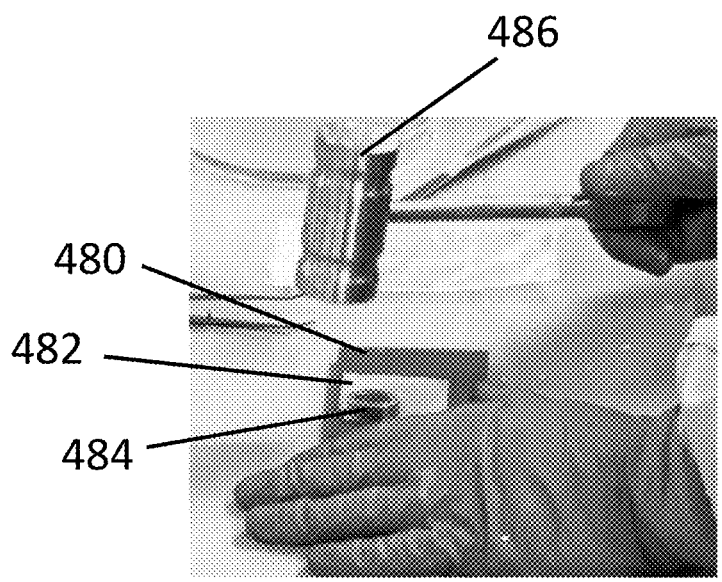
FIG. 41A
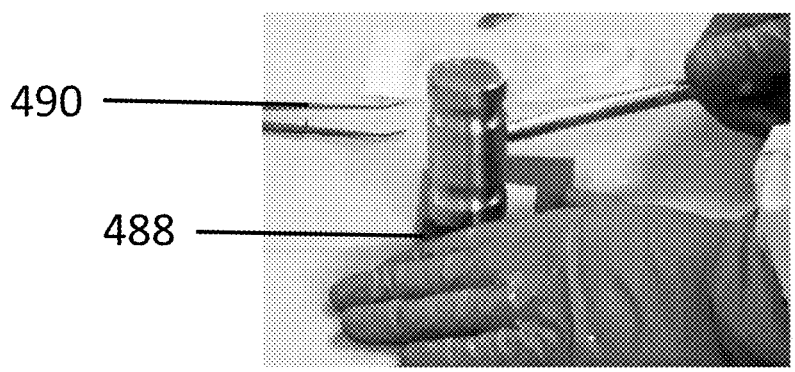
FIG. 41B
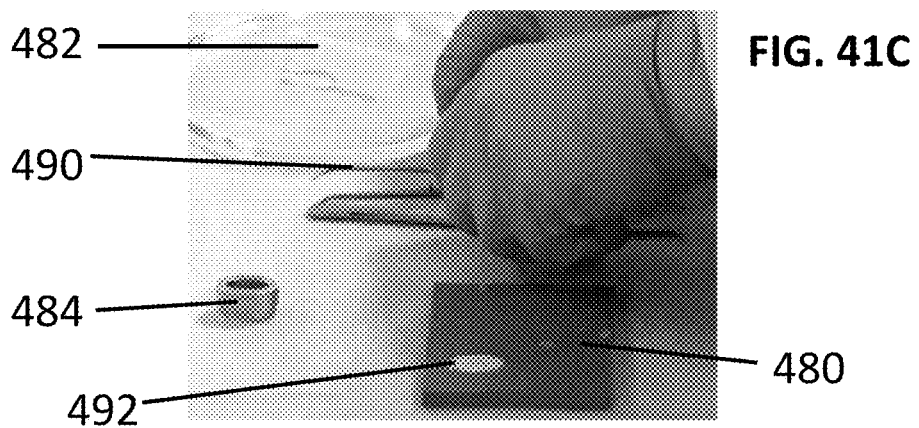
FIG. 41C
FIG. 41

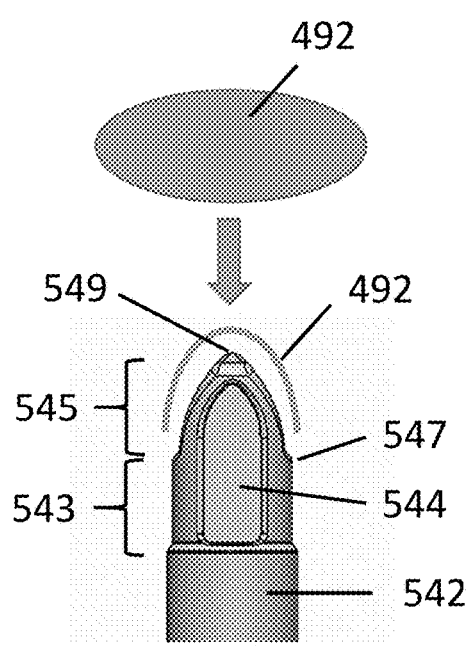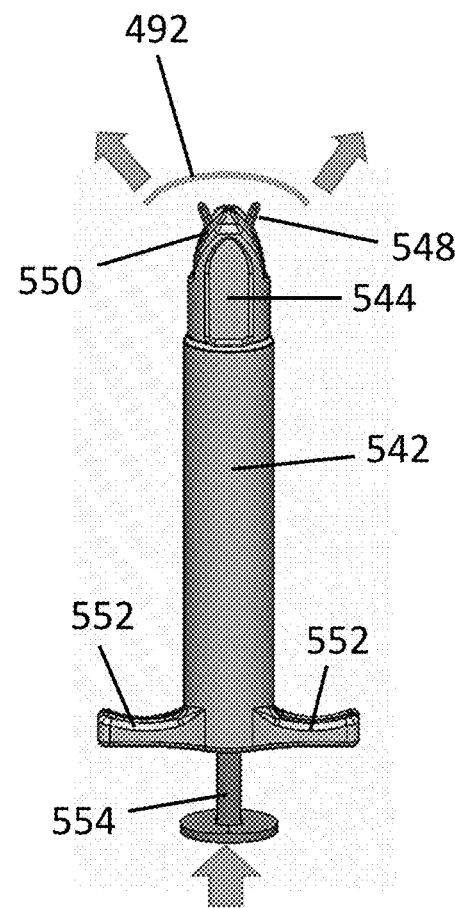
FIG. 47
FIG. 48

METHODS AND DEVICES FOR REPAIRING CARTILAGE DEFECTS

CROSS-REFERENCE TO RELATED APPLICATIONS

This application claims priority to U.S. Provisional Application No. 63/316,920, filed Mar. 4, 2022, entitled "Methods and Devices for Repairing Cartilage Defects", the contents of which is incorporated herein by reference in its entirety.

BACKGROUND

Chondral and osteochondral lesions such as focal lesions in the load-bearing region of a knee's articular cartilage can greatly increase the risk for osteoarthritis. This type of lesion occurs frequently from, for example, trauma, participation in sports, osteochondritis dissecans, etc. The capacity for spontaneous repair of chondral lesions is minimal, due in part to the limited blood supply to cartilage tissue. Treatment of damaged cartilage requires replacement of defective cartilage with healthy cartilage; autologous chondrocyte implantation strategies have been described to accomplish such replacement (Brittberg et al. *Clin. Orthopaed. Red. Res.* (1999) 367S: S147-S155). In such procedures, chondrocytes are harvested from a patient, expanded in cell culture to increase the number of chondrocytes, and then implanted back into the injury site of the patient.

More recent work has improved autologous implantation by seeding expanded autologous cells on a matrix in a process known as matrix-induced autologous chondrocyte implantation (MACI) (Basad et al. In: Hendrich et al., *Cartilage Surgery and Future Perspectives*, Thieme Verlag, 49-56 (2003)). The MACI process has been further improved to allow for the implantation of allogeneic cells, reducing the total number of necessary procedures undergone by a patient. However, the MACI procedure has typically been performed via mini-arthrotomy, an open surgical technique that generally presents a greater risk of infection, longer recovery times, and increased pain for patients when compared to less invasive surgical methods. Moreover, many patients present with defects that are amenable to treatment via minimally invasive procedures.

SUMMARY

The present disclosure provides improved matrix-induced autologous chondrocyte implantation (MACI) technologies. For example, among other things, the present disclosure provides technologies for the arthroscopic delivery of MACI implants; in some embodiments, provided technologies are characterized in that they achieve delivery characterized by levels of cell viability comparable to those observed with non-arthroscopic delivery. Advantages of the provided methods include, for example, arthroscopic delivery that is far less invasive than open surgical strategies, which have typically been used to administer MACI implants. Provided technologies, thus, represent and embody further improvements with respect to arthroscopic MACI technologies (tools, methods, and kits) for the treatment of tissue defects (for example, cartilage defects, among other types of defects).

In some embodiments, the present disclosure provides technologies for arthroscopically delivering a composition comprising cells seeded on a surface of a matrix to a site in an articulating joint.

In some embodiments, the present disclosure provides technologies for treating a chondral defect and/or osteochondral defect. The method may include implanting a composition including cells seeded on a matrix.

In some embodiments, the present disclosure provides arthroscopic delivery technologies and methods. In general, the present disclosure provides a set of tools and methods that enable arthroscopic delivery of a cell-seeded implant at a prepared cartilage surgical site for effective repair of cartilage and tissue defects in a less invasive manner than conventional open surgical techniques while maintaining cell viability.

In some embodiments, the present disclosure provides technologies for arthroscopically preparing a cartilage defect or lesion. The technologies may include one or more surgically sharp cutting tools to define a surgical area in the cartilage and to scrape, cut, debride, and/or remove cartilage.

In some embodiments, a composition which includes cells seeded on a matrix (or cell-seeded support matrix) is loaded into the distal end of a surgical shuttle delivery device prior to inserting the surgical shuttle delivery device into a cannula positioned in a surgical site. The composition may then be deposited from the surgical shuttle delivery device and into the surgical area previously prepared by the surgically sharp cutting tools.

In some embodiments, cells are a monolayer on a membrane.

In some embodiments, the cell-seeded support matrix is cut to a shape and size that closely matches the shape and size of the surgical area prepared by the surgically sharp cutting tools. The present disclosure provides methods of cutting the cell-seeded support matrix using a matrix cutting tool. In some embodiments, the matrix cutting tool may have a defined shape (e.g., oval, circle, square, rectangle, etc.) and a surgically sharp blade along a bottom circumference. The matrix cutting tool may be placed blade-side down onto a portion of a cell-seeded support matrix and pressed down with some force exerted by hand or by a tool (e.g., a hammer, a mallet, etc.) to cut into the cell-seeded support matrix. In some embodiments, the portion of cell-seeded support matrix that has been cut may be manipulated (e.g., picked up, positioned, placed, etc.) using tools (e.g., tweezers, graspers, probes, etc.) or by hand.

In some embodiments, the present disclosure provides methods of arthroscopically delivering a composition comprising cells seeded on a surface of a matrix (or cell-seeded support matrix) to a defect, the defect including a knee defect such as a femoral defect, a trochlear defect, patellar defect, and/or a tibial defect in a subject. In some embodiments, the defect may include an ankle defect and/or a shoulder defect. The defect may have a surface area of up to about 4 cm². In some embodiments, the methods include steps that are performed in a time period that extends from surgical opening to surgical closing, with the time period not exceeding about 60 minutes. In some embodiments, a defect includes a cartilage defect. In some embodiments, cells include chondrocytes. In some embodiments, cells are autologous to the subject. In some embodiments, cells include allogeneic cells.

In some embodiments, a surgical instrument system includes a cannula assembly, a composition including cells seeded on a surface of a matrix (or cell-seeded support matrix), and one or more cutting tools for cutting and shaping a composition. The kit may also include one or more of the following tools constructed to pass through the cannula to perform tasks arthroscopically: an arthroscopic measurement tool, an articulated cutting tool, a ring curette, a square curette, a rake curette, an applicator tool, and a matrix shuttle delivery device for transporting and depositing the composition at the surgical site. In some embodiments, the user or operator or surgeon may employ other surgical tools and materials during an arthroscopic surgical procedure that may include hemostatic barriers, covering patches, organic glues, scissors, razor blades, scalpels, surgical mallets, tweezers, needles, etc.

In some embodiments, the cannula assembly may include an obturator, a dam seal sub-assembly, and a cannula body. The dam seal sub-assembly may be released from the cannula body via clips or tabs. Flexible dam seals within the dam seal sub-assembly may allow surgical tools to be inserted into the cannula while retaining fluid at the surgical site or in the patient's joint region. The cannula body may be threaded along its exterior surface to improve its stability when installed at a surgical site.

In some embodiments, the arthroscopic measurement tool may include a handle, a shaft, flexible ruler, and/or an adjustment knob. The flexible ruler is etched or marked with millimeter-scale markings and is connected to the adjustment knob such that sliding the knob longitudinally along the handle causes the ruler to be extended or retracted, and rotating the knob causes the ruler to be rotated to different orientations or angles. The ruler may be used to measure dimensions of cartilage defects.

In some embodiments, the articulated arthroscopic cutting tool may include a handle, a thumb slider, a shaft, and/or a curved oval blade with a surgically sharp cutting edge. Sliding the thumb slider causes the blade to tilt to different angles with respect to the longitudinal axis of the handle and shaft. The blade may be pushed or impacted by a surgical mallet into cartilage surrounding a cartilage defect to score the cartilage. The scoring of the cartilage forms a clear outline to delineate a region where cartilage should be removed in preparation for implanting of a cell-seeded support matrix. In some embodiments, the curved oval blade made include various sizes in order to surround different sizes of cartilage defects. The articulated arthroscopic cutting tool may also be called an arthroscopic cutter.

In some embodiments, the ring curette may include a handle, a shaft, and/or a circularly-shaped ring with a surgically sharp cutting edge.

In some embodiments, the square curette may include a handle, a shaft, and/or a square-shaped ring with at least two surgically sharp cutting edges.

In some embodiments, the rake curette may include a handle, a shaft, and/or wedge-shaped blade with a surgically sharp cutting edge.

In some embodiments, the matrix cutter may include an elliptic cylindrical body and/or a surgically sharp edge around its bottom circumference. In some embodiments, the matrix cutter may include various sizes to match the sizes of the curved oval blades in the articulated arthroscopic cutting tool. The matrix cutter is used to cut portions of cell-seeded support matrix into shapes that match the cartilage defect site prepared by the cutting tools with minimal contact or damage to the cells.

In some embodiments, the matrix shuttle delivery device may include a cylindrical body with finger grips and a tapered delivery tip, a plunger, and deployment wings. A portion of cell-seeded support matrix is placed onto the matrix shuttle delivery device, which may then be inserted into a cannula at a surgical site or joint. Pushing the plungers causes deployment wings to protrude at the delivery tip to push the cell-seeded support matrix off the matrix shuttle delivery device and onto the defect site.

In some embodiments, the applicator tool may include a cylindrical rod, an applicator swab at one end of the rod, and/or an applicator tip at the other end of the rod. The applicator swab may comprise one or more soft, absorbent materials including polyurethane foam and cotton, and may be used to clean and dry a defect site. The applicator tip may comprise silicone or other similarly elastic polymeric material. The applicator tip may be used to reposition a cell-seeded support matrix and to apply fibrin glue.

In one aspect, the present embodiments are directed to a cannula assembly includes: a cannula body; a dam seal sub-assembly disposed proximally from the cannula body, the dam seal sub-assembly and the cannula body coaxially aligned (or longitudinally aligned, or axially aligned); and an obturator inserted coaxially through both the cannula body and the dam seal sub-assembly.

In some embodiments, the cannula body includes: a hollow cylindrical portion comprising a helical thread wrapping around an entire length of an exterior surface of the hollow cylindrical portion; a lip portion at the proximal end of the hollow cylinder portion, the lip portion including a diameter greater than that of the hollow cylindrical portion; two tabs disposed at diametrically opposite positions on an outer edge of the lip portion; and a curved opening at the distal end of the hollow cylindrical portion.

In some embodiments, the curved opening is marked by a visible outline around a circumference of the curved opening, and by two small visible marks at diametrically opposite positions around the curved opening.

In some embodiments, the cannula body includes a translucent polycarbonate material.

In some embodiments, the dam seal sub-assembly includes: a dam top piece; a first dam seal comprising at least one hole; a second dam seal comprising at least one slit; a third dam seal comprising at least one slit; and a dam bottom piece. In some embodiments, the dam top piece, the first dam seal, the second dam seal, and the third dam seal are all coaxially aligned (or longitudinally aligned, or axially aligned) and stacked parallel with each other.

In some embodiments, the dam top piece includes: a circular portion comprising a circular hole disposed concentrically within it; multiple legs extending perpendicularly from the bottom surface of the circular portion and distributed circumferentially around the circular portion; and two notches disposed at diametrically opposite positions about the circular hole.

In some embodiments, the dam top piece and dam bottom piece include acrylonitrile butadiene styrene (ABS).

In some embodiments, the first dam seal includes: a circular disc; a circular hole disposed concentrically in the center of the circular disc; and multiple smaller circular holes disposed circumferentially around the edge of the disc.

In some embodiments, the second and third dam seals each include: a circular disc; three slits from the center of the circular disc along the radial direction, separated by 120 degrees from each other; and multiple smaller circular holes disposed circumferentially around the edge of the circular disc. In some embodiments, the second and third dam seals are stacked on top of each other coaxially and rotated such that the slits in each seal do not overlap.

In some embodiments, the first dam seal, the second dam seal, and the third dam seal all include one of silicone or EPDM rubber.

In some embodiments, the dam bottom piece includes: a hollow cylinder portion; a flat circular top portion; a circular hole disposed concentrically in the flat circular top portion; two indentations disposed at diametrically opposite locations around the circular hole; and two dam release clips disposed at diametrically opposite locations at the distal edge of the hollow cylinder portion.

In some embodiments, the dam top piece and dam bottom piece include acrylonitrile butadiene styrene (ABS) or equivalent.

In some embodiments, the obturator includes: a handle portion at the proximal end of the obturator; a shaft portion; and a tip portion at the distal end of the obturator. In some embodiments, the handle portion includes a rounded domed structure comprising slats of constant thickness disposed parallel and perpendicular to the axis direction, the shaft portion includes a cylindrical rod linking the handle portion and the tip portion, the tip portion includes a conical tip at the distal end and multiple support fins, and the handle portion, the shaft portion, and the tip portion are all coaxially aligned (or longitudinally aligned, or axially aligned).

In some embodiments, the obturator includes: two or more rotation tabs protruding from the bottom of the distal side of the handle portion disposed at diametrically opposite locations; and one or more concave portions in the domed structure of the handle portion.

In some embodiments, the obturator includes acrylonitrile butadiene styrene (ABS) or equivalent.

In another aspect, the present embodiments are directed to an arthroscopic surgical method including: making an incision at a joint on a patient's body; inserting a cannula assembly into the incision; measuring a cartilage defect at the joint using an arthroscopic measurement tool inserted through the cannula; preparing a cartilage area around the cartilage defect; and preparing and cutting a portion of cell-seeded matrix composition using an matrix cutter tool.

In some embodiments, preparing a cartilage area further includes: scoring an area in the cartilage around the defect using a cutter tool; debriding the scored area of using one or more cutting and scraping tools to expose a bone surface in a defined area or shape; and drying the exposed bone area using an applicator tool.

In some embodiments, the joint site may include one of medial femoral condyle, a lateral femoral condyle, a patella, or a trochlea.

In some embodiments, debriding the scored area further includes using at least one of a ring curette, a square curette, or a rake curette.

In another aspect, the present embodiments are directed to a method for determining the size of a lesion during arthroscopic surgery, including: inserting a measuring tool into a cannula through a dam seal sub-assembly; extending a ruler from the measuring tool; measuring at least one dimension of at least one lesion using at least one or more markings on the ruler; retracting the ruler into the measuring tool; and removing the measuring tool from the cannula and the dam seal sub-assembly.

In another aspect, the present embodiments are directed to an arthroscopic measurement probe, including: a handle including a top shell piece and a bottom shell piece; an adjusting knob; a rotating plug; a dowel pin; a stroke arm; a sizer tube; and a flexible ruler. In some embodiments, the rotating plug, the adjusting knob, the stroke arm, the sizer tube, and the flexible ruler are connected coaxially, and the flexible ruler is disposed through the interior of the sizer tube.

In some embodiments, the flexible ruler includes: a cylindrical rod including polyether ether ketone (PEEK); an interior flexible wire comprising nickel titanium (or Nitinol); and multiple markings distributed along a length of an exterior surface of the cylindrical rod near the distal end of the cylindrical rod. In some embodiments, the markings include thin lines perpendicular to the longitudinal axis of the cylindrical rod and are separated by spacings of 2.5 mm and 5.0 mm.

In some embodiments, the sizer tube includes: a hollow cylindrical tube including at least one of stainless steel T304, stainless steel T316, and fractional hypodermic tubing; two slits disposed at the proximal end of the hollow cylindrical tube and positioned at diametrically opposite locations; a curved portion of the hollow cylindrical tube at the distal end. In some embodiments, the curve includes a right angle bend in the tube and an opening in the distal end of the hollow cylindrical tube.

In some embodiments, the top shell piece and the bottom shell piece comprise acrylonitrile butadiene styrene (ABS) or other similar plastic.

In another aspect, the present embodiments are directed to a method for scoring cartilage using articulated arthroscopic cutting tool, including: choosing an articulated arthroscopic cutting tool based on measured dimensions of a defect or lesion; removing a dam seal sub-assembly from a cannula; inserting an articulated arthroscopic cutting tool into the cannula; adjusting a tilt angle of a blade using a thumb slider; locking the tilt angle; pressing the blade into a cartilage area surrounding a defect; and removing the articulated arthroscopic cutting tool from the cannula.

In another aspect, the present embodiments are directed to an articulated arthroscopic cutting tool including: a handle; a thumb slider; a linear stator shaft; a curved oval blade connected by a hinged joint to the linear stator shaft; a linear transmission shaft connected to the thumb slider; and a linkage piece connected to both the linear transmission shaft and the curved oval blade. In some embodiments, movement of the thumb slider causes the curved oval blade to tilt with respect to the linear stator shaft.

In some embodiments, the handle includes: an upper shell including a ridged half-cylinder and a rectangular opening cut longitudinally along the ridged half-cylinder closer to the distal end of the ridged half-cylinder; and a lower shell including a ridged half-cylinder. In some embodiments, the upper shell and lower shell are closed together to form a full cylinder with a circular opening at the distal end, and a plurality of notches are disposed on the underside of the upper shell around the rectangular opening.

In some embodiments, the upper shell and the lower shell include acrylonitrile butadiene styrene (ABS) or equivalent plastic.

In some embodiments, the thumb slider includes: a slider button comprising a raised top surface at the distal end of the button and a ridged top surface at the proximal end of the button; a slider clamp piece; and a spring attached to the slider button at one end of the spring and attached to the slider clamp piece at another end of the spring, and with the spring disposed perpendicularly between the slider button and the slider clamp piece. In some embodiments, a cylindrical pin actuated by the slider button may interface with the plurality of notches on the underside of the upper shell.

In some embodiments, the linear stator shaft includes: a cylindrical rod; a rectangular groove cut longitudinally along the cylindrical rod; a portion of reduced diameter along the cylindrical rod near the proximal end of the cylindrical rod; and a circular ring protruding perpendicularly from the distal end of the cylindrical rod.

In some embodiments, the linear stator shaft includes stainless steel type 17-4PH (630), UNS S17400, per ASTM A564.

In some embodiments, the curved oval blade includes: an oval ring; at least three crossbar pieces spanning across a top surface of the oval ring; a circular ring extending perpendicularly from the first crossbar piece; two circular rings extending perpendicularly from the second crossbar piece; and a curved cutting surface along a bottom circumference of the oval ring, wherein the oval ring is thicker at narrow ends of the oval ring, and wherein the curved cutting surface comprises a surgically sharp edge.

In some embodiments, the curved oval blade comprises stainless steel type 17-4PH (630), UNS S17400, per ASTM A564.

In another aspect, the present embodiments are directed to a method for removing cartilage and preparing surgical site, including: inserting a surgical cutting tool selected from at least one of a ring curette, a square curette, or a rake into a cannula and dam seal sub-assembly; scraping, cutting, debriding and removing cartilage using the surgical cutting tool within a region of cartilage defined by an articular arthroscopic cutting tool; removing the cutting tool from the cannula and dam seal sub-assembly; and repeating the procedure with one or more surgical cutting tools until the cartilage within the region of cartilage is completely removed.

In another aspect, the present embodiments are directed to a ring curette assembly including: a handle; a shaft coupled to the distal end of the handle; and a ring curette blade coupled to the distal end of the shaft, wherein the shaft comprises a cylindrical rod with at least two bends such that the distal end of the shaft has an axis that is parallel to and eccentric from a primary longitudinal axis of the shaft, and wherein the ring curette blade comprises at least one surgically sharp edge.

In some embodiments, the shaft includes: a cylindrical rod; a flat portion at the proximal end of the cylindrical rod for attachment within the handle; a first bend in the cylindrical rod near the distal end of the rod such that the rod axis is angled away from a primary longitudinal axis of the cylindrical rod; a second bend in the cylindrical rod further toward the distal end of the rod such that the rod axis is angled parallel to and positioned eccentrically from the primary longitudinal axis of the cylindrical rod; a cylindrical portion with reduced diameter near the distal end of the rod; and a recessed opening at the distal end of the shaft with flat interior surfaces.

In some embodiments, the ring curette blade includes: a ring in the shape of a hollow right circular conical frustum; a rounded edge around the larger circumference of the ring; a surgically sharp edge around the larger circumference of the ring; a cylindrical connection shaft disposed pointing radially out at an outer wall of the ring; and a cylindrical welding shaft disposed coaxially with the connection shaft. In some embodiments, the cylindrical welding shaft has a smaller diameter than the cylindrical connection shaft.

In some embodiments, the shaft and the ring curette blade include stainless steel type 17-4PH (630) or equivalent, and/or UNS S17400, per ASTM A564.

In some embodiments, the handle includes: a cylindrical body; a plurality of ridges on exterior lateral and bottom surfaces of the cylindrical body arranged perpendicular to the longitudinal axis of the cylindrical body; a flat surface along a top surface of the cylindrical body; and a circular opening in the distal end of the cylindrical body.

In some embodiments, the handle includes acrylonitrile butadiene styrene (ABS) or equivalent.

In another aspect, the present embodiments are directed to a square curette assembly including: a handle; a shaft coupled to the distal end of the handle; and a square curette blade coupled to the distal end of the shaft. In some embodiments, the shaft includes a cylindrical rod with at least two bends such that the distal end of the shaft has an axis that is parallel to and eccentric from a primary longitudinal axis of the shaft, and the square curette blade includes at least two surgically sharp edges at the distal end of the square curette blade.

In some embodiments, the square curette blade includes: a ring in the shape of a hollow, rounded, rectangular prism; at least two surgically sharp edges at a top and a bottom edge of the ring at the distal side of the rectangular prism; a cylindrical connection shaft disposed pointing outward at an outer wall of the ring and opposite the two surgically sharp edges; and a cylindrical welding shaft disposed coaxially with the connection shaft. In some embodiments, the cylindrical welding shaft has a smaller diameter than the connection shaft.

In some embodiments, the shaft and the square curette blade include stainless steel type 17-4PH (630) or equivalent, or UNS S17400, per ASTM A564.

In another aspect, the present embodiments are directed to a rake curette assembly including: a handle; a rake shaft coupled to the distal end of the handle; and a rake head blade coupled to the distal end of the shaft. In some embodiments, the rake shaft includes a cylindrical rod that tapers to a smaller diameter near the distal end of the shaft, and the rake head blade includes a tapered wedge with at least one surgically sharp edge.

In some embodiments, rake shaft includes: a cylindrical rod; a flat portion at the proximal end of the shaft for attachment within the handle; a tapered portion. In some embodiments, the diameter of the cylindrical rod decreases gradually toward the distal end of the rake shaft, and the rake further includes a cylindrical welding shaft disposed coaxially with the tapered portion of the rake shaft, with a further reduced diameter.

In some embodiments, the rake head blade includes: a wedge-shaped body that decreases in thickness while increasing in depth; a rounded top portion with a cylindrical opening for welding; and a surgically sharp edge at the end of the wedge-shaped body.

In some embodiments, the shaft and the rake head blade include stainless steel type 17-4PH (630) or equivalent, or UNS S17400, per ASTM A564.

In another aspect, the present embodiments are directed to a method for cutting a cell-seeded support matrix including: selecting a matrix cutter size to match a surgical site prepared by cutting and clearing away cartilage surrounding a defect or lesion; placing a cell-seeded support matrix on a cutting mat, with the cells on the matrix facing upward; placing the selected matrix cutter onto the cell-seeded support matrix, with a surgically sharp edge facing downward; applying downward force on a top side of the matrix cutter using at least one of a hand, a mallet, a hammer, or other tool; and removing the matrix cutter and removing an uncut portion of the cell-seeded support matrix.

In another aspect, the present embodiments are directed to a matrix cutter, including: an elliptic cylinder body; an internal hole shaped as a stadium aligned parallel with the semi-major axis of the elliptic cylinder body, and longitudinally aligned parallel with the longitudinal axis of the elliptic cylinder body; a flat top surface of the elliptic cylinder body; at least two flat gripping notches at opposite exterior sides of the elliptic cylinder body; and a surgically sharp edge around a bottom circumference of the elliptic cylinder body.

In some embodiments, the matrix cutter comprises stainless steel type 17-4PH (630) and/or UNS S17400, per ASTM A564.

In another aspect, the present embodiments are directed to a method for delivering and implanting a cell-seeded support matrix to a prepared cartilage surgery site including: stopping fluid flow and removing a dam seal sub-assembly at a surgical site; using a first applicator swab to clean and dry the surgical site where cartilage was previously cut and removed surrounding a lesion or defect; using tweezers to pick up a piece of previously cut cell-seeded support matrix by grasping an edge of the matrix; placing the cell-seeded support matrix across a delivery tip of a matrix shuttle delivery device such that the matrix lies within an outline at the delivery tip and such that a cell-containing side of the matrix is facing away from the delivery tip; using a second applicator swab to apply fibrin glue at the surgical site; inserting the matrix shuttle delivery device into a cannula at the surgical site; depressing a plunger on the matrix shuttle device to extend at least one antenna from within the delivery tip of the matrix shuttle device to push the cell-seeded support matrix out and onto the surgical site; removing the matrix shuttle device from the cannula; using a third applicator swab to reposition the cell-seeded support matrix if needed; and using a fourth applicator swab to apply fibrin glue around an edge of the cell-seeded support matrix at the surgical site.

In another aspect, the present embodiments are directed to a matrix shuttle delivery device, including: a shuttle body, wherein the shuttle body includes a substantially hollow cylinder; a delivery tip at a distal end of the shuttle body; a plunger disposed longitudinally within the shuttle body and protruding out of a proximal end of the shuttle body; at least two deployment wings disposed inside the delivery tip and attached to the plunger; and at least two holes on a distal surface of the delivery tip; wherein pushing the plunger longitudinally into the shuttle body causes the at least two deployment wings to extend externally through the at least two holes of the delivery tip.

In some embodiments, the matrix shuttle device further comprises a spring disposed longitudinally inside the shuttle body and attached to the plunger. In some embodiments, the matrix shuttle device further comprises one or more finger grips disposed at the proximal end of the shuttle body. In some embodiments, the one or more finger grips each comprise a rod that is connected at one end to an exterior surface of the shuttle body and extends radially outward away from the shuttle body, wherein the distal side of each rod is curved to accommodate a user's finger.

In some embodiments, the delivery tip includes: a cylindrical portion that is connected to the shuttle body at the proximal end of the delivery tip; a tapered portion including two sloped sides that come together in a flat surface at the distal end of the delivery tip; and an outline ledge around the distal end of the delivery tip that includes an elliptical or oblong shape, wherein a centerline of the outline ledge is substantially parallel to the flat surface at the distal end of the delivery tip. In some embodiments, the at least two holes are each positioned on the two sloped sides of the delivery tip, so that when the deployment wings are extended, a line connecting the rounded tips of the deployment wings is substantially perpendicular to the flat surface at the distal end of the delivery tip. In some embodiments, the at least two holes each comprise a diameter that is larger than a diameter of each of the at least two deployment wings.

In some embodiments, the deployment wings include: a U-shaped body; at least two wing arms comprising cylindrical rods that extend in parallel out of the U-shaped body and curve outwards away from the U-shaped body; at least two rounded tips at the distal ends of the at least two wing arms; and a circular hole at the proximal bottom of the U-shaped body. In some embodiments, the deployment wings comprise at least one member of the group consisting of silicone, ethylene propylene diene monomer (EPDM) rubber, plastic, and a flexible polymeric material.

In some embodiments, the plunger includes: a cylindrical body; a flat disc portion at the proximal end of the cylindrical body; and a recessed portion with a protruding pin at the proximal end of the cylindrical body, wherein the protruding pin comprises a small cylinder disposed perpendicular to the longitudinal axis of the cylindrical body and a rounded knob with a diameter larger than that of the small cylinder. In some embodiments, the protruding pin of the plunger passes through the circular hole at the proximal bottom of the U-shaped body of the deployment wings.

In some embodiments, the plunger and shuttle body includes at least one of acrylonitrile butadiene styrene (ABS) or plastic. In some embodiments, the shuttle body, delivery tip, and finger grips are formed as two continuous, identical shells that come together to form the matrix shuttle delivery device. In some embodiments, the spring causes the at least two deployment wings to retract inside the at least two holes when the plunger is released.

In another aspect, the present embodiments are directed to a matrix shuttle delivery device, including: a shuttle body, wherein the shuttle body includes a substantially a hollow cylinder; a delivery tip at the distal end of the shuttle body, including: a cylindrical portion that is connected to the shuttle body at the proximal end of the delivery tip; a tapered portion including two sloped sides that come together in a flat surface at the distal end of the delivery tip; and an outline ledge across the top and distal end of the delivery tip that includes an elliptical or oblong shape; a plunger disposed longitudinally within the shuttle body and protruding out of the proximal end of the shuttle body, the plunger including: a cylindrical body; a flat disc portion at the proximal end of the cylindrical body; and a recessed portion with protruding pin at the proximal end of the cylindrical body, wherein the protruding pin includes a small cylinder disposed perpendicular to the longitudinal axis of the cylindrical body and a rounded knob with a diameter larger than that of the small cylinder.

In some embodiments, the matrix shuttle delivery further includes: at least two deployment wings disposed inside the delivery tip and attached to the plunger, the deployment wings including: a U-shaped body; at least two wing arms including cylindrical rods that extend in parallel out of the U-shaped body and curve outwards away from the U-shaped body; at least two rounded tips at the distal ends of the at least two wing arms; a circular hole at the proximal bottom of the U-shaped body; and one or more finger grips disposed at the proximal end of the shuttle body, the device further including: at least two holes, each hole positioned on one of the two sloped sides of the delivery tip; and a spring disposed longitudinally inside the shuttle body and attached to the plunger, wherein pushing the plunger longitudinally into the shuttle body causes the at least two deployment wings to exit the at least two holes of the delivery tip, and wherein the spring causes the at least two deployment wings to retract inside the at least two holes when the plunger is released.

In another aspect, the present disclosures are directed toward an arthroscopic surgical method to repair a cartilage defect including: making an incision at a joint on a patient's body near the cartilage defect; inserting a cannula assembly into the incision; measuring the cartilage defect at the joint using an arthroscopic measurement tool inserted through the cannula; preparing a cartilage area around the cartilage defect; preparing and cutting a portion of cell-seeded matrix composition using a matrix cutter tool to match the shape of the prepared cartilage area; placing the portion of cell-seeded matrix composition across a delivery tip of a matrix shuttle delivery device; inserting the matrix shuttle delivery device through the cannula; depressing a plunger on the matrix shuttle delivery device to extend at least two deployment wings from within the delivery tip to push the portion of cell-seeded matrix composition off the delivery tip and onto the prepared cartilage area; and removing the matrix shuttle delivery device from the cannula.

In some embodiments, preparing a cartilage area includes: defining a region of cartilage surrounding the cartilage defect using a first cutting tool; and scraping, cutting, debriding and/or removing cartilage using one or more additional surgical cutting tools within the region of cartilage defined by the first cutting tool.

In some embodiments, the cell-seeded matrix composition includes chondrocytes seeded on one side of a bioresorbable matrix, and wherein the side of the matrix with chondrocytes is facing away from the delivery tip of the matrix shuttle delivery device.

In some embodiments, the method further includes: applying fibrin glue to the prepared cartilage prior to delivery of the cell-seeded matrix composition; applying fibrin glue around an edge of the cell-seeded matrix composition after the cell-seeded matrix composition is delivered to the prepared cartilage; removing the cannula from the incision; and surgically closing the incision.

In another aspect, the present embodiments are directed to an applicator tool including: a cylindrical rod; an applicator swab attached by adhesive to one end of the cylindrical rod; and an applicator tip attached by adhesive to another end of the cylindrical rod. In some embodiments, the cylindrical rod is composed of or includes a plastic material, the applicator swab includes cotton, polyurethane foam, and/or other similar soft, absorbent material, and the applicator tip includes soft silicone or other similar compliant material.

BRIEF DESCRIPTION OF THE DRAWINGS

The present teachings described herein will be more fully understood from the following description of various illustrative embodiments, when read together with the accompanying drawing. It should be understood that the drawing described below is for illustration purposes only and is not intended to limit the scope of the present teachings in any way.

FIG. 2A illustrates a view of an exemplary arthroscopic surgery process, according to aspects of the present embodiments.

FIG. 2B illustrates a view of an exemplary arthroscopic surgery process, according to aspects of the present embodiments.

FIG. 2C illustrates a view of an exemplary arthroscopic surgery process, according to aspects of the present embodiments.

FIG. 2D illustrates a view of an exemplary arthroscopic surgery process, according to aspects of the present embodiments.

FIG. 2E illustrates a view of an exemplary arthroscopic surgery process, according to aspects of the present embodiments.

FIG. 2F illustrates a view of an exemplary arthroscopic surgery process, according to aspects of the present embodiments.

FIG. 41A illustrates a view demonstrating a preparation of a cell-seeded support matrix composition, according to aspects of the present embodiments.

FIG. 41B illustrates a view demonstrating a preparation of a cell-seeded support matrix composition, according to aspects of the present embodiments.

FIG. 41C illustrates a view demonstrating a preparation of a cell-seeded support matrix composition, according to aspects of the present embodiments.

FIG. 47 illustrates a side view of a delivery tip of a matrix shuttle delivery device with cell-seeded support matrix placed across the delivery tip, according to aspects of the present embodiments.

FIG. 48 illustrates a side view of a matrix shuttle delivery device with deployment wings extended and a plunger pressed to deliver a cell-seeded support matrix, according to aspects of the present embodiments.

DEFINITIONS

Figure 1:
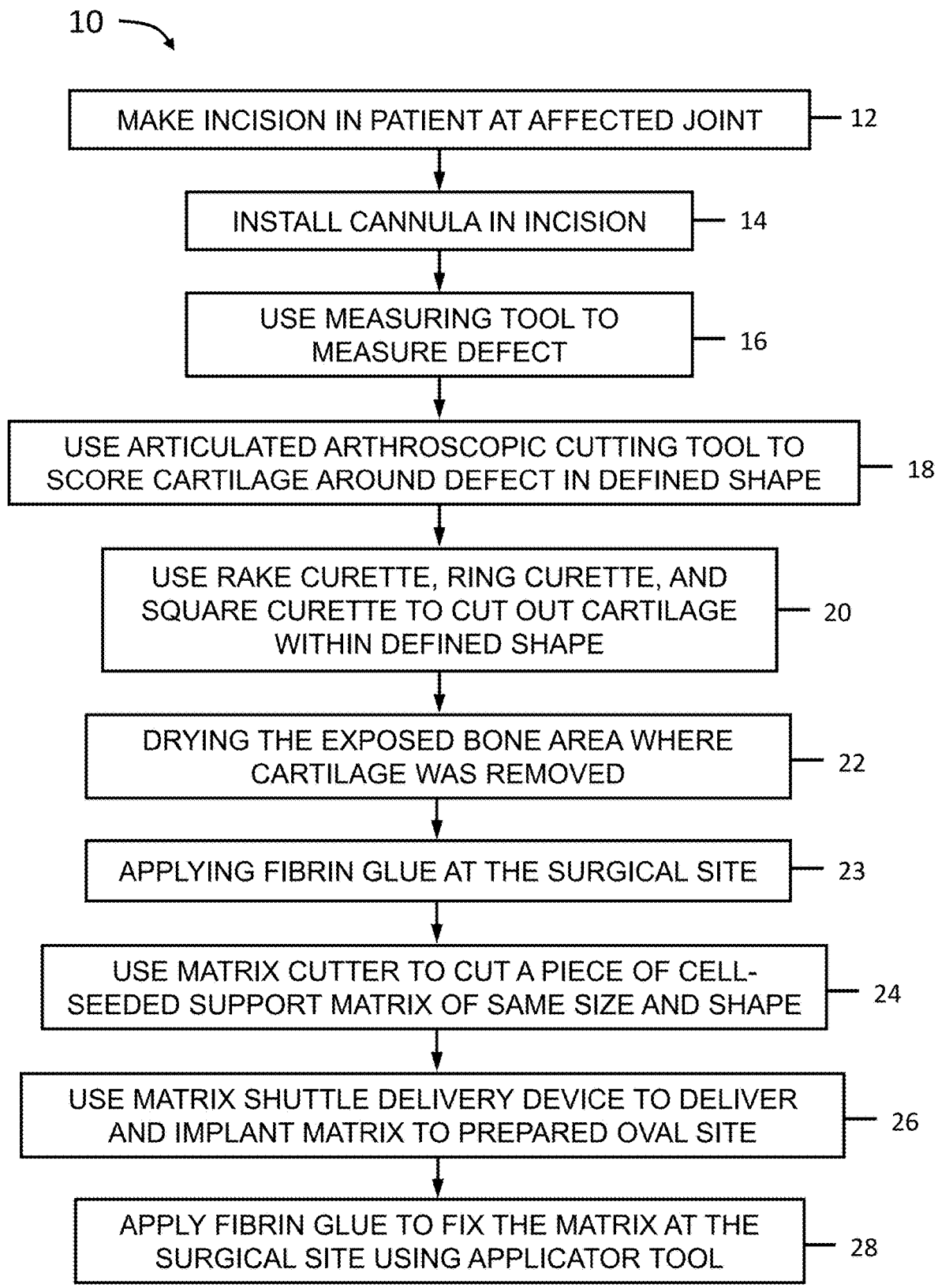
FIG. 1 illustrates a schematic of a method of conducting arthroscopic surgery, according to aspects of the present embodiments.

As used herein, the term "about," as used in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

As used herein, the term "adult" refers to a human eighteen years of age or older. In some embodiments, a human adult has a weight within the range of about 90 pounds to about 250 pounds.

As used herein, the term, "associated with" refers to two events or entities when presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to a disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

As used herein, the term "biocompatible" refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro does not result in substantial cell death, and/or their administration in vivo does not induce significant inflammation or other such adverse effects.

As used herein, the term "chondrocytes" or "cartilage cells," refers to cells that are capable of expressing biochemical markers characteristic of chondrocytes, including but not limited to type II collagen, aggrecan, chondroitin sulfate and/or keratin sulfate. In some embodiments, chondrocytes, or cartilage cells, express morphologic markers characteristic of smooth muscle cells, including but not limited to a rounded morphology in vitro. In some embodiments, chondrocytes, or cartilage cells, are able to secrete type II collagen in vitro. In some embodiments, chondrocytes, or cartilage cells, are able to secrete aggrecan in vitro. In some embodiments, chondrocytes, or cartilage calls, are able to generate tissue or matrices with hemodynamic properties of cartilage in vitro.

As used herein the term "ex vivo" refers to events that occur in tissue outside of or removed from a multi-cellular organism, such as a human and a non-human animal. In the context of cell-based systems, the term may be used to refer to events that occur within an isolated tissue sample taken from an organism (as opposed to, for example, in vivo systems).

As used herein, the term "extracellular" refers to a molecule, substance, or process that is situated or taking place outside of a cell or group of cells. In the context of cell-based systems, the term may be used to refer to natural biological matter found adjacent to and outside of a cell or group of cells (e.g., "extracellular matrix").

As used herein, the term "defect" refers to an abnormality or imperfection, for example, in tissue in a joint of a subject. In some embodiments, a defect is a cartilaginous defect. In some embodiments, a defect is a defect in tissue in an articulating joint, for example, a knee joint. In some embodiments, a defect is a chondral defect. In some embodiments, a defect is an osteochondral defect. In some embodiments, a defect may have a size ranging from about 0.1 to about 10 cm$^2$. In some embodiments, a defect may have a size that is greater than 10 cm$^2$.

As used herein, the term "density" refers to an average number of a substance, for example, cells or another object, per unit area of volume. In some embodiments, density is cell density, i.e., number of cells per unit of surface area. In some embodiments, an average density is approximated by dividing a number of cells seeded by a macroscopic surface are of a surface on which they are grown. In some embodiments, a surface is two-dimensional. In some embodiments, a surface is three-dimensional.

As used herein the term "in vitro" refers to events that occur in an artificial environment, e.g., in a test tube or reaction vessel, in cell culture, etc., rather than within a multi-cellular organism.

As used herein the term "in vivo" refers to events that occur within a multi-cellular organism, such as a human and a non-human animal. In the context of cell-based systems, the term may be used to refer to events that occur within a living cell (as opposed to, for example, in vitro systems).

As used herein, the term "medium" refers to components that support growth or maintenance of cells in culture. In some embodiments, this may include traditional liquid cell culture medium and an additional factor. In some embodiments, additional factors may include, for example, serum, antibiotics, growth factors, pharmacological agents, buffers, pH indicators and the like. In some embodiments, medium may be used in a process to isolate cells (e.g., chondrocytes and/or chondrocyte precursors) from a tissue sample (e.g., a cartilage sample). In some embodiments, tissue is mechanically disrupted (e.g., chopped, minced, blended) then combined with medium. In some embodiments, medium comprises enzymes (e.g., collagenase, protease) to digest tissue and release cells.

As used herein, the term "conditioned medium" refers to medium that has been contacted with cells to allow for the composition of medium to be modified, for example by uptake or release of one or more metabolites, nutrients, or factors.

As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

As used herein, the term "seeding" refers to a process or step whereby cells are brought into contact with a support matrix, and adhere (with or without an adhesive) to a support matrix (e.g., a collagen membrane) for a period of time. Seeded cells may divide and/or differentiate on a support matrix. In some embodiments, cells are seeded onto a support matrix prior to being implanted into a subject.

As used herein, the term "subject" refers to an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered. In some embodiments, a subject is a donor of a biological sample, tissue and/or material.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the term "substantially free of endotoxin" refers to a level of endotoxin per dose of a composition that is less than is allowed by the FDA for a biologic product (i.e., total endotoxin of 5 EU/kg body weight per hour, which for an average 70 kg person is 350 EU per total dose).

As used herein, the term "substantially free of mycoplasma and/or microbial contamination" refers to a negative reading for a generally accepted test of contamination known to those skilled in the art. For example, mycoplasma contamination is determined by subculturing a product sample in broth medium and distributing the culture over agar plates on days 1, 3, 7, and 14 at 37° C. with appropriate positive and negative controls. In some embodiments, mycoplasma contamination is determined using a real-time PCR method. The product sample appearance is compared microscopically at 100×, to that of a positive and negative control. Additionally, presence of mycoplasma contamination may be detected by inoculation of an indicator cell culture, which is incubated for 3 and 5 days then examined at 600× by epifluorescence microscopy using a DNA-binding fluorochrome. The composition is considered satisfactory if agar and/or broth media procedure and indicator cell culture procedure show no evidence of mycoplasma contamination. In some embodiments, an assay that may be utilized to assess a level of microbial contamination may be or comprise the U.S. Pharmacopeia (USP) Direct Transfer Method. This involves inoculating a sample into a tube containing tryptic soy broth media and fluid thioglycollate media. Tubes are observed periodically for a cloudy appearance (turbidity) during a specified period (e.g., 14 days) of incubation. A cloudy appearance on any day in either medium indicates contamination, with a clear appearance (no growth) indicating that a composition may be considered to be substantially free of contamination. In some embodiments, an approved alternative to a USP method for detection of microbial contamination is used, for example, a BacT/ALERT test using different media formulations.

As used herein, the term "surface area" refers to, for example, square area, $cm^2$, or to the macroscopic surface area of a substrate.

As used herein, the term "treatment" (also "treat" or "treating") refers to administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

Injuries to joints occur frequently from physical activity, for example, including but not limited to repetitive and excessive motions, overstretching, and physical trauma. Treatments for joint injuries often include surgery. Tissue, including cartilage, in the interior of an articulating joint is often difficult to access surgically, presenting challenges to treating patients with damage to joint cartilage. Certain current therapeutic intervention strategies typically involve removing damaged or dislodged cartilage from the joint. Such treatments typically provide temporary relief from symptoms of the injury, but they do not treat the origin of the lesion or defect, and, in particular, do not prevent progressive degradation of the cartilage.

The present disclosure provides improved technologies useful for treating tissue defects in articulating joints. In particular, the present disclosure provides improved matrix-induced autologous chondrocyte implantation (MACI) technologies useful for repairing a tissue defect in an articulating joint in a human subject. For example, among other things, the present disclosure provides technologies for the arthroscopic delivery of MACI implants, also known as cell-seeded support matrices. In some embodiments, provided technologies are characterized in that they achieve delivery characterized by cell number and viability comparable to those observed with non-arthroscopic delivery. Advantages of the provided methods include, for example, arthroscopic delivery that is far less invasive than open surgical strategies, e.g., which have typically been used to administer MACI implants. Provided technologies, thus, represent and embody further improvements with respect to MACI technologies for the treatment of cartilage defects.

Matrix-Induced Autologous Chondrocyte Implantation (MACI)

Matrix-induced autologous chondrocyte implantation (MACI) is a surgical procedure used to treat symptomatic, full-thickness chondral lesions of articulating joints. MACI® also refers to a commercial product owned by Vericel Corporation, known as autologous cultured chondrocytes on porcine collagen membrane. MACI is a registered trademark of Vericel Corporation, but is also used herein to describe a process, and thus is not always denoted with the registration symbol. The MACI procedure is performed most commonly on the knee, but can be performed on other joints. MACI improves on the limitations of previous methods to treat chondral defects using implanted chondrocytes, including the risk of uneven chondrocyte distribution at the time of implantation and graft hypertrophy. Given the compliant properties of the scaffold or matrix on which chondrocytes are seeded before delivery to a patient in need, the graft can be easily shaped to treat irregular chondral defects and applied to articular surfaces with multiplanar geometry (e.g., trochlea) (Jones & Cash, 2019, *Arthroscopy Techniques*, 8(3), 259-266).

Restorative treatment options for symptomatic, full-thickness chondral and osteochondral lesions of the knee continue to evolve with advancements in our understanding of cartilage biology and surgical techniques. Since the initial description by Brittberg et al., in 1994, autologous chondrocyte implantation (ACI) has gained widespread use, and surgical utilization in the United States has nearly doubled over the past decade. Although the long-term clinical results of first-generation techniques have demonstrated sustained functional improvement, there were significant technical challenges and adverse events related to the requisite use of a periosteal patch over the defect. A large number of patients demonstrated arthrofibrosis and graft hypertrophy, which necessitated additional surgical procedures to address these complications (Jones, K. J. & Cash, B. M, *Arthrosc Tech,* 2019). Ultimately, the use of periosteum was largely abandoned in favor of a bioabsorbable collagen membrane cover in 2007, significantly reducing the rate of graft hypertrophy and the rates of reoperation (Jones & Cash, 2019, *Arthroscopy Techniques,* 8(3), 259-266).

More recent ACI techniques, including MACI, use cell-loaded membranes to avoid graft-related complications and simplify the surgical technique. The MACI® scaffold (Vericel Corporation, Cambridge, MA) may use a porcine type I/III collagen membrane seeded with autologous chondrocytes at a density ranging between 250,000 and 1 million cells/cm². In a recent report of the Superiority of MACI Implant Versus Microfracture Treatment trial, clinical outcomes following the treatment of chondral defects (>3 cm²) with MACI® were clinically superior at 5 years compared with microfracture treatment (Brittberg et al., 2018, *Am. J. Sports Med.*, 46, 1343-1351). Additional case series have reported similar mid- and long-term results (Jones & Cash, 2019, *Arthroscopy Techniques*, 8(3), 259-266).

Cells

In some embodiments, the present disclosure utilizes cells from a human or non-human (xenograft) source. In some embodiments, utilized cells are human cells.

In some embodiments, utilized cells are autologous in that they are obtained from the same subject to whom a cell-seeded matrix composition(s) is administered as described herein. In some embodiments, utilized cells are allogeneic in that they are isolated from tissue of a first subject, who is a different subject from that into whom cell-seeded matrix compositions may be administered.

In some embodiments, cells may be obtained from tissue harvested from a living source (e.g., a living human). In some embodiments, cells may be obtained from tissue harvested from adult organism (e.g., an adult human). In some embodiments, cells may be obtained from tissue harvested from a human younger than 18 years of age. Alternatively or additionally, in some embodiments, cells may be obtained from tissue harvested from a deceased source (e.g., from a cadaver). In some embodiments, cells may be obtained from tissue harvested from a living non-human organism.

In some embodiments, utilized cells comprise chondrocytes. In some embodiments, utilized cells comprise human chondrocytes.

In some embodiments, a cell preparation utilized in accordance with the present disclosure may be characterized e.g., to confirm one or more features of cell identity and/or to exclude one or more contaminants or undesirable properties, etc. For example, in some embodiments, a preparation that is or comprises chondrocytes may be assessed for expression of one or more chondrocyte markers (e.g., to determine whether expression of such marker is above a predetermined threshold and/or is comparable to that observed in an appropriate reference preparation) and/or one or more fibroblast markers (e.g., to determine whether expression of such marker is below a predetermined threshold and/or is comparable to that observed in an appropriate reference preparation). In some embodiments, a chondrocyte marker may be or comprise HAPLN1, MGP, EDIL3, WISP3, AGC1, COMP, COL2A1, COL9A1, COL11A1, LECT1, 81008, CRTAC1, SOX9, and NEBL.

Cells for use according to the technologies of the present disclosure may be obtained from a biological sample, such as a tissue, cell culture, or other material, that may or may not contain chondrocytes.

In some embodiments, a cell culture may be grown from cells released from a cartilage biopsy. For example, cartilage cells may be cultured from a cartilage biopsy of a patient receiving an implant. Carticel® autologous chondrocyte product (Vericel Corporation, Cambridge, MA) is an example of a cultured chondrocyte product. In some embodiments, a cell culture comprises a collagen matrix loaded with chondrocytes. Such chondrocytes may be obtained from a cartilage biopsy and cultured prior to being loaded on the matrix, e.g., as used in the MACI® implant product.

In some embodiments, autologous chondrocytes may be expanded in culture prior to implantation to the subject from which they were isolated. In step 1, a cartilage biopsy from a patient undergoing autologous chondrocyte implantation may be shipped for processing (step 2). Biopsy material is digested at step 3 to release and harvest chondrocytes from the cartilage. The released cells are plated in tissue culture flasks and may be expanded in primary culture at step 4, and if necessary, subcultured. Once the cells reach an adequate number, they can be, optionally, cryopreserved at step 5 until a patient is ready to receive an implant. Once a patient is ready to receive cells, they may be thawed and plated into tissue culture flasks and grown to prepare an assembly culture {step 6). For use in an autologous chondrocyte implant, if a sufficient number of cells are obtained in the assembly culture, the cells may be centrifuged to a cell pellet and resuspended in shipping medium, which is the "final product", such as, for example, the Carticel® autologous chondrocyte product (step 8). This "final product" may be subjected to a number of quality control tests, including for example, a sterility test, a cell viability test, an endotoxin test, a mycoplasma test, and/or a culture composition test (step 9) to ensure that the cultured cells contain a sufficient number of chondrocytes. If the cultured cells pass all tests, they may be shipped (step 10) to the patient for implantation (step 11).

Alternatively, when the assembly culture from step 6 is to be used in a MACI® implant, the cells may be resuspended in culture medium, seeded onto a collagen scaffold, and cultured for 4 days (step 7). At the end of the culture period, cells may be rinsed with shipping medium to produce a final product for MACI® implants. This product may also be subjected to quality control tests. Accordingly, whether the final product is a suspension of cultured chondrocytes, such as Carticel® autologous chondrocytes, or the final product is a scaffold-seeded product for MACI® implants, evaluation of cell identity may be useful as a lot identification assay or lot release assay, to confirm the composition of a cell culture as containing chondrocytes prior to shipment of the culture.

In some embodiments, RNA expression levels for genes overexpressed by chondrocytes (e.g., HAPLN1) may be measured in cultured cells. In some embodiments, RNA expression for genes overexpressed by synoviocytes (e.g., MFAP5) may be measured in cultured cells. In some embodiments, RNA expression levels may be presented as a ratio of expression of a chondrocyte marker (e.g., HAPLN1) versus expression of a synoviocyte marker (MFAP5). In some embodiments, cultured chondrocytes may demonstrate relative RNA expression levels (HAPLN1 vs. MFAP5) of about −2, about −1, about 0, about +1, about +2, about +3, about +4, about +5, about +6, about +7, about +8 about +9, about +10 or more on a log scale. In some embodiments, cultured chondrocytes may demonstrate relative RNA expression levels ranging from about −2 to about +10, about −1 to about +9, about 1 to about 10, about +3 to about +8, about +5 to about +7 or ranges therein. In some embodiments, cultured synoviocytes may demonstrate relative RNA expression levels of about less than −2 on a log scale. In some embodiments, cultured synoviocytes may demonstrate relative RNA expression levels ranging from less than −2 to −10 on a log scale.

In some embodiments, chondrocytes prepared from a source cell preparation may be present in culture at a density sufficient to seed a support matrix with at least 250,000 cells/cm². In some embodiments, chondrocytes expanded in culture may be dedifferentiated when present in a monolayer culture. In some embodiments, dedifferentiated chondrocytes may exhibit a fibroblastic phenotype. In some embodiments, dedifferentiated chondrocytes may downregulate expression of a gene encoding an extracellular matrix (ECM) protein, for example, ACAN and/or COL2A1. In some embodiments, dedifferentiated chondrocytes may produce and/or secrete a lesser amount of ECM protein, for example, collagen (e.g., type II collagen) and/or aggrecan (also known as cartilage-specific proteoglycan core protein or chondroitin sulfate proteoglycan 1). Without wishing to be bound by theory, de-differentiation may occur after removal of chondrocytes from 3-dimensional cartilage matrix and is observed during expansion of cells in monolayer culture.

In some embodiments, chondrocyte preparations utilized herein comprise a sufficient number of cells to seed a support matrix. In some embodiments, chondrocyte preparations comprise at least about $3\times10^6$, $4\times10^6$, $5\times10^6$, $6\times10^6$, $7\times10^6$, $8\times10^6$, $9\times10^6$ or more cells following a second passage. In some embodiments, chondrocyte preparations comprise at least about $3\times10^6$ cells after a second passage. In some embodiments, chondrocyte preparations disclosed herein comprise at least about $1\times10^7$, $2\times10^7$, $3\times10^7$, $4\times10^7$, $5\times10^7$, $6\times10^7$, $7\times10^7$, $8\times10^7$, $9\times10^7$ or more cells at a final passage. In some embodiments, chondrocyte preparations utilized herein comprise at least $1\times10^7$ cells at a final passage.

In some embodiments, chondrocyte cultures are about 50%, 60%, 70%, 80%, 90%, 95%, 98% or more confluent. In some embodiments, chondrocyte cultures are about 100% confluent. In some embodiments, chondrocyte cultures are about 50% to 90% confluent.

In some embodiments, chondrocytes are seeded on a support matrix at density of at least 250,000 cells/cm$^2$, 300,000 cells/cm$^2$, 400,000 cells/cm$^2$, 500,000 cells/cm$^2$, 600,000 cells/cm$^2$, 700,000 cells/cm$^2$, 800,000 cells/cm$^2$, 900,000 cells/cm$^2$, 1,000,000 cells/cm$^2$, or more.

Among other things, the present disclosure utilizes cell preparations in which a significant percentage of cells are viable; such high viability cell preparations can materially improve, and may be required for, successful treatment of a particular lesion or defect. In some embodiments, at least 70%, 75%, 80%, 85%, 90%, 95%, 98% or more of cells present in a preparation are viable. In some embodiments, at least 90% of chondrocytes in a preparation are viable.

In some embodiments, a composition of the disclosure utilized herein may be substantially free of components used during preparation of a source cell preparation and during expansion of chondrocytes (e.g., fetal bovine serum albumin, fetal bovine serum and/or horse serum). For example, in some embodiments, a composition utilized herein comprises less than 10 µg/ml, 5 µg/ml, 4 µg/ml, 3 µg/ml, 2 µg/ml, 1 µg/ml, 0.05 µg/ml fetal bovine serum albumin. In some embodiments, a cell preparation may be substantially free of mycoplasma, endotoxin, and/or microbial (e.g., aerobic microbe(s), anaerobic microbes(s) and/or fungi) contamination. In some embodiments, a cell preparation may test negative for mycoplasma, endotoxin and/or microbial contamination.

Support Matrix

A support matrix for use in accordance with the present disclosure may be made of a material to which relevant utilized cells adhere. In some embodiments, a support matrix comprises and/or is coated with an adhesive agent that facilitates and/or enables cell adherence.

In some embodiments, a support matrix supports cell proliferation.

In some embodiments, a support matrix is bioresorbable. In some such embodiments, a bioresorbable matrix may degrade over a period of hours, days, weeks or months. For example, a bioresorbable matrix may degrade within at least 24 hours, at least 7 days, at least 30 days or at least 6 months. In some embodiments, a support matrix may act as a hemostatic barrier inhibiting penetration of adjacent cells and tissues into a particular area of the body, for example, an area requiring treatment (e.g., an articular joint).

In some embodiments, a support matrix may be a gel, a solid, or a semi-solid. In some embodiments, a support matrix may be impermeable, permeable or semi-permeable (e.g., comprising pores). In some embodiments, a support matrix may be comprised of a synthetic material, a natural material, or a combination thereof.

In some embodiments, a support matrix may have a structure that comprises a membrane, microbead, fleece, thread, gel or combination thereof.

In some embodiments, a support matrix may be or comprise biological material generated by cells; in some such embodiments, a biological material may be generated by cells in culture. Alternatively, in some such embodiments, a biological material may be generated by cells in tissue (e.g., in vivo). In some embodiments, such biological material may be generated by cells that are allogeneic to a subject who will receive treatment as described herein.

In some embodiments, a support matrix may be or comprise collagen. For example, a support matrix may be or comprise type I collagen, type II collagen, type III collagen, or a combination thereof (e.g., may include a combination of type I collagen and type II collagen, or may include a combination of type I collagen and type III collagen). In some embodiments, a support matrix is comprised of primarily type I collagen on a first side and type III collagen on a second side. In some embodiments, a first side of a support matrix comprising type I collagen is a smooth surface. In some embodiments, a second side of a support matrix comprising type III collagen is a rough surface. In some embodiments, a rough surface of a support matrix is suitable for cell seeding. In some embodiments, a smooth surface of a support matrix is suitable to contact a joint surface.

In some embodiments, some or all collagen in a support matrix for use in accordance with the present disclosure may be cross-linked; in some embodiments, it may be uncross-linked.

In some embodiments, collagen utilized in accordance with the present disclosure may be derived from an animal such as a pig. In some embodiments, collagen may be derived from the peritoneum of a pig.

In some particular embodiments as described herein, a support matrix comprises a combination of type I and type III porcine collagen.

In some embodiments, cells (e.g., chondrocytes) seeded onto and/or cultured on a support matrix as described herein may produce one or more extracellular matrix proteins (e.g., collagen) that interact with and/or become incorporated into, a support matrix.

In some embodiments, a support matrix may include proteins, polypeptides, hyaluronic acid) and/or polymers (e.g., elastin, fibrin, laminin, fibronectin). In some embodiments, a support matrix may be cell-free.

In some embodiments, a support matrix may have a surface area, size, shape, and/or dimension appropriate for treatment of a particular chondral or osteochondral defect, lesion or injury. In some embodiments, a support matrix may be provided in a form (e.g., a sheet form) that is readily shaped (e.g., by cutting, trimming, etc.) for administration to a particular chondral or osteochondral defect.

In some embodiments, a surface area of a support matrix may be at most about 10 cm², 5 cm², 4 cm², 3 cm², 2 cm², 1 cm² or smaller. In some embodiments, a support matrix may have a surface area of about 2 cm². In some embodiments, a support matrix may have a surface area of about 3 cm². In some embodiments, a support matrix may have a surface area of about 4 cm². A dimension of a support matrix may be any dimension necessary to achieve a desired surface area suitable for treating a chondral and/or osteochondral defect. For example, dimensions of a 5 cm² support matrix may be about 1 cm×5 cm, 2 cm×2.5 cm, 3 cm×1.7 cm, or 4 cm×1.3 cm. In some embodiments, a surface area of a support matrix (e.g., collagen membrane) may be about 5 cm² with dimensions of about 1 cm×5 cm. In some embodiments, a surface area of a support matrix (e.g., collagen membrane) may be about 2 cm² with dimensions of about 2×1 cm². In some embodiments, the largest dimension of a support matrix does not exceed about 5 cm at its maximum length. In some embodiments, the largest dimension of a support matrix does not exceed about 10 cm at its maximum length. In some embodiments, the support matrix has an irregular shape.

Cells Seeded on Support Matrix

Among other things, the present disclosure utilizes compositions comprising cultured cells (e.g., chondrocytes) seeded onto a support matrix (e.g., collagen membrane).

Typically, cells that have been cultured for a period of time (e.g., 3 days to 5 weeks) may be present on or in a support matrix. In some embodiments, cells seeded onto a support matrix may be adherent. In some embodiments, cells may be adherent to a support matrix to an extent that they do not wash off a matrix during subsequent cell culturing steps, are not displaced from a matrix during transport, and/or are not displaced from a matrix during a surgical procedure to implant a matrix.

Among other things, in some embodiments, the present disclosure utilizes cell-seeded support matrices in which a significant percentage of cells are viable; such high viability of cells present on a cell-seeded matrix can materially improve, and may be required for, successful treatment of a particular lesion or defect. In some embodiments, at least 70%, 75%, 80%, 85%, 90%, 95%, 98% or more of cells present on a cell-seeded matrix are viable. In some embodiments, at least 90% of chondrocytes present on a cell seed matrix are viable.

In some embodiments, cells seeded onto a cell-seeded support matrix are viable for at least about 1 day, 2 days, 3 days, 4, days, 5 days, 6 days, 7 days, 8 days, 9 days, 10 days, 11 days, 12 days, 13 days, 2 weeks, 3 weeks or more. In some embodiments, cells seeded onto a support matrix divide. In some embodiments, a cell-seeded support matrix is stored at about 4° C. to about 37° C.

In some embodiments, a cell-seeded support matrix comprises at least 250,000 cells/cm², 300,000 cells/cm², 400,000 cells/cm², 500,000 cells/cm², 600,000 cells/cm², 700,000 cells/cm², 800,000 cells/cm², 900,000 cells/cm², 1,000,000 cells/cm², or more. In some embodiments, a cell-seeded matrix comprising greater than 250,000 cells/cm² 300,000 cells/cm², 400,000 cells/cm², 500,000 cells/cm², 600,000 cells/cm², 700,000 cells/cm², 800,000 cells/cm², 900,000 cells/cm², 1,000,000 cells/cm² is suitable for implant into a subject.

In some embodiments, a cell-seeded support matrix comprises at least $5\times10^6$, $7.5\times10^6$, $1.0\times10^7$, $1.5\times10^7$, $2.0\times10^7$, $2.5\times10^7$, $3.0\times10^7$ or more cells. In some embodiments, a 20 cm² porcine type I and type III collagen membrane comprises about $1.0\times10^7$ chondrocytes to about $2.0\times10^7$ chondrocytes. In some embodiments, a 14.5 cm² porcine type I and type III collagen membrane comprises about $7.5\times10^6$ chondrocytes to about $1.5\times10^7$ chondrocytes.

In some embodiments, a cell-seeded support matrix may comprise medium (e.g., DMEM) and supplements (e.g., fetal bovine serum, antibiotic). In some embodiments, medium comprises about 7%, about 8%, about 9%, about 10%, about 11% fetal bovine serum. In some embodiments, medium may be supplemented with 8.9%+/−0.2% fetal bovine serum and gentamicin.

In some embodiments, a cell-seeded support matrix may have a surface area of at most about 20 cm², 10 cm², 5 cm², 4 cm², 3 cm², 2 cm², 1 cm² or smaller. In some embodiments, a cell-seeded support matrix may have a surface area of about 2 cm². In some embodiments, a cell-seeded support matrix may have a surface area of about 3 cm². In some embodiments, a cell-seeded support matrix may have a surface area of about 4 cm². In some embodiments, a cell-seeded support matrix may have a surface area of about 5 cm². In some embodiments, the largest dimension of a cell-seeded support matrix does not exceed about 5 cm at its maximum length. In some embodiments, the largest dimension of a cell-seeded support matrix does not exceed about 10 cm at its maximum length. In some embodiments, a cell-seeded support matrix may be trimmed, shaped, cut, molded or formed and corresponds to a shape of a defect, lesion, and/or injury in need of treatment. In some embodiments, a cell-seeded support matrix is of an irregular shape.

In some embodiments, a cell-seeded support matrix may be substantially free of components used during preparation of a source cell preparation of during expansion of chondrocytes (e.g., fetal bovine serum albumin, fetal bovine serum and/or horse serum). For example, in some embodiments, a cell-seeded support matrix utilized herein comprises less than 10 µg/ml, 5 µg/ml, 4 µg/ml, 3 µg/ml, 2 µg/ml, 1 µg/ml, 0.05 µg/ml fetal bovine serum albumin. In some embodiments, a cell-seeded support matrix may be substantially free of mycoplasma, endotoxin, and/or microbial (e.g., aerobic microbe(s), anaerobic microbes(s) and/or fungi) contamination.

In some embodiments, a cell-seeded support matrix composition, prepared and/or utilized in accordance with the present disclosure, comprises a biocompatible adhesive or glue. In some embodiments, a least a portion of a cell-seeded matrix may be coated with a biocompatible adhesive or glue. In some embodiments, a biocompatible adhesive or glue may form a layer over cells on a support matrix. In some embodiments, a biocompatible adhesive or glue may form a layer under cells on a support matrix. In some embodiments, a cell-seeded support matrix comprises multiple layers of biocompatible adhesive or glue and cells. In some embodiments, a biocompatible adhesive or glue may be impregnated within a support matrix.

In some embodiments, the present disclosure utilizes cells and glue, and/or adhesive, combined together in a mixture of one or more alternating layers of cells and glue, and/or adhesive, on a surface or edge of a support matrix.

In some embodiments, biocompatible adhesives or glues used in compositions of the disclosure may include an organic fibrin glue (e.g., Tisseel®, fibrin based adhesive available from Baxter, Austria) or a fibrin glue prepared during surgery using autologous blood.

Cell Sheets

Among other things, the present disclosure utilizes compositions comprising cultured cells (e.g., chondrocytes) formed into a sheet (i.e., a cell sheet).

In some embodiments, a cell sheet comprises cells in their natural extracellular matrix (ECM). In some embodiments, a cell sheet comprises chondrocytes in their natural ECM. In some embodiments, a natural ECM comprises collagen, proteoglycans, hyaluronic acid, and/or chondroitin sulfate.

In some embodiments, a cell sheet comprises a confluent cell monolayer, the confluent cells being in their natural extracellular matrix.

Injuries and Sites

In some embodiments, the present disclosure contemplates use of cells (e.g., chondrocytes) seeded and grown on a support matrix (e.g., collagen membrane) to treat/repair cartilage defects, lesions, and/or injuries in a subject. In some embodiments, cartilage defects, lesions, and/or injuries may be located in an articulating joint (for example, knee, ankle, elbow, shoulder, hip, or wrist) of a subject. In some embodiments, a defect in a medial femoral condyle, a lateral femoral condyle, a patella, or a trochlea of a subject may be treated using technologies of the present disclosure.

Types of injuries that can lead to a cartilage defect treatable using the technologies of the present disclosure may include but are not limited to those caused by chronic and/or repetitive actions, prolonged strenuous physical activity, and trauma. Some examples of chronic and/or repetitive movements include but are not limited to walking, running, cycling, climbing, and other movements performed during exercise. Some examples of prolonged strenuous activity include but are not limited to lifting heavy objects and other forms of physical labor. Some examples of trauma include but are not limited to falls, collisions, and sports-related injuries.

In some embodiments, a subject who may be treated is an adult human. In some embodiments, a subject who may be treated is under the age of 18. In some embodiments, a subject who may be treated is a human between 10 and 17 years of age; in some such embodiments, a subject does not have an open growth plate. In some embodiments, a subject displays symptoms of a cartilage defect. In some embodiments, symptoms of a cartilage defect may include joint pain, joint swelling, and/or changes in joint flexibility and/or movement. In some embodiments, a subject may be asymptomatic.

Methods

The present disclosure provides technologies for the delivery of compositions to a surgical site, the compositions comprising cells, which compositions may be useful, for example, for treatment of chondral and/or osteochondral lesions (e.g., for example, focal lesions in the load bearing region of a knee's articular cartilage).

In some embodiments, the present disclosure provides technologies that permit and/or achieve treatment of clinically significant chondral and/or osteochondral lesions, defects, injuries and/or trauma. In some embodiments, treatment comprises tissue repair and/or regeneration.

In some embodiments, compositions comprising chondrocytes may be implanted into a subject at or near a site of a lesion, defect, injury and/or trauma, for example, at or near an articular surface, using arthroscopic methods. Articular surfaces that may be treated using the methods and compositions of the present disclosure include articular surfaces of, for example, a knee, ankle, wrist, hip, elbow, and/or shoulder.

Open Administration

Traditionally, procedures involving the implantation of a cell-seeded support matrix at a site of a defect, lesion and/or injury, have been performed under open surgical conditions requiring a large incision adjacent to the site. The implantation of a cell-seeded support matrix has traditionally been performed via an arthrotomy adjacent to the site under sterile conditions. In many of these procedures, a mini-arthrotomy is used. Mini-arthrotomy to repair knee defects (e.g., lesions on the condyle and patella) generally requires an incision with a length ranging from about 6 cm to about 10 cm. Open surgical procedures such as arthrotomy are typically used because they provide surgeons the ability to visualize and measure defects, as well as to physically manipulate the implant near the defect with relative ease.

The present disclosure appreciates various disadvantages of open surgical methods, including those traditionally used in the MACI procedure, when compared to minimally invasive methods such as arthroscopy. For example, the relatively large incisions required to perform many open surgical techniques, including those traditionally used in the MACI procedure, present an increased risk of infection, an increased risk of significant scarring, longer recovery times, and increased pain severity, relative to the same metrics following minimally invasive procedures such as arthroscopic implantation.

In such open surgical procedures, typically, an incision may be made to allow access to a joint to be surgically treated, such that the joint and its internal tissue (e.g., cartilage) are exposed and visible to a physician performing the procedure. Typically, preparation of the surgical site may include washing the site and removing damaged cartilage from the site. Typically, a cell-seeded support matrix is placed with cells facing (e.g., in contact with) a surface to be treated. In some such procedures, a cell-seeded support matrix is implanted into, and/or over, a site of a lesion, defect and/or injury. A cell-seeded support matrix may be provided in a form (e.g., a sheet form) that is readily shaped (e.g., by folding, cutting, trimming etc.) for administration to a chondral or osteochondral defect. In some procedures, a cell-seeded support matrix is shaped into a form that uniquely fits or adheres to a chondral or osteochondral defect of a subject. The cell-seeded support matrix is typically secured in the site using a fixation method, for example, fibrin glue fixation. The site may then be closed, leaving the cell-seeded matrix remaining in the site.

Arthroscopic Delivery

Arthroscopy (also called arthroscopic surgery or keyhole surgery) is a minimally invasive surgical procedure on a joint in which an examination and/or treatment of damage is performed using an arthroscope, which is an endoscope that is inserted into the joint through a small incision. Arthroscopic procedures can be performed under numerous surgical scenarios, including but not limited to ACL reconstruction, meniscus reconstruction, and cartilage repair.

Arthroscopic surgery has become a preferred surgical method due at least in part to its positive impact on patient health outcomes, including but not limited to minimal soft tissue trauma, low post-operative pain, fast healing times, and low infection rates. Many of the surgical repairs that benefit from MACI are at sites that are accessible using arthroscopic surgical methods. The present disclosure provides technologies that permit the MACI procedure via an arthroscopic delivery method.

A critical advantage of arthroscopic surgery over traditional open surgery is that a joint does not have to be opened and fully exposed during the surgical procedure. In some arthroscopic procedures performed on the knee, only around two small incisions are made: one for the arthroscope and at least one for the surgical instruments to be used in the knee cavity. This may reduce recovery time and may increase the rate of success due to reduced trauma to connective tissue, as compared to traditional open surgical procedures. In recent years, arthroscopy has gained popularity owing at least in part to evidence of faster recovery times with less scarring, due at least in part to smaller incisions. Irrigation fluid (most commonly normal saline) may be used to distend the joint and make a surgical space.

In typical arthroscopic procedures, the surgical instruments used are smaller than traditional surgical instruments. Surgeons view the joint area on a video monitor, and can diagnose and repair defects in joint tissue. It is possible to perform an arthroscopic examination of almost every joint. Arthroscopic procedures are most commonly performed on the knee, shoulder, elbow, wrist, ankle, foot, and hip.

The present disclosure appreciates the source of a challenge encountered in delivery of cell-seeded matrix compositions via arthroscopic procedures. For example, among other things, the present disclosure identifies that, absent technologies described herein, it may be difficult or impossible to maintain appropriate (e.g., sufficient) levels of cell viability. Among other things, the present disclosure provides solutions. For example, the present disclosure provides technologies that are demonstrated herein to achieve arthroscopic delivery while maintaining cell viability (e.g., as assessed by one or more parameters described herein) reasonably comparable to those found with certain open surgical methods. The present disclosure describes certain surprising and unexpected results that provided technologies can achieve (e.g., see Example 5 herein), including cell viability levels that can that exceed those obtained by certain open surgical delivery methods.

In some embodiments, at least two incisions may be made adjacent to the location of a defect to be treated arthroscopically. In some embodiments, incisions may have a length in a range from about 1 cm to about 3 cm. In some embodiments, at least one incision may be made to accommodate the insertion of an arthroscope. In some embodiments, at least one incision may be made to accommodate the insertion of a cannula. In some embodiments, at least 2, at least 3, or at least 4 incisions may be made. In some embodiments, at least 2 incisions may be made, each to accommodate the insertion of a cannula.

In some embodiments, the size and/or shape of a defect may be determined prior to arthroscopic implantation of a cell-seeded matrix to a defect. In some embodiments, the size and/or shape of a defect may be determined by using a surgical measuring device. In the present disclosure, the surgical measuring device may be an arthroscopic probe and ruler with markings with millimeter-scale spacings.

In some embodiments, a cell-seeded support matrix may be cut using a matrix cutter to form a regular shape (e.g. an oval, a circle, a rectangle, a square, etc.).

In some embodiments, a cell-seeded support matrix may be implanted at a site of a defect, lesion and/or injury using an arthroscopic technique. In some embodiments, when a cell-seeded support matrix is implanted at a site of a defect, lesion, and/or injury using an arthroscopic technique, a matrix may be placed with cells facing (e.g., in contact with) a surface to be treated. In some embodiments, a cell-seeded support matrix may be arthroscopically implanted into, and/or over, a site of a lesion, defect, and/or injury. In some embodiments, a cell-seeded support matrix may be provided in a form (e.g., a sheet form) that is readily shaped (e.g., by cutting, trimming, etc.) for arthroscopic administration to a chondral or osteochondral defect. In some embodiments, a cell-seeded support matrix may be cut or shaped into a form that uniquely fits or adheres to a subject's chondral or osteochondral defect, prior to arthroscopic implantation.

In some embodiments, a region of cartilage surrounding a defect or lesion is defined by pressing a sharp cutting tool (e.g., an articulated arthroscopic cutting tool) into the cartilage, and is then removed by using one or more cutting tools (e.g., a ring curette, a square curette, or a rake curette) to form a region of exposed bone of a particular shape (e.g., an oval, an ellipse, a circle, a square, a rectangle, etc.).

In some embodiments, a single matrix may be utilized to treat multiple defects via arthroscopy. In some embodiments, a plurality of defects may be treated, each with a different matrix, at least some of which are delivered via arthroscopy. In some embodiments, one or more defects may be treated with a plurality of individual matrices via arthroscopy.

In some embodiments, following treatment comprising arthroscopic delivery of a composition of the present disclosure, a region treated (e.g., an articular joint) may be evaluated using a screening method (e.g., magnetic resonance imaging). In some embodiments, a treated region may be evaluated for filling, repair, and/or healing of a defect, lesion, and/or injury.

In some embodiments, a cell-seeded support matrix may be arthroscopically implanted at a site of a defect, lesion, and/or injury using at least one tool selected from among a cannula assembly, an articulated arthroscopic cutting tool, a ring curette, a square curette, a rake curette, a matrix shuttle delivery device, and an applicator tool.

In some embodiments, a cannula may have an inner diameter of about at least 5 mm, at least 6 mm, at least 7 mm, at least 8 mm, at least 9 mm, or at least 10 mm. In some embodiments, a cannula may have an inner diameter from about 8 mm to about 9 mm. In some embodiments, a cannula may have an inner diameter greater than 10 mm. In some embodiments, a cannula may have an inner diameter from about 15 mm to about 20 mm. In some embodiments, the cannula may have a length that is about 2 cm, about 3 cm, about 4 cm, about 5 cm, about 6 cm, about 7 cm, about 8 cm, about 9 cm, or about 10 cm or longer. In some embodiments, a cannula may have a length that is in a range from about 2 cm to about 10 cm. In some embodiments, a cannula has a length that is about 4.5 cm. In some embodiments, the length of a cannula may depend on the location of the site of the defect to be treated. For example, a cannula used to treat a hip defect may have a length that is about 12 cm to about 20 cm. In some embodiments, a cannula used to treat a hip defect may have a length that is about 16.5 cm. In some embodiments, a cannula used to treat a shoulder defect may have a length that is about 12 cm to about 20 cm. In some embodiments, a cannula used to treat a shoulder defect may have a length that is about 16.5 cm. As an additional example, a cannula used to treat a knee defect may have a length that is in a range from about 2 cm to about 7 cm. In some embodiments, a cannula used to treat a knee defect may have a length that is about 4.5 cm. In some embodiments, a cannula may be composed of a material comprising plastic. In some embodiments, a cannula may be composed of a material comprising metal. In some embodiments, a cannula may be composed of a material selected from the group consisting of plastics, metals, rubber, silicone, fiberglass, and combinations thereof (for example, composite materials).

In some embodiments, one end of a cannula may be truncated in a curved shape around a circumference of the cannula, and may form a curved assessment edge that may facilitate visual inspection of a curved condyle or other surface on a bone.

In some embodiments, a cell-seeded support matrix may be arthroscopically delivered to a surgical site by using tweezers or other tool to place a previously cut or shaped portion of a cell-seeded support matrix onto a matrix shuttle device, pushing the shuttle device into a cannula positioned in a surgical site, pressing a plunger on the matrix shuttle device to push out deployment wings that may deliver the cell-seeded support matrix onto a surgical site. In some embodiments, a cell-seeded support matrix may traverse the entire length of a cannula.

In some embodiments, after a cell-seeded support matrix is implanted into a defect, lesion, and/or injury, a covering patch may be secured using e.g., a biocompatible adhesive, sealant, or suture. In some embodiments, a covering patch may serve to cover an area to prevent infiltration of undesirable cells and/or biological factors (e.g., fibroblasts, macrophages) from surrounding tissue into an area to be treated. In some embodiments, a covering patch comprises any support matrices described herein, and/or may include hyaluronic acid, fibrin, and/or polylactic acid. In some embodiments, a covering patch may be cell-free and resorbable. In some embodiments, a covering patch may be semi-permeable.

In some embodiments, biocompatible adhesives or glues used to secure a covering patch may include an organic fibrin glue or sealant (e.g., Tisseel®, fibrin-based adhesive available from Baxter, Austria) or a fibrin glue prepared during surgery using autologous blood.

In some embodiments, a biocompatible adhesive or glue may be applied to a defect prior to placement of a cell-seeded support matrix over, or into, a defect. In some embodiments, a biocompatible adhesive or glue may be applied to a cell-seeded support matrix prior to placement over, or into, a defect. In some embodiments, a biocompatible adhesive or glue may be applied to a periphery of an implanted cell-seeded support matrix.

FIG. 1 illustrates a schematic of a method 10 of conducting arthroscopic surgery, according to aspects of the present embodiments. The method 10 may generally include the steps of making an incision in a patient at an affected joint (e.g. knee, shoulder, elbow, etc.) (step 12); installing a cannula in the incision (step 14), using an arthroscopic measurement probe to measure a defect in the cartilage at the joint (step 16); using an articulated arthroscopic cutting tool to outline and score the cartilage surrounding the defect in a particular shape (e.g. oval, circle, square, rectangle, oblong, etc.) (step 18); using a cutting tool (e.g. rake curette, ring curette, square curette, etc.) to cut, remove, and debride the cartilage within the outlined shape (step 20); drying the surgical site where the cartilage was removed by stopping a flow of fluids, draining, suctioning, and drying by using an applicator tool (step 22); applying fibrin glue at the surgical site (step 23); using a matrix cutter to cut a portion of a cell-seeded support matrix (or MACI graft or MACI implant) (step 24); using a matrix shuttle delivery device to deliver and implant the cell-seeded support matrix to the prepared surgical site (step 26); and applying fibrin glue (or other suitable material) to the defect site using an applicator tool (step 28).

FIG. 2 illustrates views of an exemplary arthroscopic surgery process, according to aspects of the present embodiments. FIG. 2A corresponds to step 16 of method 10, and shows a cartilage-covered joint 42. In some embodiments, this joint may be a medial femoral condyle, a lateral femoral condyle, a patella, or a trochlea, or other joint of a subject or a patient. FIG. 2A also shows a flexible ruler 44 extended from a measurement tool. FIG. 2B corresponds to step 18 of method 10, and shows a sharp blade 46 attached to an articulated arm 48 cutting the cartilage 42. FIG. 2C corresponds to step 20 of method 10, and shows a ring curette 50 removing portions of the cartilage 42. FIG. 2D corresponds to step 22 of method 10, and shows a matrix applicator 56 drying the exposed bone 54 at the joint, with an outline 52 defined by cutting away the cartilage 42. FIG. 2E corresponds to step 26 of method 10, and shows a shuttle device 58 delivering a portion of pre-cut cell-seeded support matrix 60 that matches the shape of the prepared area 52, within the cartilage 42. FIG. 2F corresponds to step 28 of method 10, and shows an applicator tool 62 adjusting the position of the cell-seeded support matrix 60 and applying fibrin glue, within the cut region 52 of the cartilage 42.

Systems/Tools/Devices

Provided herein are systems, tools, devices, and instrument systems useful for practicing the methods of the invention, which will allow for the convenient practice of the methods of the invention in a surgical setting.

In some embodiments, at least one custom device or tool may be used to perform methods described herein.

Figure 3:
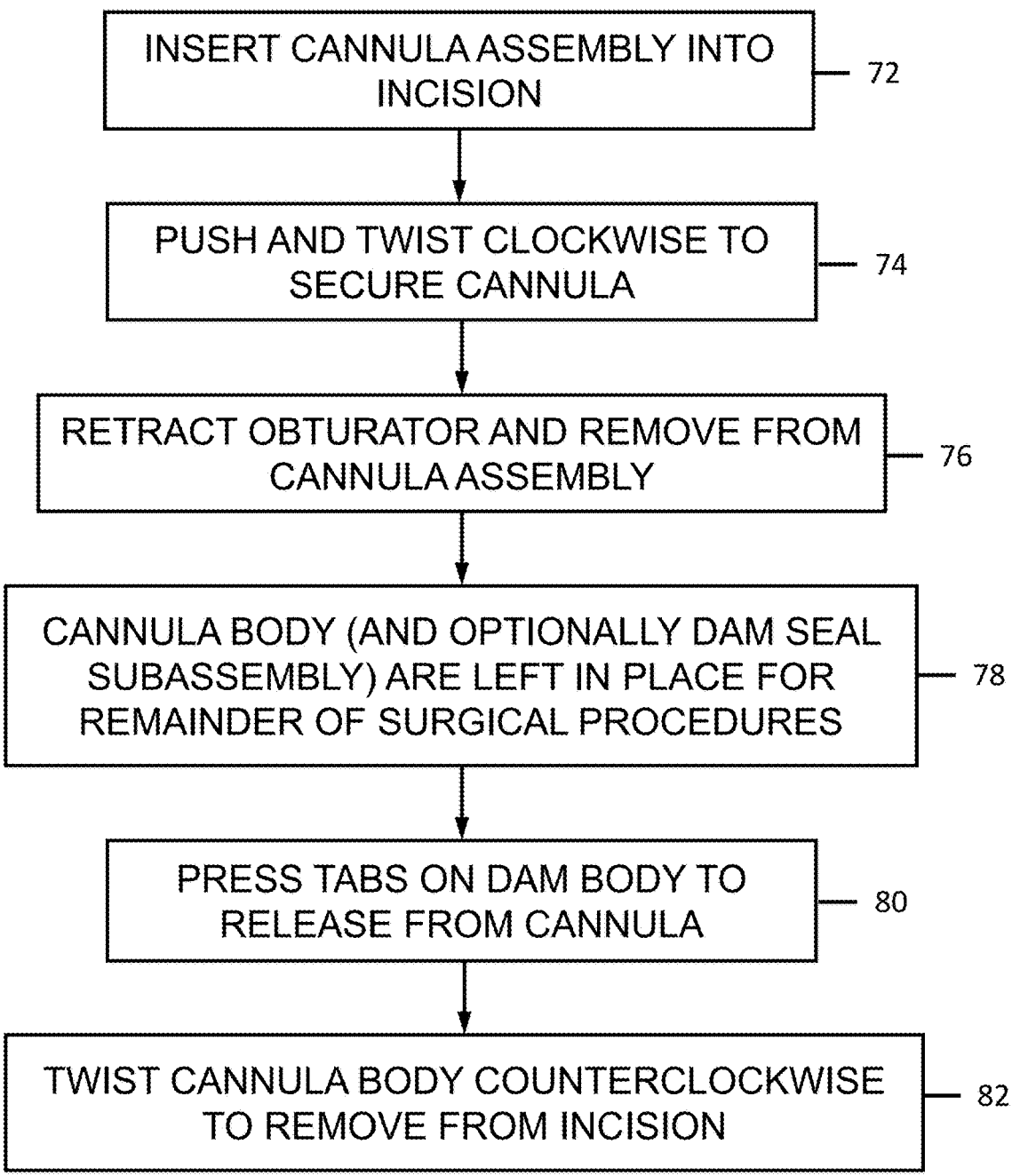
FIG. 3 illustrates a schematic of a method of using a cannula assembly during an arthroscopic surgery, according to aspects of the present embodiments.

FIG. 3 illustrates a schematic of a method 70 of using a cannula assembly during an arthroscopic surgery, according to aspects of the present embodiments. The method 70 may generally include the steps of inserting a cannula assembly into an incision at a joint of a patient (step 72), where the cannula assembly may include an obturator and a dam seal sub-assembly. Once the cannula assembly is inserted, the method 70 may include pushing and twisting the cannula body clockwise to secure it at the incision site (step 74); retracting the obturator and removing it from the cannula assembly (step 76), to leave behind the cannula body and dam seal sub-assembly for conducting one or more arthroscopic surgery procedures (step 78). The dam seal sub-assembly may be removed from the cannula body if desired by pressing on tabs on sides of the dam body to release the dam body (step 80). When the arthroscopic surgery procedures are completed, the cannula body may be removed from the incision site by twisting it counterclockwise (step 82).

Figure 4:
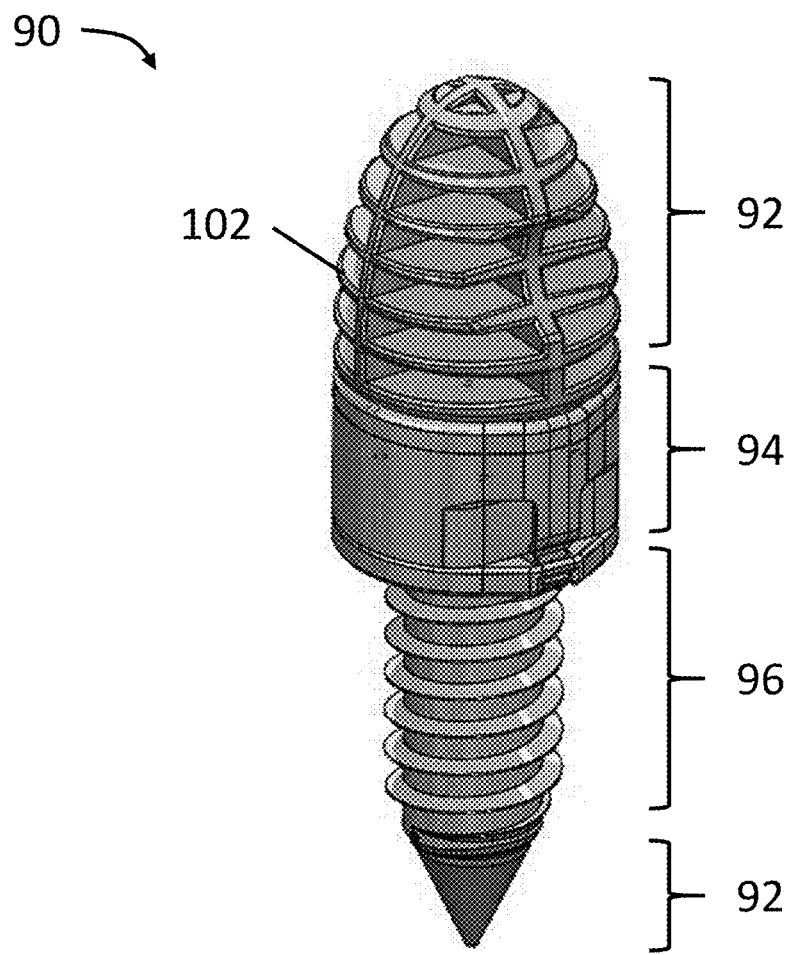
FIG. 4 illustrates a perspective view of a cannula assembly, according to aspects of the present embodiments.

FIG. 4 illustrates a perspective view of a cannula assembly 90, according to aspects of the present embodiments. Generally, the cannula assembly 90 may include an obturator 92, a dam seal sub-assembly 94, and a cannula body 96. The dam seal sub-assembly may be coupled via dam release clips 114 (shown in FIG. 5) that may attach releasably to tabs 128 on the cannula body 96, such that the dam seal sub-assembly 94 and the cannula body 96 are coupled together. The obturator 92 may be inserted coaxially through both the cannula body 96 and the dam seal sub-assembly 94. In general, in some embodiments, the obturator may serve as a handle used to push and twist the cannula assembly into the incision site. A plurality of slats 102 on a proximal handle portion 100 of the obturator may aid in manually holding and manipulating the obturator during insertion of the cannula assembly, and may improve certain aspects of manufacturing the obturator.

Figure 5:
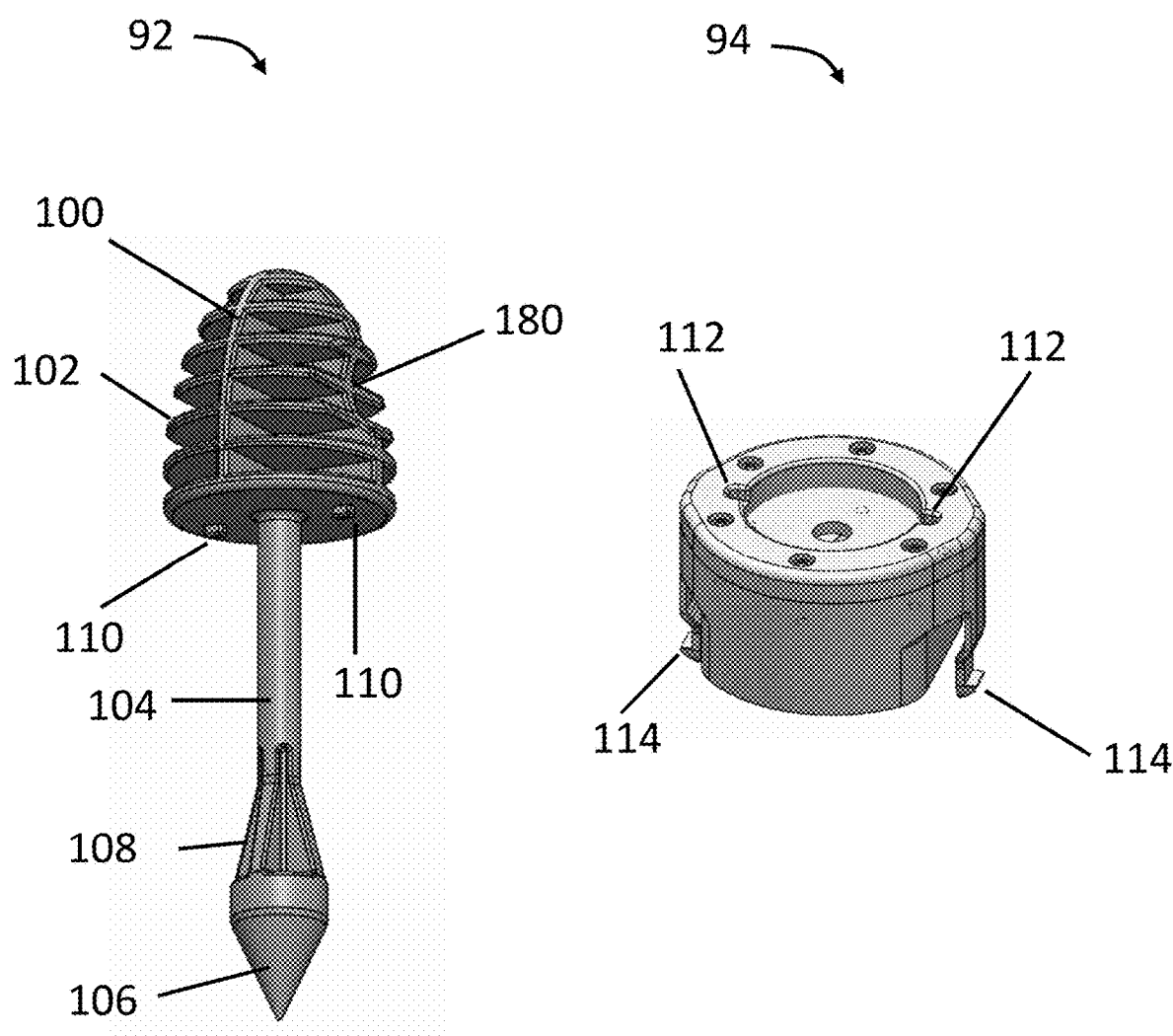
FIG. 5 illustrates a manner in which an obturator and a dam sub-assembly fit together, according to aspects of the present embodiments.
Figure 13:
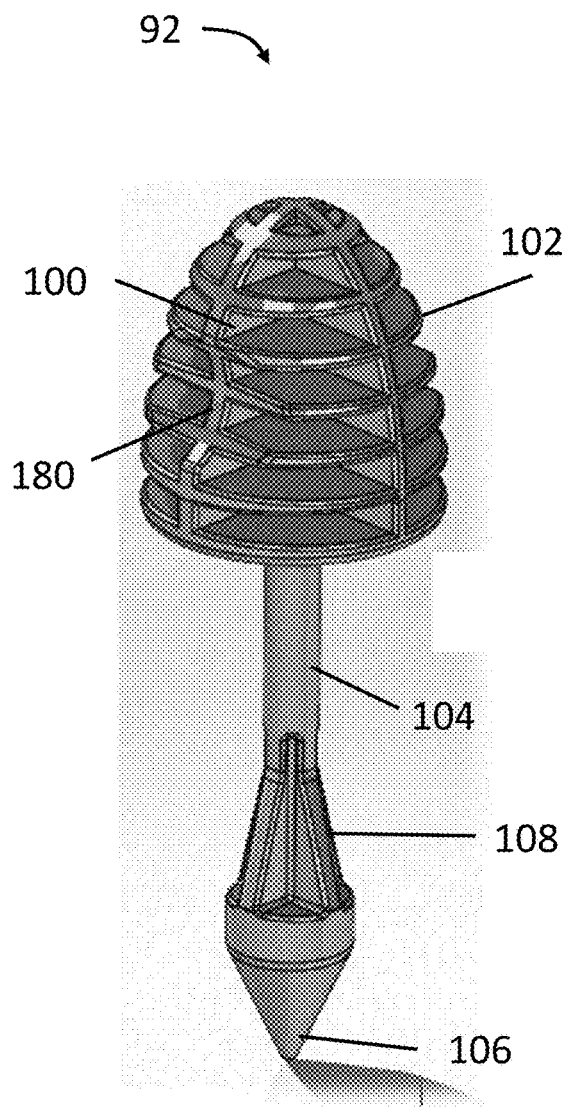
FIG. 13 illustrates a perspective view of an obturator, according to aspects of the present embodiments.

FIG. 5 illustrates a manner in which an obturator 92 and a dam seal sub-assembly 94 fit together, according to aspects of the present embodiments. Generally, the obturator may have two or more protruding rotation tabs 110 on a bottom surface of the proximal handle portion 100 that fit into two or more corresponding indentations 112 in a top portion of the dam seal sub-assembly 94. During the insertion of the cannula assembly, the rotation tabs 110 and indentations 112 may assist in the combined movement of the cannula assembly to enhance rotational movement of the cannula assembly while not restricting axial movement of the obturator 92 relative to the dam sub-assembly 94. Generally, the obturator comprises a proximal handle portion 100 shaped like a dome to fit an operator's hand, a distal conical tip 106 to help push the cannula assembly into a surgical incision, and a shaft portion 104 that connects the handle portion 100 and pointed portion 106. In some embodiments, a plurality of slats 102 on a proximal handle portion 100 of the obturator may aid in manually holding and manipulating the obturator during insertion of the cannula assembly, and may improve certain aspects of manufacturing the obturator. One or more concave portions 180 on the handle portion 100 may be present and may enhance manually holding and manipulating the obturator during certain methods. Certain aspects of the obturator 92 are also illustrated in FIG. 13 and described below.

Figure 6:
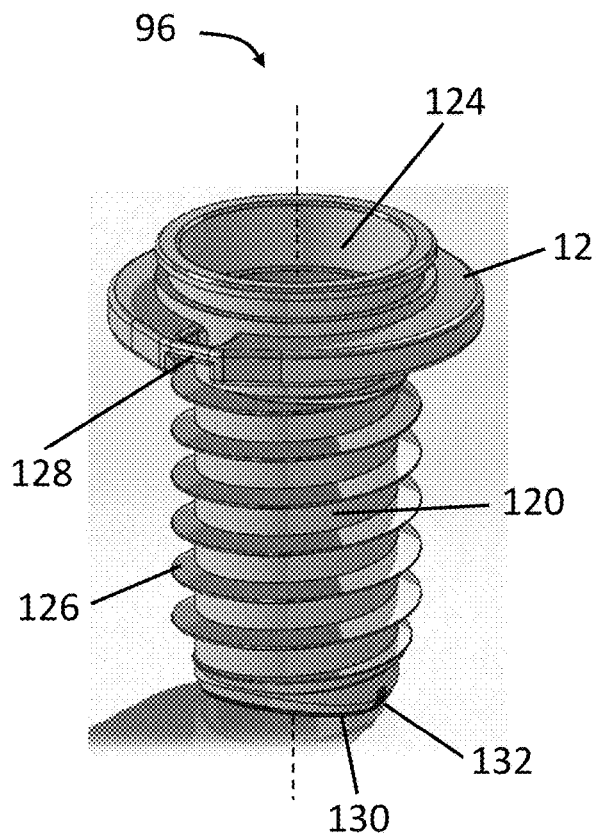
FIG. 6 illustrates a perspective view of a cannula body, according to aspects of the present embodiments.
Figure 7:
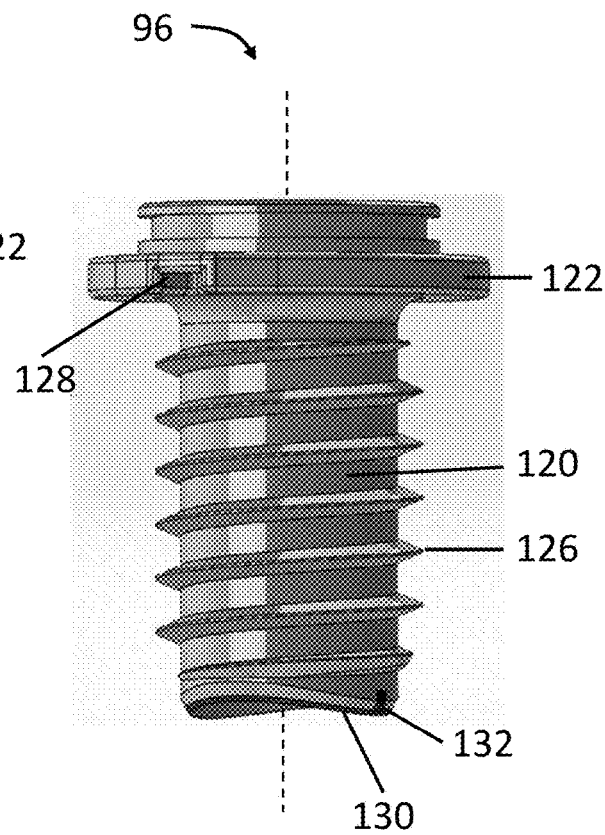
FIG. 7 illustrates a side view of a cannula body, according to aspects of the present embodiments.
Figure 8:
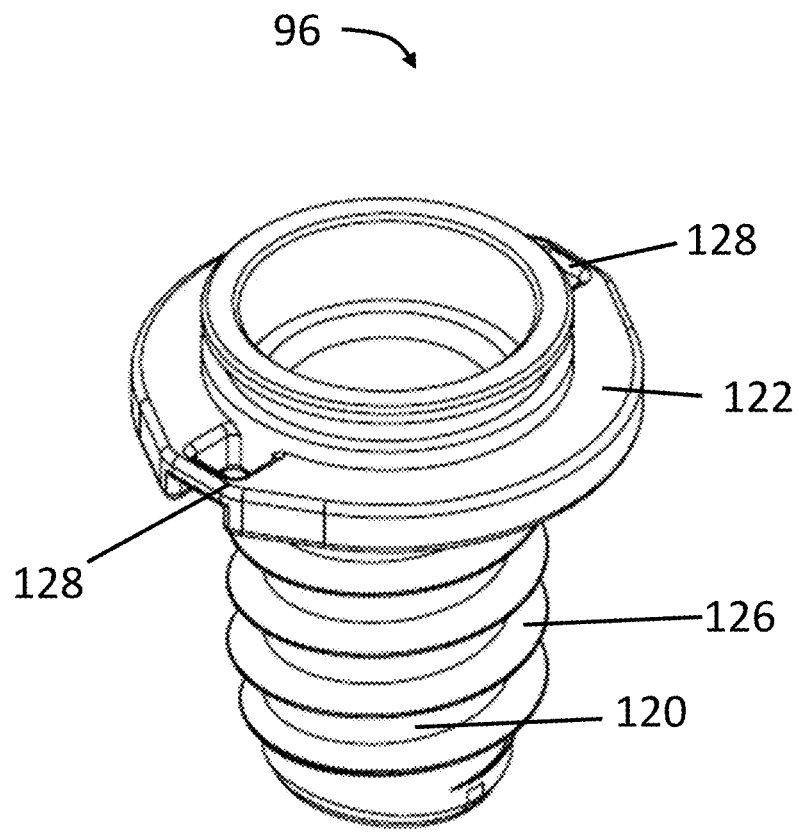
FIG. 8 illustrates a perspective view of a cannula body, according to aspects of the present embodiments.

FIG. 6 and FIG. 8 illustrate two different perspective views and FIG. 7 illustrates a side view of a cannula body 96, according to aspects of the present embodiments. The cannula body 96 may generally include a hollow cylinder 120 wrapped in a helical thread 126 along the entire length of the hollow cylinder 120. In some embodiments of the present disclosure and the present arthroscopic surgical methods, the thread around the cannula body may assist with gripping the incision site and allowing the surgeon to expand the internal volume at the surgical site. The cannula body 120 may also include a circular lip portion 122 near the proximal end of the hollow cylinder 120, on which two tabs 128 are positioned opposite each other. In some embodiments of the present disclosure, these tabs may be releasably interfaced with two corresponding dam release clips 114 on the dam seal sub-assembly so that the dam seal sub-assembly may be removed from or attached to the cannula body.

Referring still to FIG. 6 and FIG. 7, the distal end of the hollow cylinder 120 may terminate in a circumference 130 that is curved with respect to the plane perpendicular to the central axis of the hollow cylinder 120. This curved circumference 130 may be further outlined in a darkened line so that it may act as a visual guide for assessing the curvature of the surgical site. Depending on the diameter of the hollow cylinder 120, the degree of curvature of the curved circumference may change. Further, at least two additional visual markings 132 along the darkened line of the circumference may be applied at opposite locations and may assist as visual markers. In some embodiments, the visual markings 132 may extend proximally from the curved circumference 130 at the distal end of the hollow cylinder 120 from about 0.1 mm to about 10 mm, or from about 0.1 mm to about 0.5 mm, or from about 0.1 mm to about 1.0 mm, or from about 0.1 mm to about 0.8 mm, or from about 0.1 mm to about 0.5 mm, or from about 0.2 mm to about 1.0 mm, or from about 0.2 mm to about 0.8 mm, and/or from about 0.2 mm to about 0.5 mm.

In some embodiments, the cannula body 96 may comprise a translucent polycarbonate material. The translucent material may improve optical viewing of a surgical site through the cannula body 96 during a surgical procedure. In some embodiments, the cannula body 96 may comprise or be composed of a plastic, polymer, metal, or composite or hybrid material.

Figure 9:
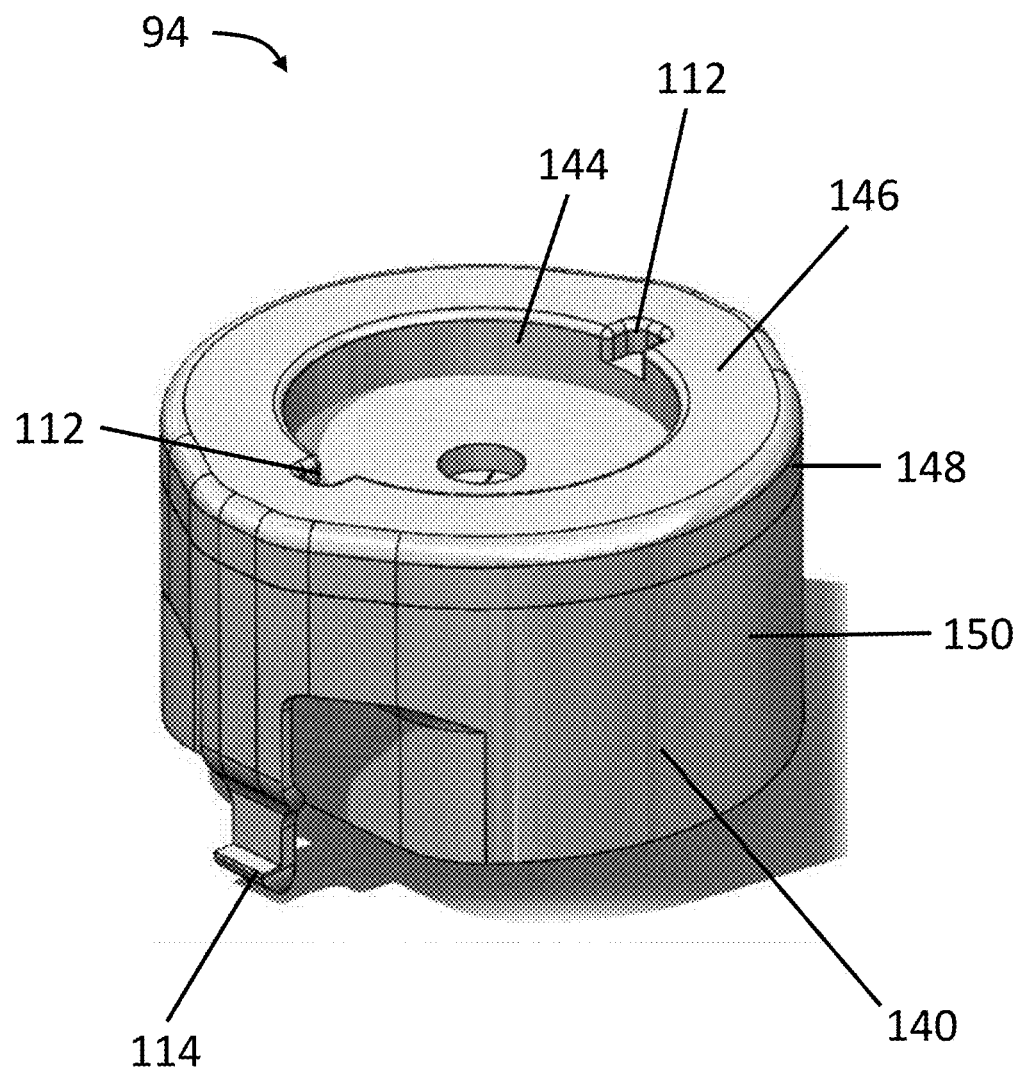
FIG. 9 illustrates a perspective view of a dam seal sub-assembly, according to aspects of the present embodiments.

FIG. 9 illustrates a perspective view of a dam seal sub-assembly, according to aspects of the present embodiments. In general, the dam seal sub-assembly may include one or more dam seals 154, 156, 158 (shown in FIGS. 10-12) enclosed within one or more outer pieces 148, 150, and may serve to form a flexible interface through which various arthroscopic surgery tools may enter into the cannula and interact at the surgical site, and which may serve to retain liquids, fluids, tissues, or other materials. The outer pieces 148, 150 may include a dam top piece 148 and a dam bottom piece 150, which are shown in more detail in FIG. 10 and described below. The damn top piece 148 may comprise a flat top surface 146 and a circular hole 144, and indentations 112 disposed at opposite positions on the circumference of the circular hole 144 (for example, approximately 180 degrees apart). The indentations 112 may couple with rotation tabs 110 on the obturator 92 (shown above in FIG. 5).

Figure 10:
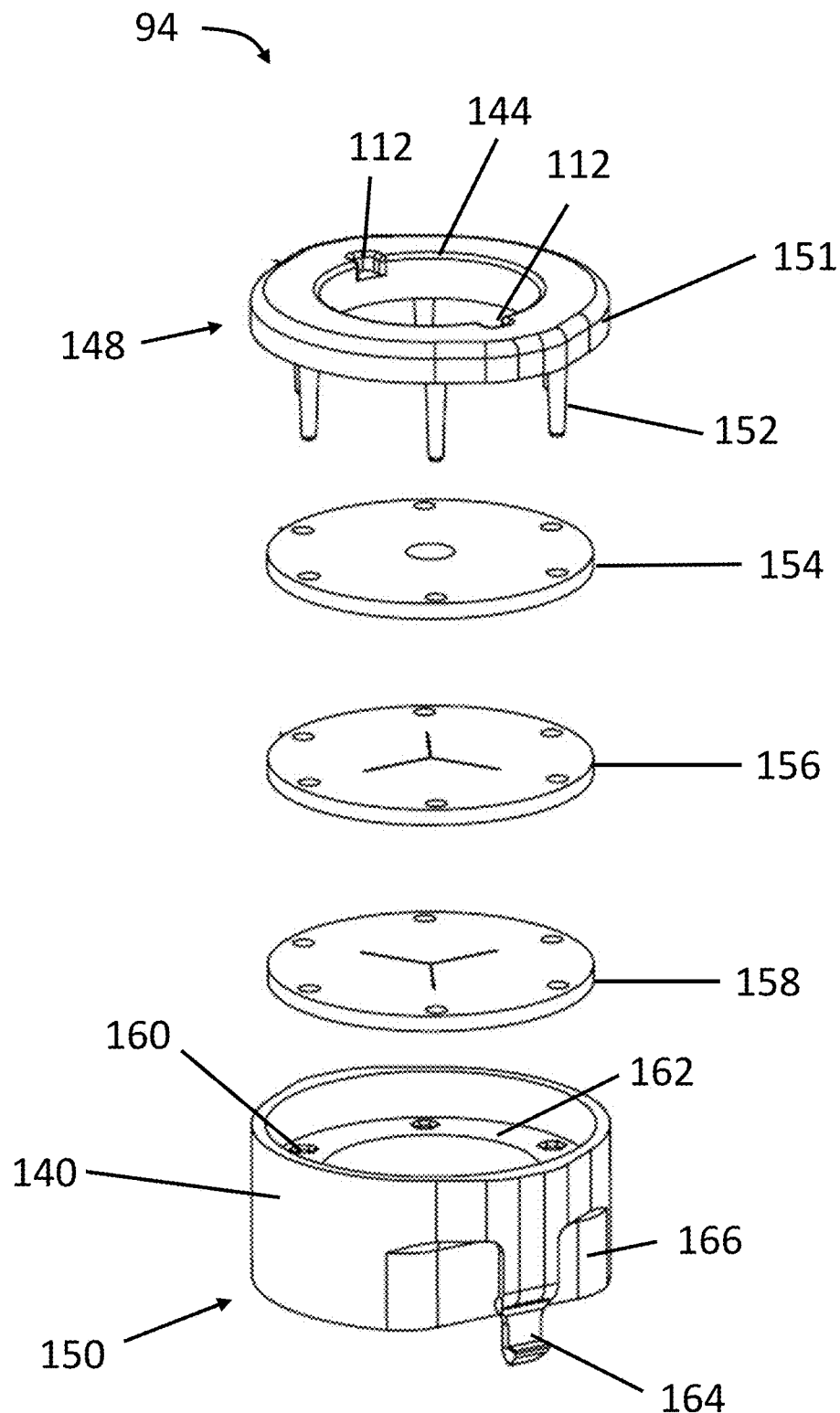
FIG. 10 illustrates a perspective exploded view of components of a dam seal sub-assembly, according to aspects of the present embodiments.

FIG. 10 illustrates a perspective exploded view of components of a dam seal sub-assembly 94, according to aspects of the present embodiments. The dam seal sub-assembly 94 may generally include a dam top piece 148, at least one dam seal pieces 158, 154, 156, and a dam bottom piece 150. In some embodiments, all the components illustrated in FIG. 10 fit together coaxially, or are longitudinally or axially aligned, and stacked parallel to each other. In general, the dam top piece 148 and dam bottom piece 150 may enclose the dam seal pieces 158, 154, 156 to form a flexible dam seal assembly that may enable various arthroscopic surgical tools to be inserted into the cannula to perform surgical procedures while maintaining the fluid (e.g., sterile saline solution, sterile fluid, and other materials within the surgical site.

In some embodiments, the dam top piece 148 and dam bottom piece 150 may comprise acrylonitrile butadiene styrene (ABS) or other similar polymeric or plastic materials.

Referring still to FIG. 10, the top dam seal piece 148 comprises a flat circular portion 151 with a circular hole in the center 154. The top dam seal piece 148 may further include multiple legs 152 protruding perpendicularly down from a bottom surface of the top dam seal piece 148. The legs 152 comprise tapered cylindrical rods. In some embodiments, the legs 152 are distributed evenly around the circumference of the top dam seal piece 148 (for example, 6 legs spaced approximately 60 degrees apart or 4 legs spaced approximately 90 degrees apart). The top dam seal piece further may include two or more indentations 112 positioned at the edge of the circular center hole 154 at opposite locations (for example, spaced 180 degrees apart), and may couple with corresponding rotation tabs 110 in the obturator 92.

Figure 11:
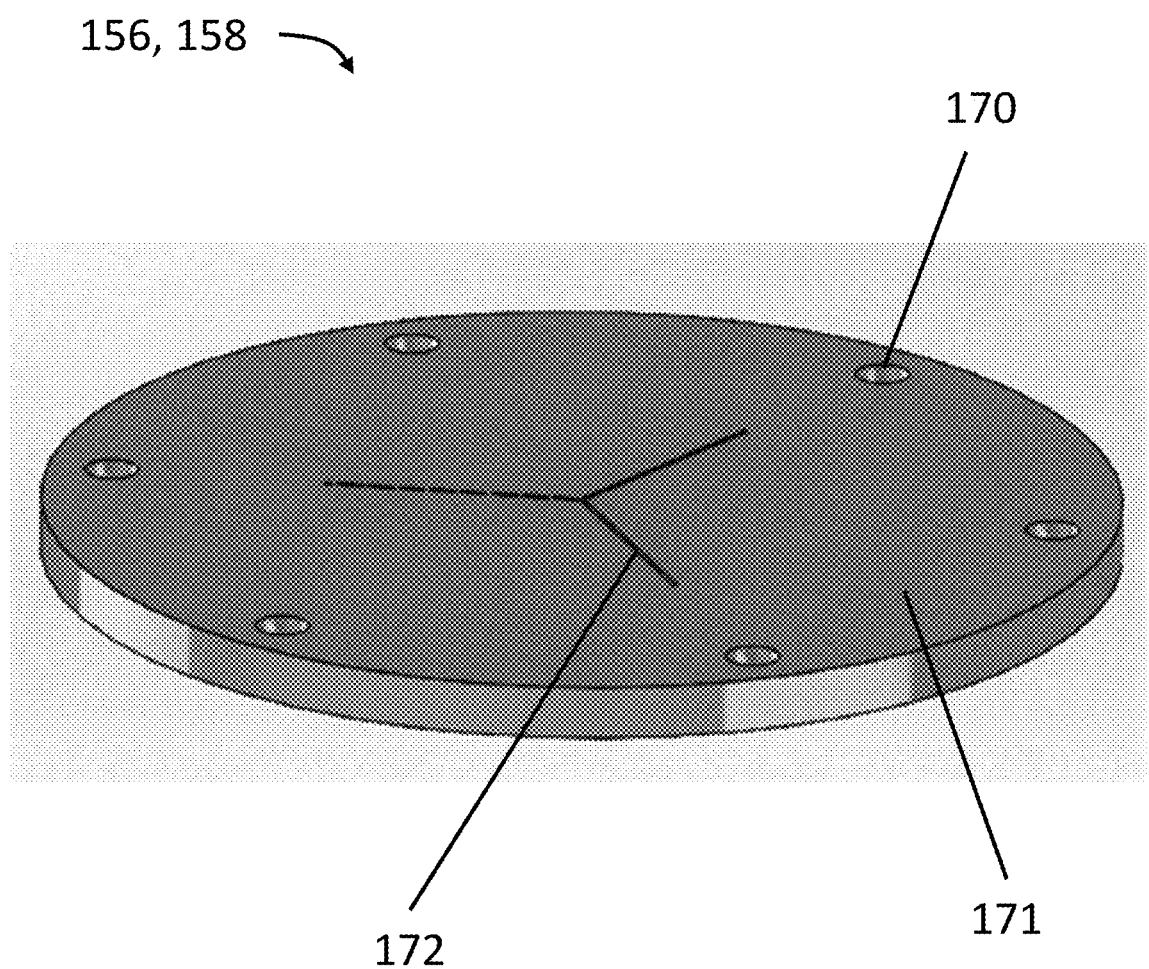
FIG. 11 illustrates a perspective view of a dam seal with slits, according to aspects of the present embodiments.
Figure 12:
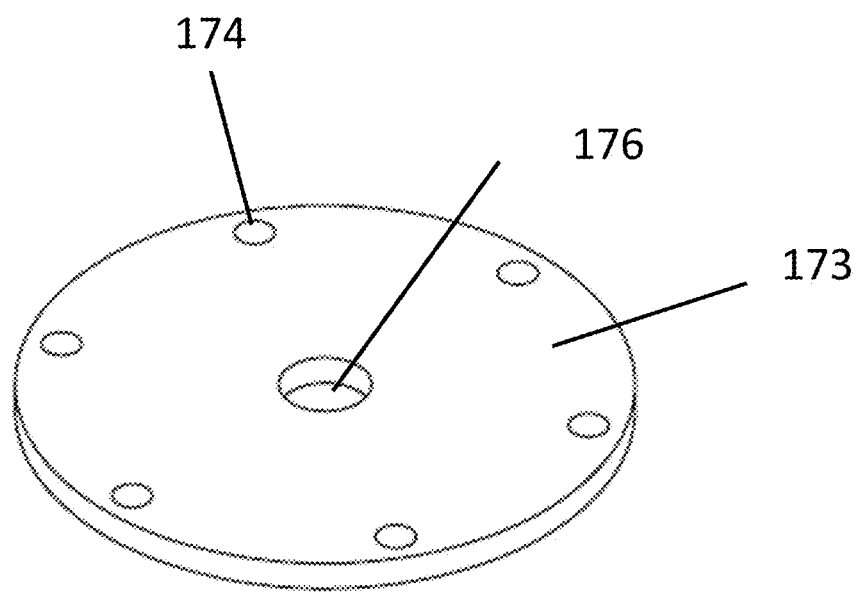
FIG. 12 illustrates perspective view of a dam seal with hole, according to aspects of the present embodiments.

FIG. 11 illustrates a perspective view of a dam seal with slits 156, 158, and FIG. 12 illustrates perspective view of a dam seal with hole 154, according to aspects of the present embodiments. In general, one or more dam seals are stacked together coaxially to form a flexible dam seal. In some embodiments, the dam seals comprise silicone or ethylene propylene diene monomer rubber (EPDM rubber), or other flexible polymeric material. Both the dam seal with slits 156, 158 and dam seal with hole 154 may also include multiple small circular holes 170, 174 disposed near the circumference of the discs that correspond to the legs 152 of the top dam seal piece 148. In some embodiments, the legs 152 may pass through the holes 170, 174 when the dam seal pieces are stacked coaxially.

Referring to FIG. 11, the dam seal with slits 156, 158 shown in FIG. 11 may comprise a circular disc, and may feature three or more slits cut in the disc running from the center toward the outer edge and angled equally from each other. In some embodiments, there may be three slits 172 separated by about 120 degrees. Referring to FIG. 12, the dam seal with hole 154 shown in FIG. 12 may comprise a circular disc, and may feature a small circular hole in the center of the disc.

Referring still to FIGS. 9-12, each of the dam seal pieces 154, 156, 158 may include one or more slits 172 or zero to one central holes 176 disposed therethrough to allow the obturator 92 to be pushed through the center of each of the dam seal pieces 154, 156, 158. The slits 172 bend downward (i.e., distally) as the obturator 92 is pushed through. As the obturator is removed from the dam assembly 94, each of the slits 172 move back to their original positions (i.e., coplanar with the rest of the respective dam seal piece 154, 156, 158). In the embodiment illustrated in FIG. 10, two of the three dam seal pieces 156, 158 include three slits 172 each, the three slits being oriented about 120 degrees apart from one another with the slits 172 of one of the dam seal pieces 156 being rotated approximately 60 degrees from the slits 172 of another dam seal piece 158, in order to minimize leakage through the dam assembly when the obturator 92 is withdrawn. The third dam seal piece 154 may include a hole 176 disposed therethrough to help keep the obturator 92 centered within the dam assembly 94. Each of the dam seal pieces 154, 156, 158 may be composed of a polymer material that has sufficient flexibility and elasticity, and that also includes a degree of shape memory.

Figure 14:
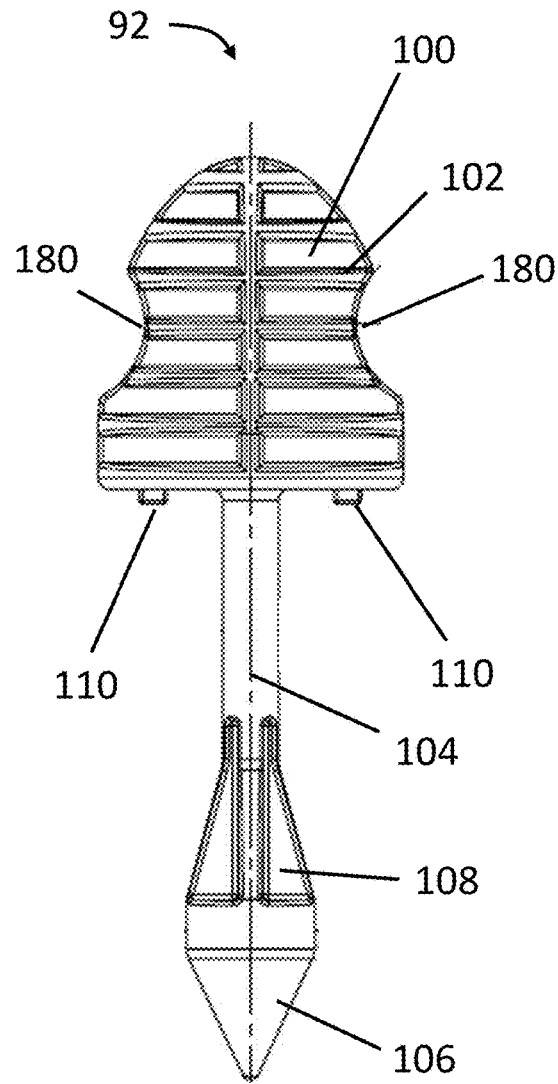
FIG. 14 illustrates a side view of an obturator, according to aspects of the present embodiments.

FIG. 13 illustrates a perspective view and FIG. 14 illustrates a side view of an obturator, according to aspects of the present embodiments. Generally, the obturator comprises a proximal handle portion 100 shaped like a dome to fit an operator's hand, a distal conical tip 106 to help push the cannula assembly into a surgical incision, and a shaft portion 104 that connects the handle portion 100 and pointed portion 106. In some embodiments, a plurality of slats 102 on a proximal handle portion 100 of the obturator may aid in manually holding and manipulating the obturator during insertion of the cannula assembly, and may improve certain aspects of manufacturing the obturator. For example, each of the slats 102 and vertical members bridging the gaps between slats 102 may have consistent thicknesses such that they may be produced via a molding process (i.e., an injection molding process that uses coring) where the heating and cooling processes during manufacturing result in consistent thermal and/or heat treat properties throughout the obturator 92 (thereby reducing material property variation in the resulting part).

Figure 15:
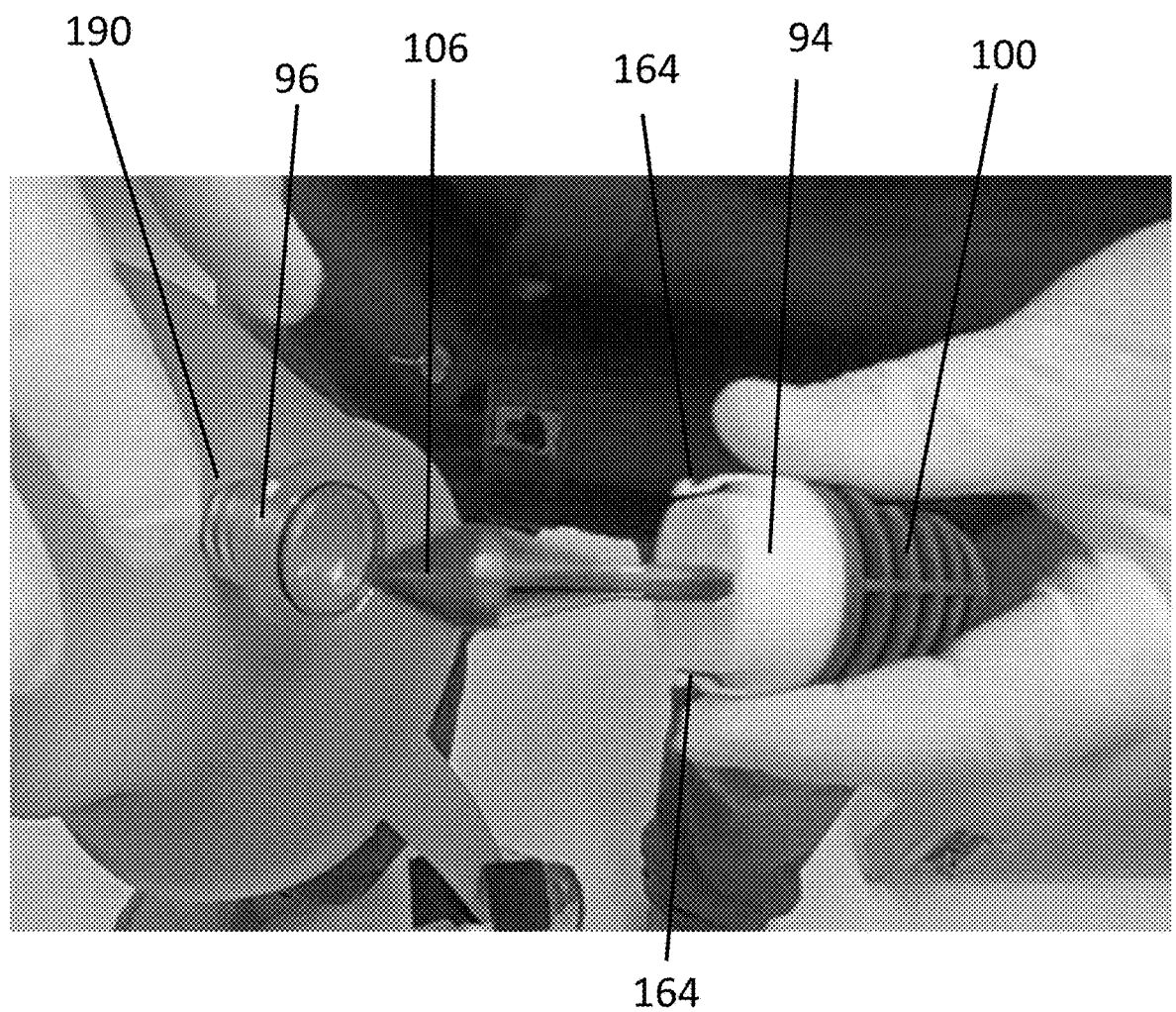
FIG. 15 illustrates a view of an obturator and a dam seal sub-assembly positioned near a cannula inserted into an incision at a joint, according to aspects of the present embodiments.

FIG. 15 illustrates a view of an obturator 100 and a dam seal sub-assembly 94 positioned near a cannula body 96 inserted into an incision 190 at a joint, according to aspects of the present embodiments. The obturator 100 is inserted through dam seal sub-assembly 94 such that they can be manipulated together as a combined object. The conical distal end 106 of the obturator is pointed toward the opening of the cannula body 96. The dam release clips 164 may be used to engage releasably with the corresponding tabs on the cannula body 96. The cannula body 96 is shown in FIG. 15 to be made of a transparent polymeric material to facilitate improved visibility within the surgical site.

In some embodiments, an adjustable arthroscopic measurement device or arthroscopic measurement probe is used to assess dimensions and shapes of at least one lesion or defect in cartilage at a surgical site.

Figure 16:
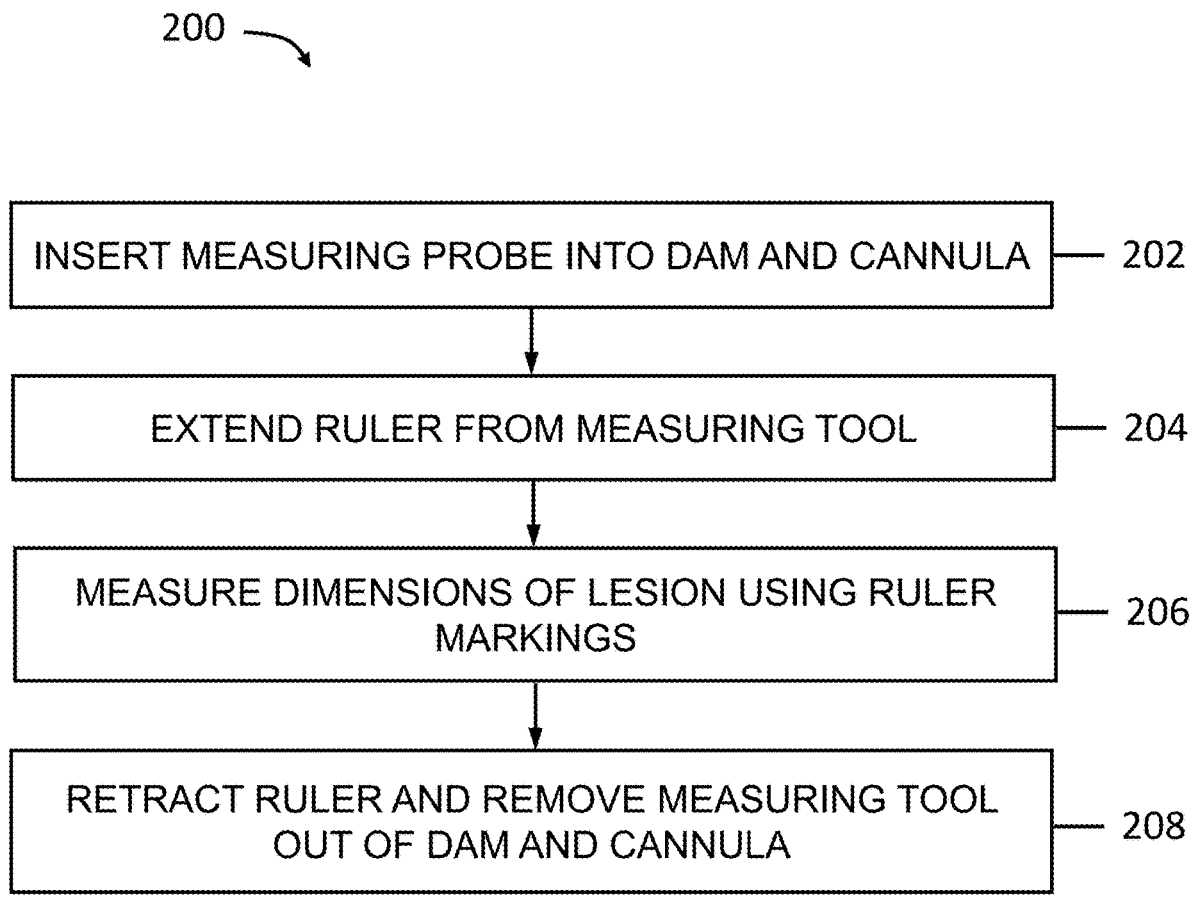
FIG. 16 illustrates a schematic of a method of using an arthroscopic measurement probe, according to aspects of the present embodiments.

FIG. 16 illustrates a schematic of a method 200 of using an arthroscopic measurement probe 210, according to aspects of the present embodiments. The method 200 may generally include inserting the measurement probe 210 into a dam seal sub-assembly 94 and cannula body 96 (step 202). A flexible ruler 218 may be extended from the measurement probe near the lesion or defect (step 204). The dimensions and shape of the lesion or defect may be measured by visual comparison to regular markings on the ruler 218 (step 206).

The adjustable nature of the measurement probe 210 may allow the ruler 218 to be rotated and extended or retracted to better align the ruler 218 with various features of the lesion or defect. Once the measurement is complete, the ruler 218 may be retracted into the measurement probe 210, may be removed from the surgical site, and may be retracted out of the dam seal sub-assembly and cannula body (step 208).

Figure 17:
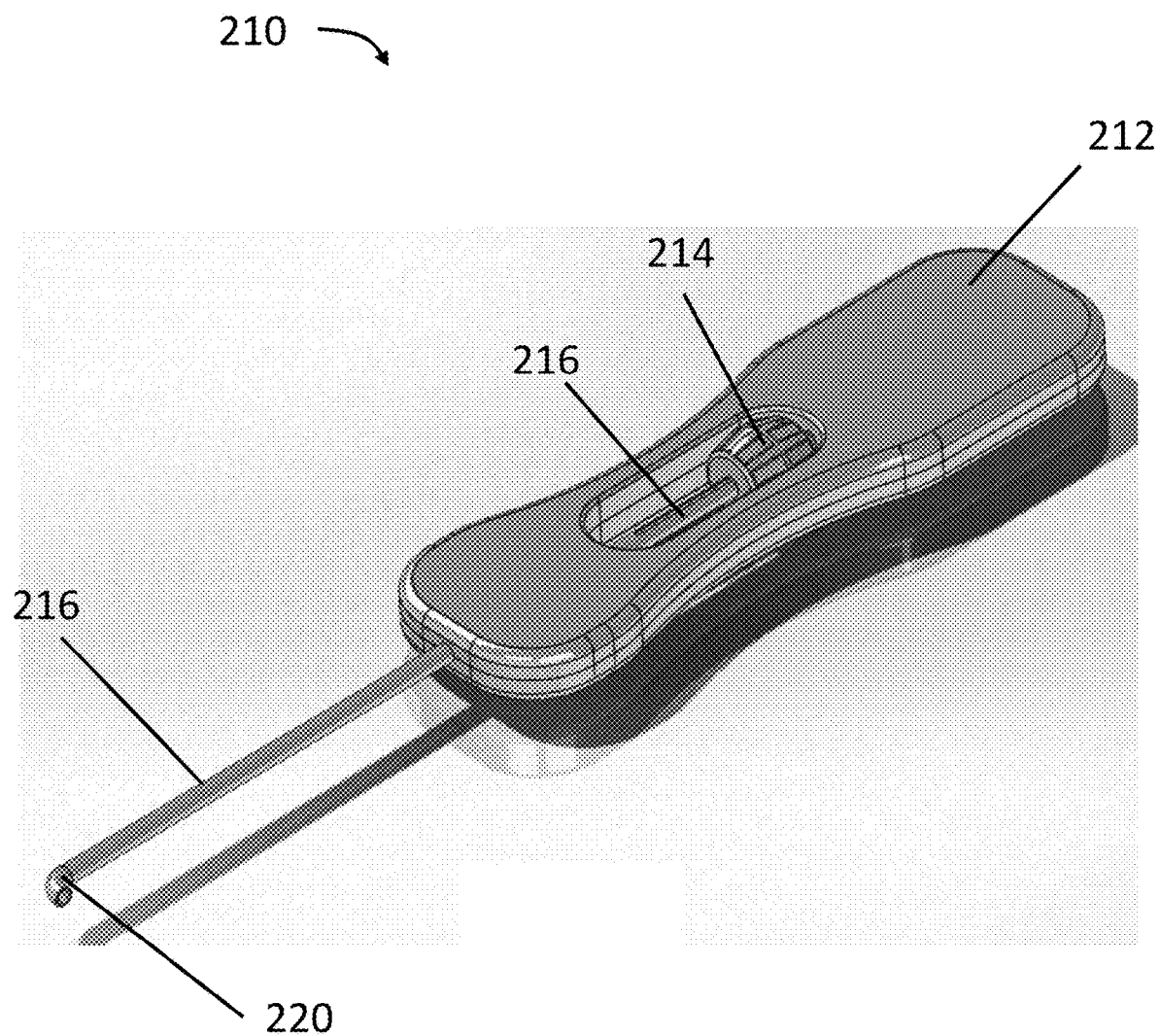
FIG. 17 illustrates a perspective view of an arthroscopic measurement probe assembly, according to aspects of the present embodiments.
Figure 18:
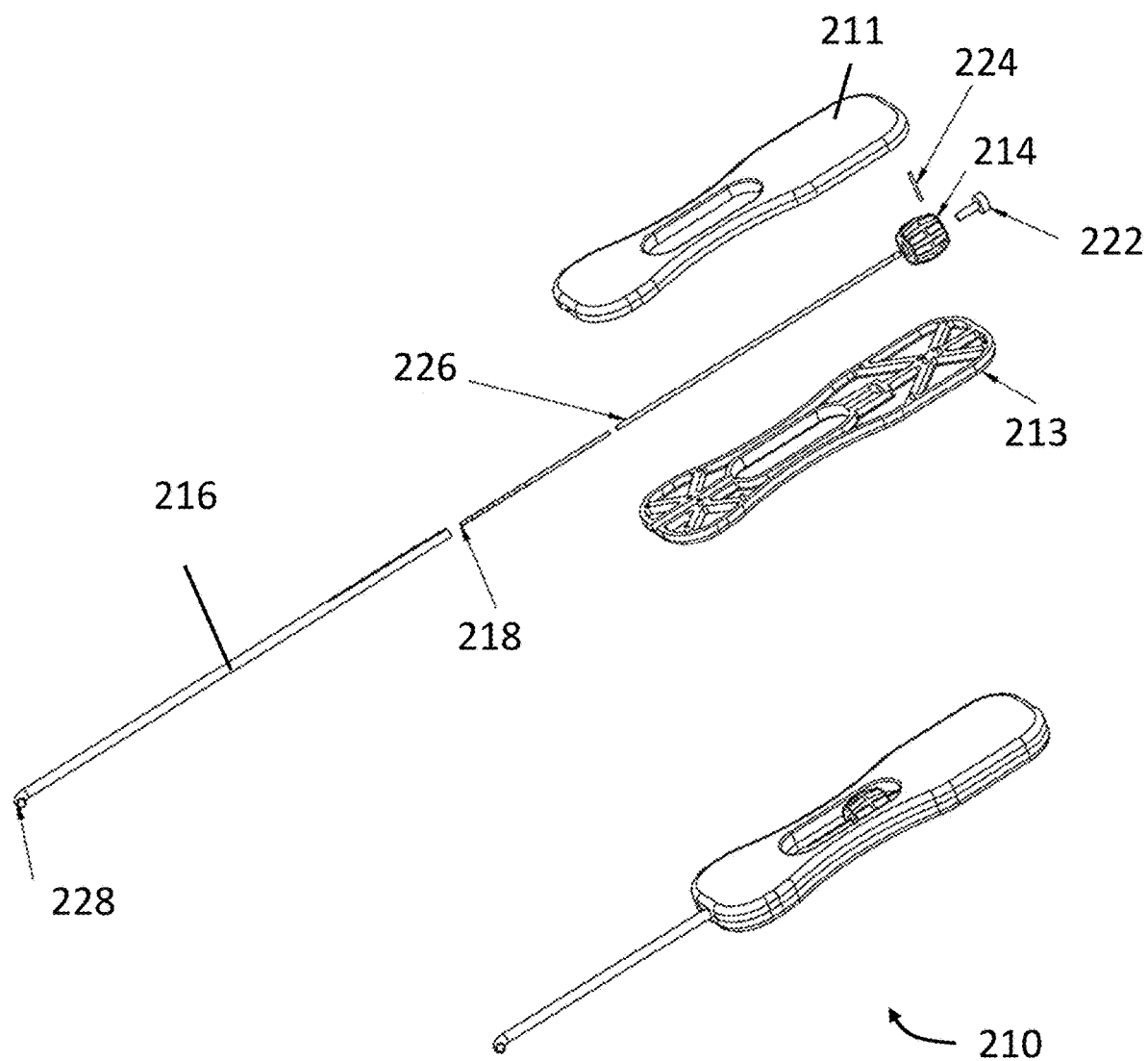
FIG. 18 illustrates a perspective exploded view of parts of an arthroscopic measurement probe assembly, according to aspects of the present embodiments.

FIGS. 17 and 18 illustrate perspective views of an arthroscopic measurement probe assembly 210, according to aspects of the present embodiments. Generally, the measurement probe 210 may include a handle 212, an adjusting knob 214, a rotating plug 222, a dowel pin 224, a stroke arm 226, a sizer tube 216, and a flexible ruler 218. In some embodiments, the rotating plug 222, the adjusting knob 214, the stroke arm 226, the sizer tube 216, and the flexible ruler 218 are all connected coaxially such that the adjusting knob 214 may be used to extend the ruler 218 and rotate the sizer tube 216, and the flexible ruler 218 may be disposed through the interior of the sizer tube 216. In some embodiments, the distal end 220 of the sizer tube 216 may be bent such that there may be a curve angled at 90 degrees, or from 85 to 95 degrees, or from 75 to 105 degrees. In some embodiments, the radius of curvature of the bend at the distal end 220 of the sizer tube 216 may have a radius of curvature of about 0.11 inches, or from about 0.05 to 0.2 inches.

FIG. 18 illustrates a perspective exploded view of parts of an arthroscopic measurement probe assembly, according to aspects of the present embodiments. Generally, the handle 212 may comprise two pieces: a top shell piece 211 and a bottom shell piece 213. An adjusting knob 214 may be connected to a stroke arm 226 by a dowel pin 224 which may pass through a slit 236 disposed in the sizer tube 216. A dowel pin 222 may also be connected at the proximal end of the stroke arm 226 and adjusting knob 214. In some embodiments, the arrangement and connection of these components may enable pushing of the adjusting knob 214 along the longitudinal axis of the measurement probe device 210 to extend and retract the flexible ruler 218, and rotating of the adjusting knob 214 to rotate the sizer tube 216. The overall effect of these combined movements is that the flexible ruler 218 may be deployed at a variety of angles and positions within the surgical site to facilitate measurement of the lesions or defects.

In some embodiments, the top shell piece 211 and the bottom shell piece 213 of the handle 212 comprise acrylonitrile butadiene styrene (ABS) or other similar plastic or polymeric material, and may be held together via crush pins (for example, matching offset features such as a cylindrical protrusion in the top shell piece 211 interfacing with a corresponding octagonal sleeve in the bottom shell piece 213, or vice versa) thereby holding the two pieces 211, 213 together via friction.

Figure 19:
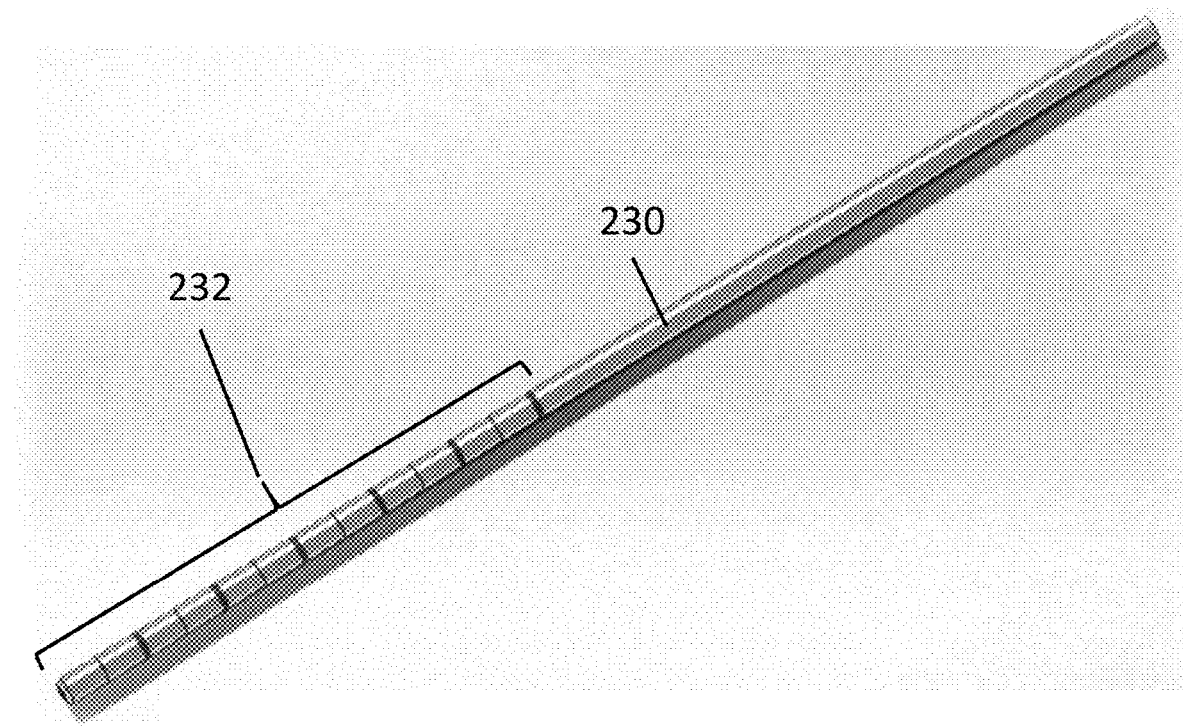
FIG. 19 illustrates a ruler for an arthroscopic measurement probe, according to aspects of the present embodiments.

FIG. 19 illustrates a flexible ruler 218 for an arthroscopic measurement probe 210, according to aspects of the present embodiments. Generally, the flexible ruler 218 comprises a cylindrical rod 230 comprising a flexible material that can bend and hold a shape. In some embodiments, the cylindrical rod 230 may comprise or be composed of one of polyether ether ketone (PEEK) or a metal wire or a polymer material or a combination of polymeric and metallic materials. The material or materials comprising the cylindrical rod 230 may enable a flexible ruler 218 that can bend through the bent opening 220 of the sizer tube 216, and maintain a substantially straight portion when extended for ease of measurement. The flexible ruler 218 may also have multiple markings 232 distributed along a length of an exterior surface of the cylindrical rod 230 near the distal end of the rod. The markings 232 comprise thin lines perpendicular to the longitudinal axis of the cylindrical rod 230 and may be separated by spacings of 2.5 mm and 5.0 mm. In some embodiments, the markings 232 may be imprinted on the ruler 218 by one or more methods including laser etching, physical etching, screen printing, and/or ink marking.

Figure 20:
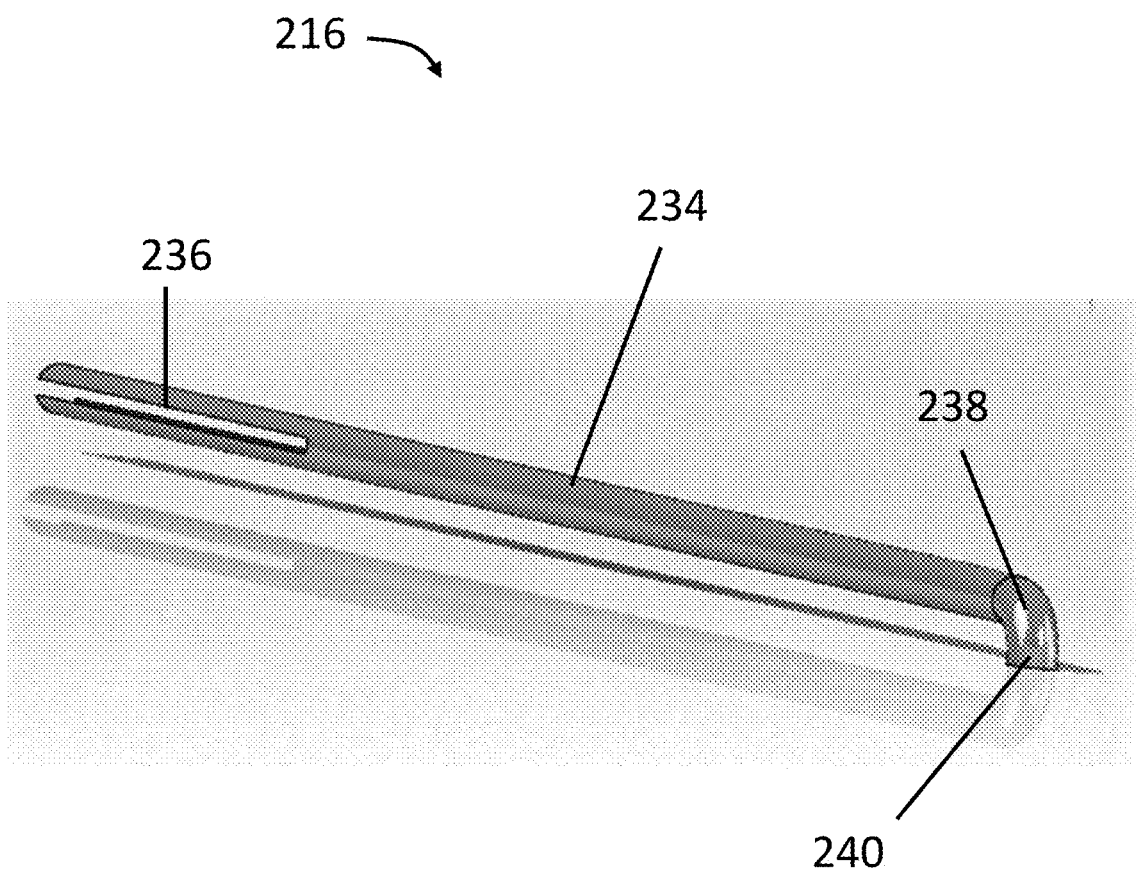
FIG. 20 illustrates a tube for an arthroscopic measurement probe, according to aspects of the present embodiments.

FIG. 20 illustrates a sizer tube 216 for an arthroscopic measurement probe 210, according to aspects of the present embodiments. Generally, the sizer tube 216 comprises a hollow cylindrical tube 234 that has two slits 236 disposed at its proximal end at opposite locations. The sizer tube 216 may also include a bend 238 at the distal end of the tube so that the opening of the tube 240 points at an angle away from the longitudinal axis of the tube (to allow for measurement of surfaces that are roughly orthogonal to the axial or longitudinal direction). In some embodiments, this angle may be about 90 degrees. In some embodiments, this angle may be from about 75 degrees to about 105 degrees. In some embodiments, the radius of curvature of the bend 238 may be about 0.11 inches. In some embodiments, the radius of curvature of the bend 238 may be from about 0.05 inches to about 0.25 inches. In some embodiments, the sizer tube 216 may comprise at least one of stainless steel T304, stainless steel T316, or fractional hypodermic tubing.

Figure 21:
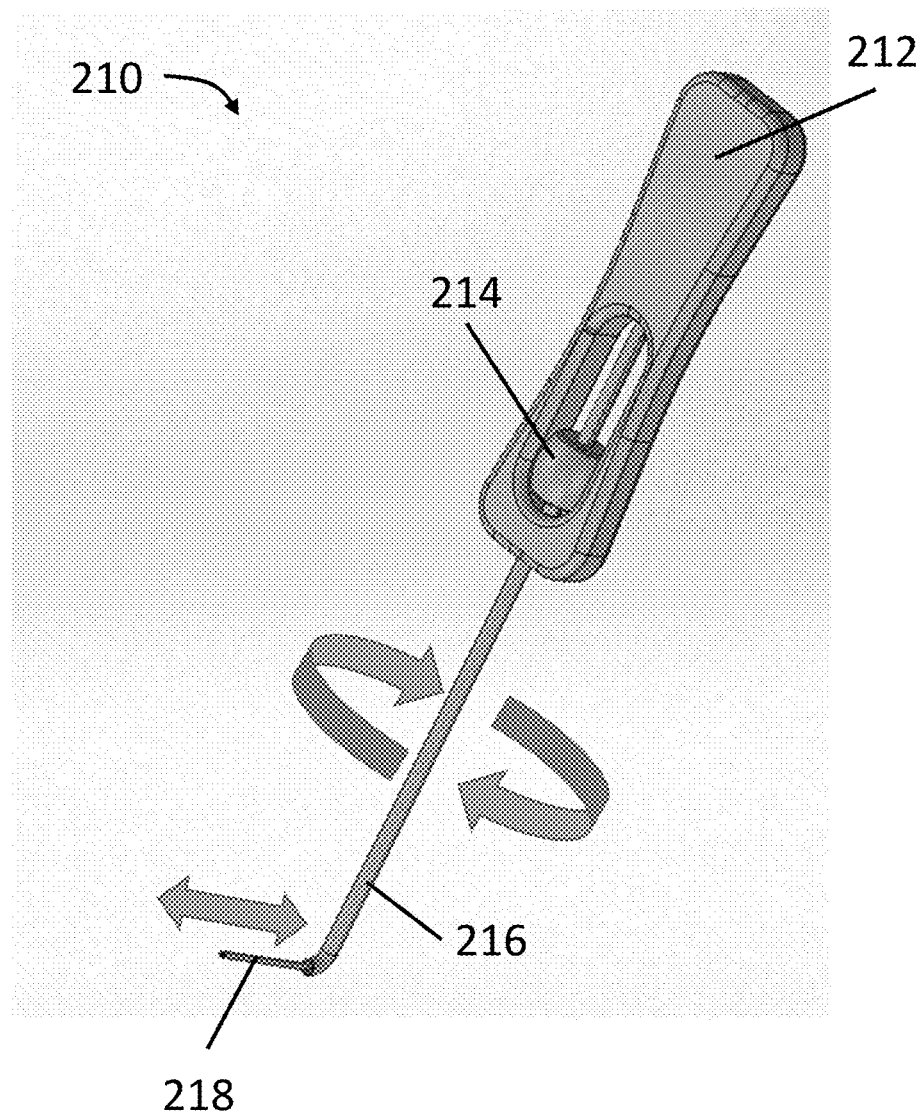
FIG. 21 illustrates a perspective view of an arthroscopic measurement probe assembly with arrows indicating movements and showing an extended ruler, according to aspects of the present embodiments.

FIG. 21 illustrates a perspective view of an arthroscopic measurement probe 210 assembly with arrows indicating movements and showing an extended ruler 218, according to aspects of the present embodiments. The handle 212, adjusting knob 214, sizer tube 216, and flexible ruler 218 are shown, and are as described above. The adjusting knob 214 is shown here in its furthest extended position, closer to the distal end of the handle. Correspondingly, the ruler 218 is shown fully extended out of the sizer tube. The straight, double-ended arrow indicates the capability of the ruler 218 to be extended and retracted. The curved arrows indicate the capability of the sizer 216 tube to be rotated along its longitudinal axis, such that the extended ruler 218 may point along different directions.

In the present disclosures, multiple cutting tools are described. Each of the tools may have one or more surgically sharp cutting edges, which may be machined or manufactured to have sufficiently sharp break edge to readily make sharp cuts in biological materials that may include skin, cartilage, and/or bone. For example, in some embodiments, cutting edges may include a break edge of 0.002 inches, 0.001 inches, or less than 0.001 inches, as well as various sub-ranges therebetween.

Figure 22:
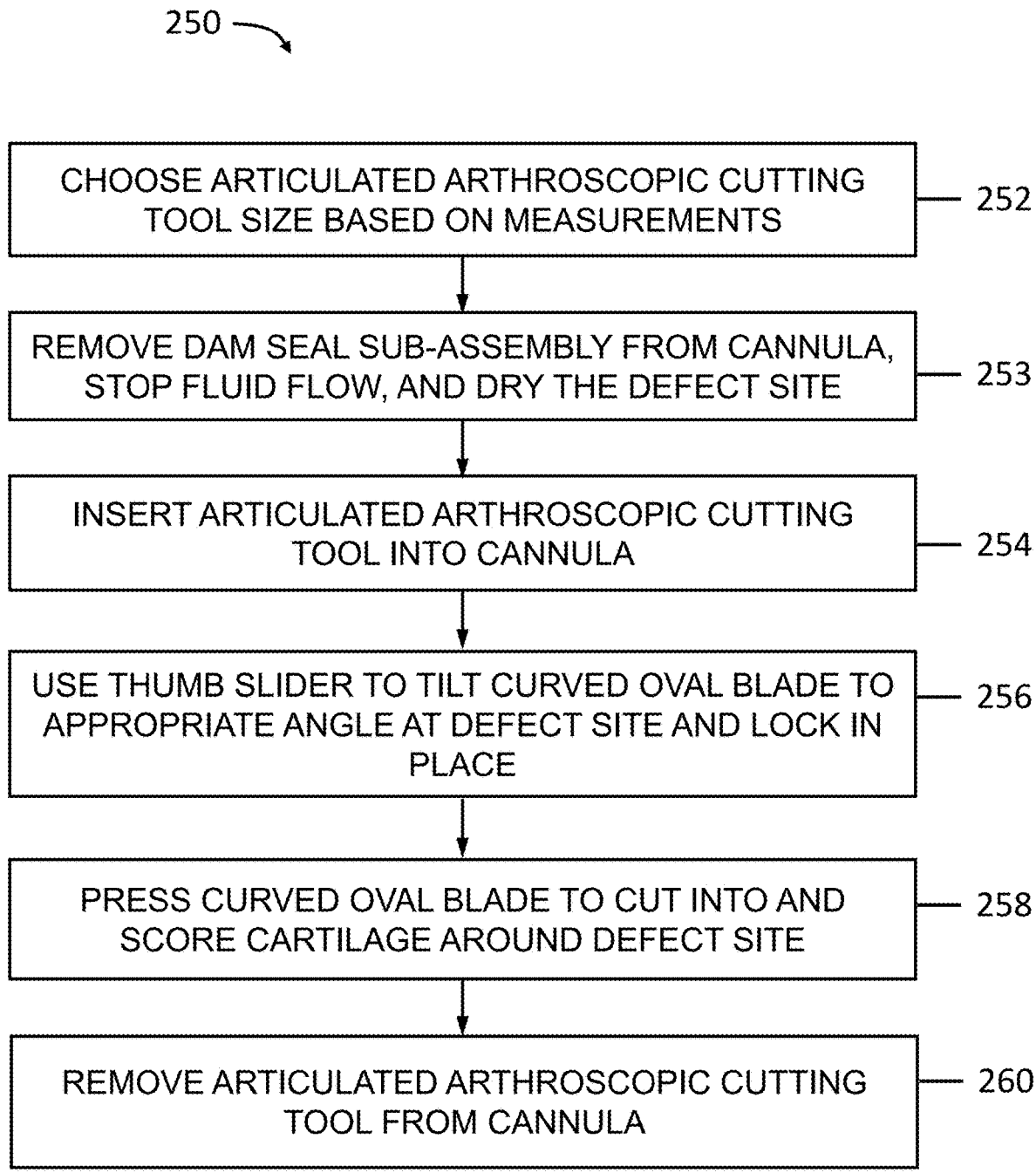
FIG. 22 illustrates a schematic of a method to use an articulated arthroscopic cutting tool during an arthroscopic surgical procedure, according to aspects of the present embodiments.

FIG. 22 illustrates a schematic of a method 250 to use an articulated arthroscopic cutting tool 270 during an arthroscopic surgical procedure, according to aspects of the present embodiments. Generally, the method 250 includes choosing a size of articulated arthroscopic cutting tool 270 based on measurements taken using the above method 200 of measuring dimensions of defects or lesions in cartilage (step 252); removing a dam seal sub-assembly from a cannula, stopping fluid flow, and drying a defect site (step 253); inserting an articulated arthroscopic cutting tool 270 into a cannula 96 and dam seal sub-assembly 94 at a surgical site (step 254); using a thumb slider 274 on a handle 286 of the articulated arthroscopic cutting tool 270 to tilt a blade 278 on the cutting tool to an appropriate angle and locking the angle in place; pressing the blade 278 into cartilage 42 at a surgical site surrounding defects or lesions (step 258); and removing the articulated arthroscopic cutting tool 270 from the cannula 96 and dam seal sub-assembly 94 (step 260). Once inserted into the cannula, the articulated arthroscopic cutting tool 270 may be rotated from zero to 360 degrees (and sub-ranges therebetween) within the cannula 96 (for example, with the shaft 276 concentrically disposed within the cannula) In some embodiments, after the method 250 is completed, there may remain at least one oval outline 52 (shown in FIG. 2D) defined in cartilage corresponding to the shape of the blade 278. Further methods that may take place after the method 250 are described by method 330 and illustrated by FIG. 30.

Figure 23:
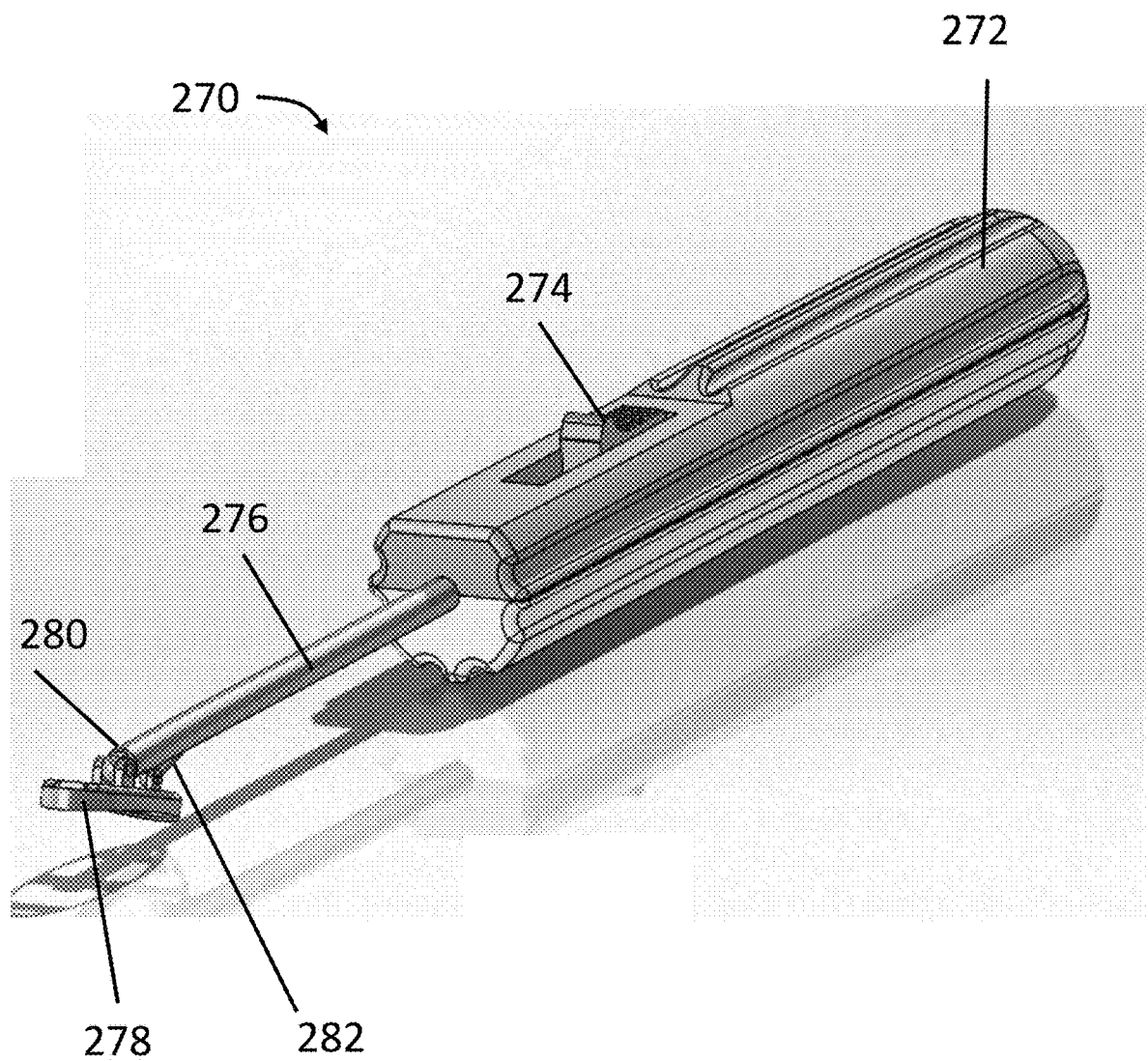
FIG. 23 illustrates a perspective view of an articulated arthroscopic cutting tool assembly, according to aspects of the present embodiments.

FIG. 23 illustrates a perspective view of an articulated arthroscopic cutting tool assembly 270, according to aspects of the present embodiments. In general, the articulated arthroscopic cutting tool assembly 270 includes a handle 272, a thumb slider 274, a linear stator shaft 276, a curved oval blade 278 connected by a hinged joint 280 to the linear stator shaft 276, a linear transmission shaft 292 connected to the thumb slider 274, and a linkage piece 282 connected to both the linear transmission shaft 292 and the curved oval blade 278. In some embodiments, the linkage piece 282 is connected to the curved oval blade 278 at a joint 284. In some embodiments, movement of the thumb slider 274 along the longitudinal axis of the handle causes the curved oval blade 278 to tilt about the joint 280 with respect to the linear stator shaft and with respect to the longitudinal axis of the articulated arthroscopic cutting tool 270. In some embodiments, the curvature of the oval blade 278 may allow it to follow a curved surface of a joint such as a medial femoral condyle, a lateral femoral condyle, a patella, or a trochlea of a subject or a patient.

Figure 24:
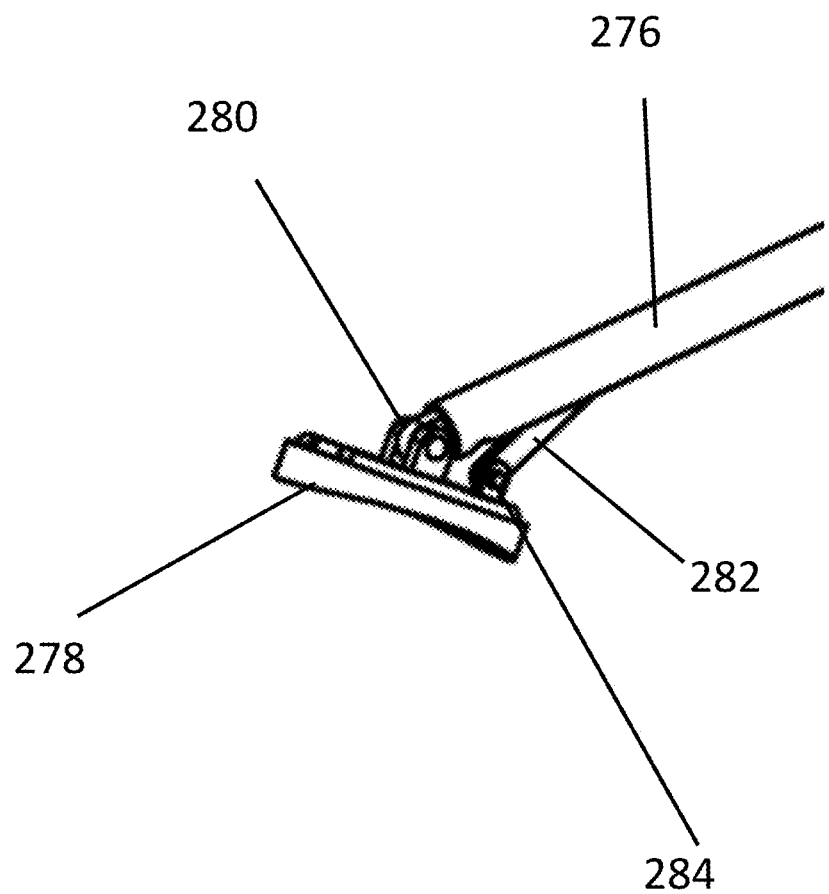
FIG. 24 illustrates a perspective view of the distal end of the articulated arthroscopic cutting tool assembly according to aspects of the present embodiments.

FIG. 24 illustrates a perspective view of the distal end of the articulated arthroscopic cutting tool assembly 270 according to aspects of the present embodiments. In general, because the linkage piece 282 is connected to both the linear transmission shaft 292 and the curved oval blade 278, movement of the thumb slider 274 causes the curved oval blade 278 to tilt about the axis at the joint 280, so that the angle of the curved oval blade 278 changes with respect to the longitudinal axis of the articulated arthroscopic cutting tool assembly 270.

Figure 25:
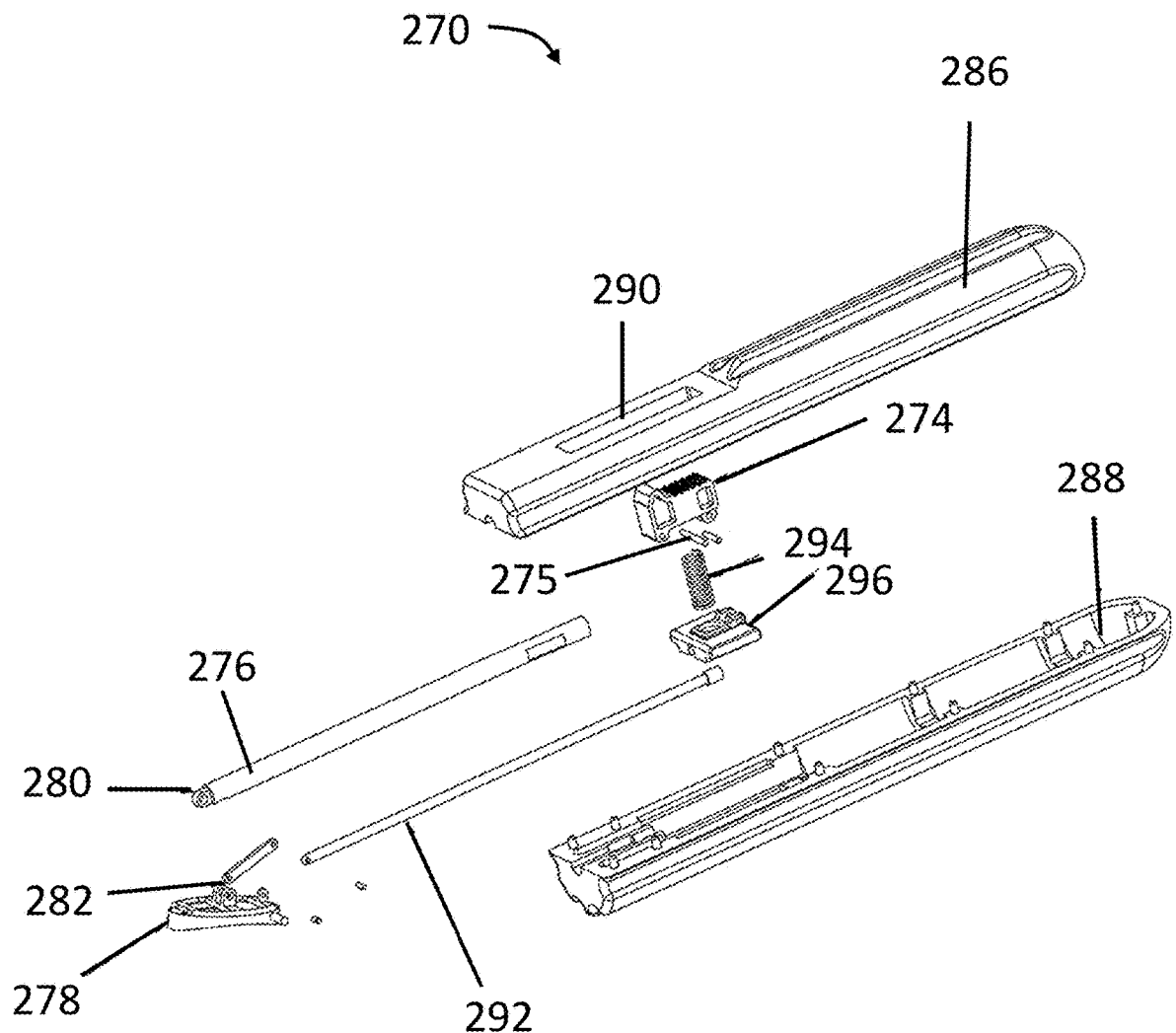
FIG. 25 illustrates a perspective exploded view of parts of an articulated arthroscopic cutting tool assembly, according to aspects of the present embodiments.

FIG. 25 illustrates a perspective exploded view of parts of an articulated arthroscopic cutting tool assembly 270, according to aspects of the present embodiments. In general, the handle comprises an upper shell 286 and a lower shell 288, which come together to form the handle. In some embodiments, the upper shell 286 comprises a ridged half-cylinder with a rectangular opening 290 that runs longitudinally along the ridged half-cylinder, while the lower shell 288 comprises a ridged half-cylinder. In some embodiments, when the two shells 286, 288 are closed together to form a full cylinder, there may be a small circular opening 298 at the distal end of the handle. In some embodiments, the ridges on the handle on the upper and lower shells 286, 288 run longitudinally along the length of the shells, and may provide improved gripping by a user or operator for the articulated arthroscopic cutting tool 270.

Still referring to FIG. 25, the articulated arthroscopic cutting tool assembly may also include a thumb slider that comprises a slider button 274, a slider clamp piece 296, and a spring 294 disposed perpendicularly between the slider button 274 and the slider clamp piece 296. The slider button 274 may comprise a raised top surface as the distal end of the button and a ridged top surface at the proximal end of the button. The interior surface (i.e., the underside) of the upper shell 286 may comprise a plurality of notches (not visible in the view of FIG. 25) disposed on either side of the rectangular opening 290 that may interface with a cylindrical pin 275 near the slider button 274 such that the slider button 274 may be locked at different positions along the rectangular opening 290 (i.e., by pushing down the slider button 274 (thereby compressing spring 294), sliding the slider button 274 to the desired position, and releasing the slider button 274 such that the pin 275 engages with the notches in the upper shell 286). This position locking mechanism may enable the curved oval blade 278 to be locked at different tilt angles with respect to the longitudinal axis of the articulated arthroscopic cutting tool 270.

Figure 26:
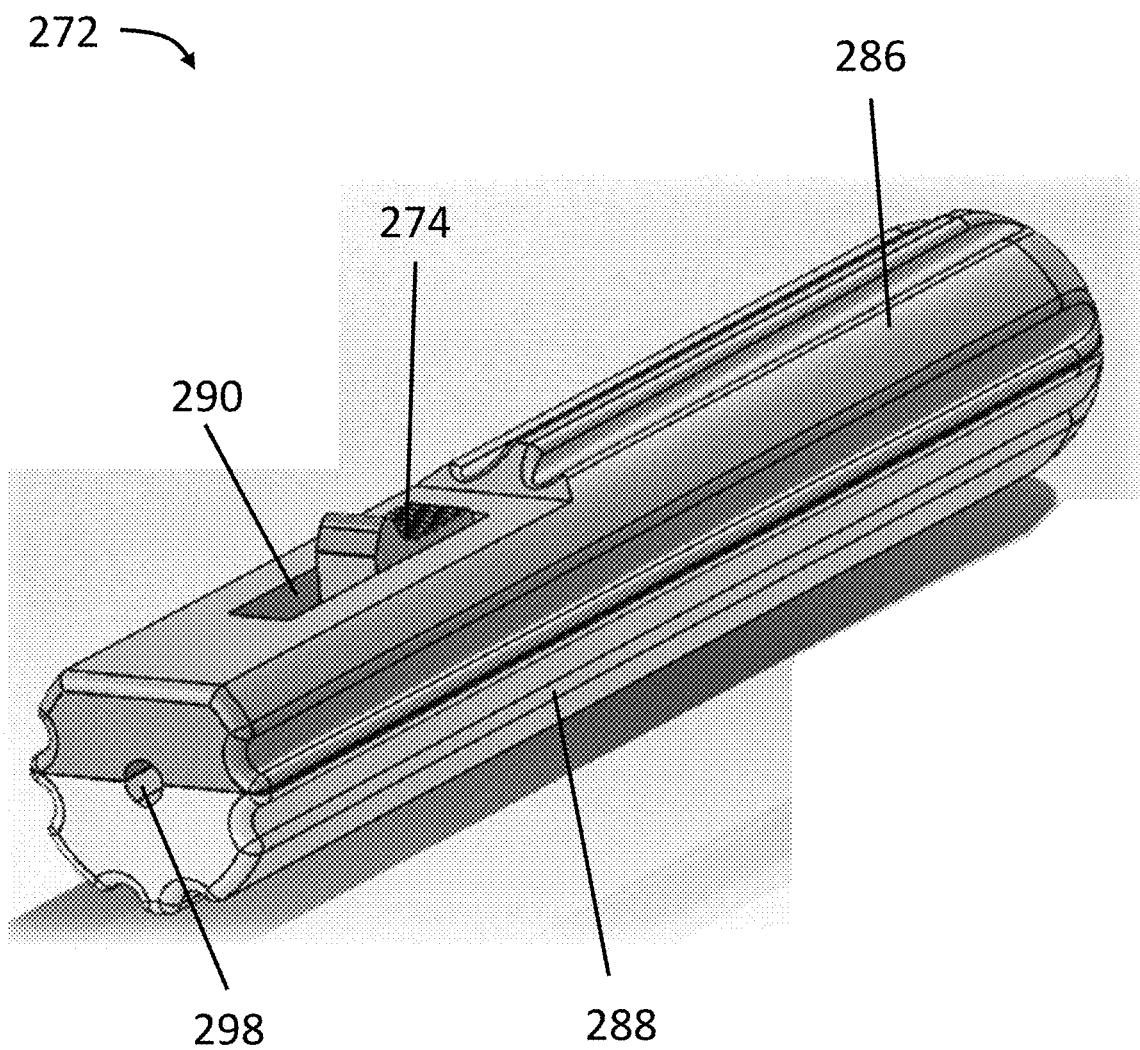
FIG. 26 illustrates a perspective view of a handle for an articulated arthroscopic cutting tool assembly according to aspects of the present embodiments.

FIG. 26 illustrates a perspective view of a handle 272 for an articulated arthroscopic cutting tool assembly according to aspects of the present embodiments. In general, the thumb button 274 protrudes slightly out of the rectangular opening 290 in the handle top shell 286. The circular hole 298 formed by top and bottom shell pieces 286, 288 of the handle 272 may enable the linear stator shaft 276 to be installed in the handle 272.

Figure 27:
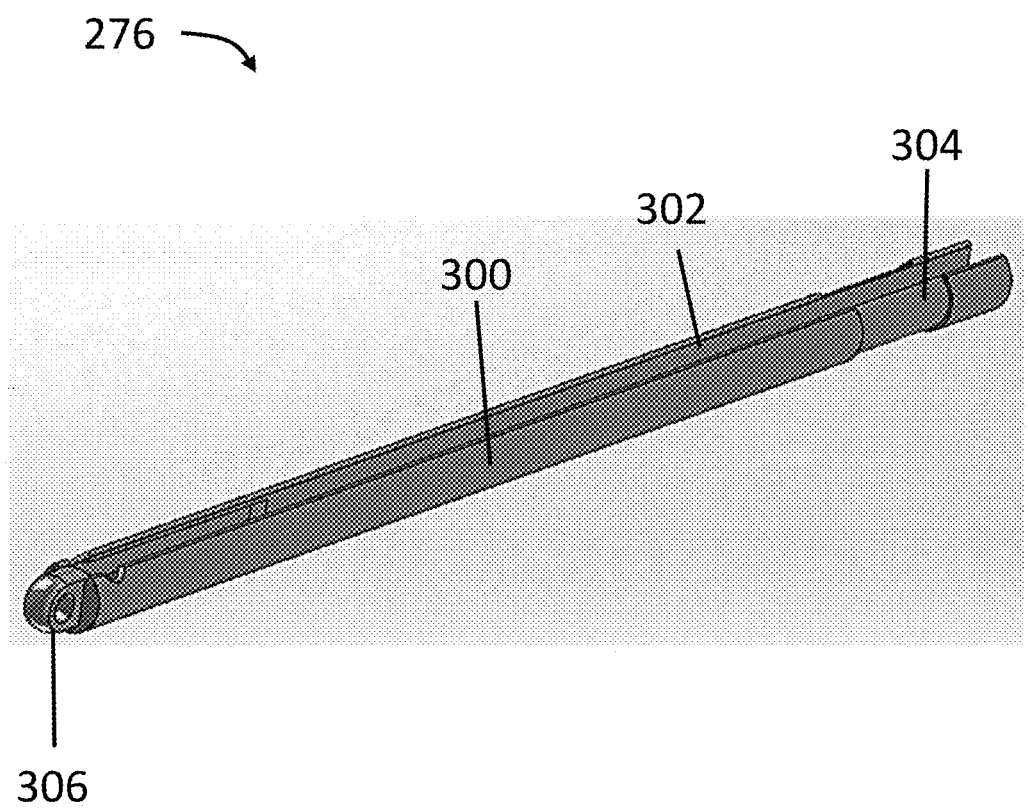
FIG. 27 illustrates a perspective view of a linear stator shaft for an articulated arthroscopic cutting tool assembly, according to aspects of the present embodiments.

FIG. 27 illustrates a perspective view of a linear stator shaft 276 for an articulated arthroscopic cutting tool assembly, according to aspects of the present embodiments. In general, the linear stator shaft 276 comprises a cylindrical rod 300, a rectangular groove 302 cut longitudinally along the cylindrical rod 300, a portion of reduced diameter 304 along the cylindrical rod 300 near the proximal end of the cylindrical rod 300, and a circular ring 306 protruding perpendicularly from the distal end of the cylindrical rod 300. In some embodiments, the portion of reduced diameter 304 may facilitate clamping in the handle 272 (which may include corresponding internal notches to interface with the reduced diameter 304, thereby preventing distal, proximal, or circumferential movement of the linear stator shat 276 relative to the handle 272). In some embodiments, the circular ring 306 may form part of a hinge or attachment for the curved oval blade 278.

Figure 28:
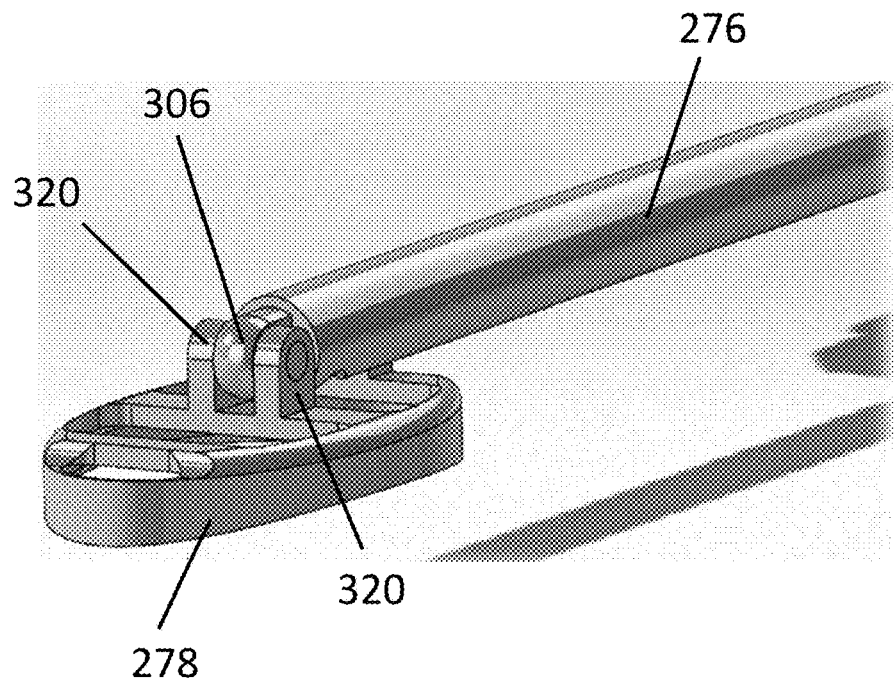
FIG. 28 illustrates a perspective view of the distal end of an articulated arthroscopic cutting tool assembly, according to aspects of the present embodiments.

FIG. 28 illustrates a perspective view of the distal end of an articulated arthroscopic cutting tool assembly 270, according to aspects of the present embodiments. In general, the linear stator shaft 276 may be connected to the curved oval blade 278 at a hinge formed by the circular ring 306 from the linear stator shaft 276 attached to two circular rings 320 extending from the curved oval blade 278.

Figure 29:
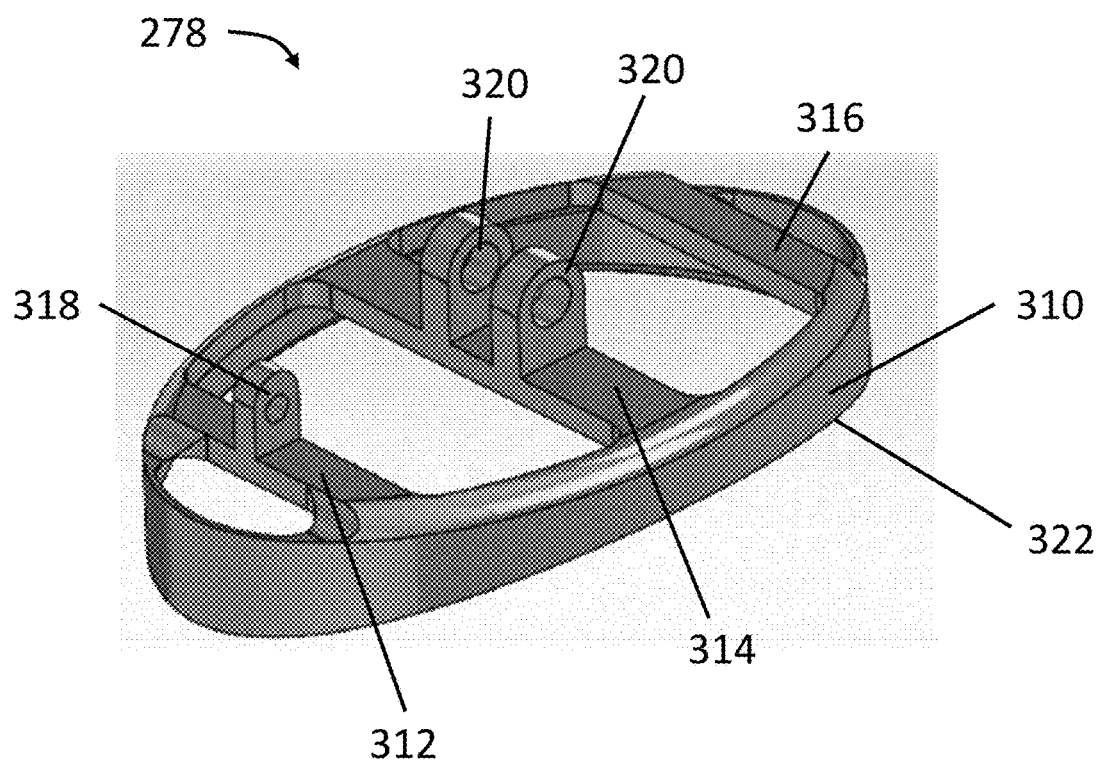
FIG. 29 illustrates a perspective view of a blade for an articulated arthroscopic cutting tool assembly, according to aspects of the present embodiments.

FIG. 29 illustrates a perspective view of a curved oval blade 278 for an articulated arthroscopic cutting tool assembly 270, according to aspects of the present embodiments. In general, the curved oval blade 278 may include an oval ring 310 and at least three crossbar pieces 312, 314, 316 spanning across a top surface of the oval ring 310. In some embodiments, a circular ring 318 may extend perpendicularly from the first crossbar piece 312, while two circular rings 320 may extend perpendicularly from the second crossbar piece 314. The top edge of the ring 310 may be curved while the bottom edge of the ring may comprise a curved cutting surface that comprises a surgically sharp edge 322. In some embodiments, the oval ring 310 may be thicker at the narrow ends of the oval ring.

In some embodiments, a surgeon or user may make use of additional sterile components suitable for easy use in the surgical environment, which may include a suitable hemostatic barrier, suitable covering patch, and/or organic glue.

In some embodiments, a surgeon or user may make use of a cell-free matrix material suitable for supporting autologous chondrocytes or allogeneic chondrocytes, for example that may be suitable for implanting into an articular joint surface defect.

In some embodiments, a surgeon or user may make use of a suitable hemostatic barrier, which may be or include, for example, a Surgicel® hemostatic barrier.

In some embodiments, a surgeon or user may make use of a suitable covering patch, which may be or include a Bio-Gide® covering patch.

In some embodiments, a hemostatic barrier (e.g., a Surgicel® hemostatic barrier) and/or a covering patch (e.g., an ACI-Maix® covering patch) may include a glue, e.g., a tissue glue, which, in some embodiments, may be an organic glue (e.g., a Tisseel® organic glue). In some embodiments, glue may be applied (e.g., as a covering) so that time to resorption is increased.

In some embodiments, a hemostatic barrier (e.g., a Surgicel® hemostatic barrier) and/or a covering patch (e.g., a Bio-Gide® covering patch), and in particular one treated with a glue (e.g., may include a Tisseel® organic glue) may be supplemented with aprotinin (e.g., in a manner and/or to an extent that time to resorption is increased).

In some embodiments, a hemostatic barrier and covering-patch may be both a semi-permeable collagen matrix, which is treated to extend the time until resorption of the material.

In some embodiments, an instrument system may include a surgical instrument or multiple surgical instruments. In some embodiments, an instrument system may include one or more cannulae (e.g., 1, 2, 3, 4, 5, or 10 or more cannulae). In some embodiments, an instrument system may include a cannula or multiple cannulae having inner diameters within a range from about 5 mm to about 20 mm, about 6 mm to about 12 mm, about 7 mm to about 11 mm, about 8 to about 9 mm, or about 10 to 25 mm. In some embodiments, cannulae may be composed of a material selected from the group consisting of plastics, metals, rubber, silicone, fiberglass, and combinations thereof (for example, composite materials).

Figure 30:
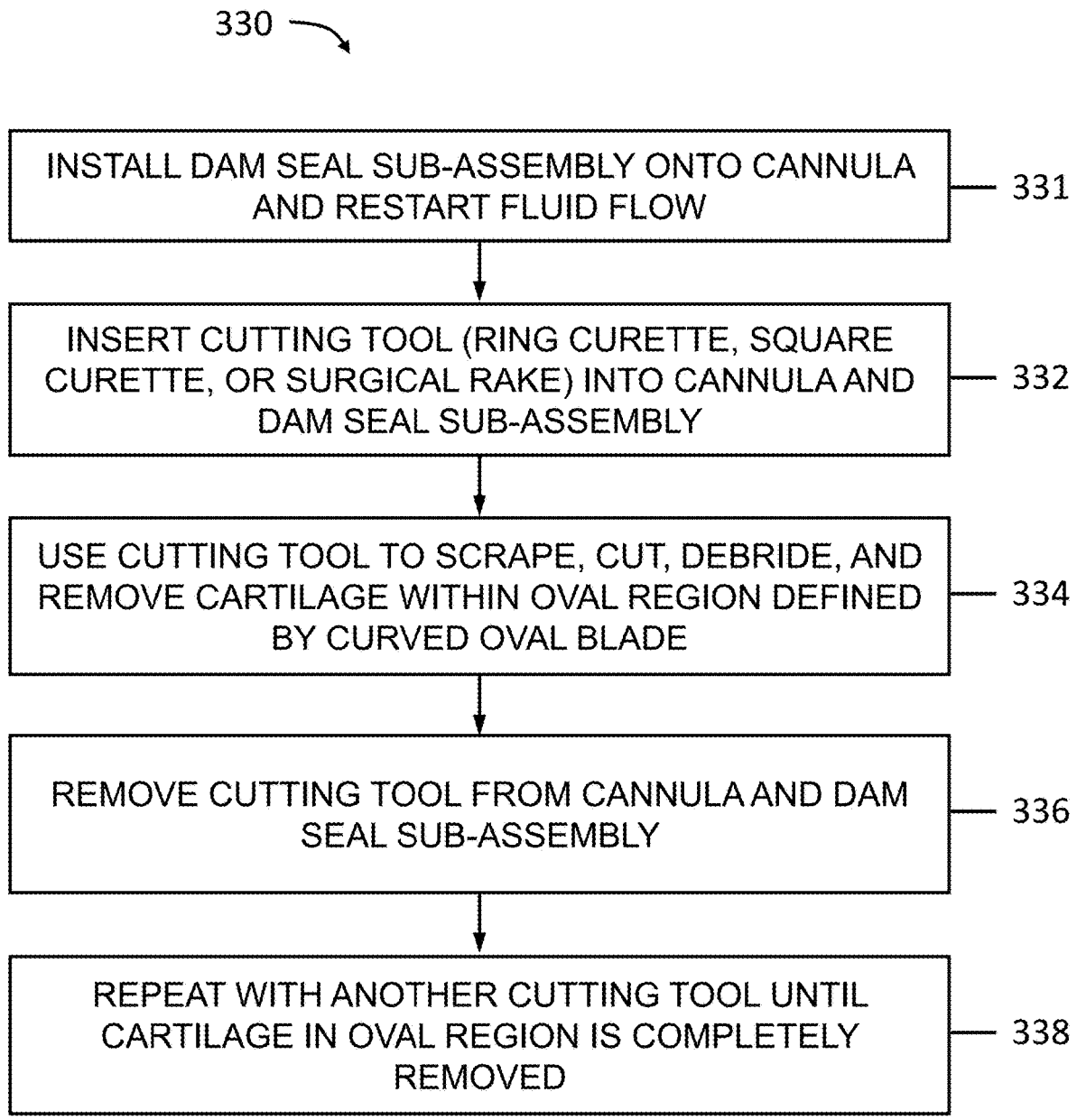
FIG. 30 illustrates a schematic of a method for preparing a surgical site using at least one of a ring curette, square curette, or a rake curette during an arthroscopic surgical procedure, according to aspects of the present embodiments.

FIG. 30 illustrates a schematic of a method 330 for preparing a surgical site using at least one of a ring curette 350, square curette 400, or rake curette 430 (for example, a 3.6 mm rake curette 430) during an arthroscopic surgical procedure, according to aspects of the present embodiments. Generally, the method 330 proceeds after the method 250 has been completed. Generally, the steps may include installing a dam seal sub-assembly 94 onto a cannula 96 and restarting fluid flow (step 331); inserting a cutting tool, which may include a ring curette 350, a square curette 400, or a rake curette 430, into a cannula 96 and dam seal sub-assembly 94 (step 332); using the cutting tool to scrape, cut, debride, and/or remove cartilage 42 within an oval region 52 defined earlier by a curved oval blade 278 on an articulated arthroscopic cutting tool 270 (step 334); removing the cutting tool from the cannula and dam seal sub-assembly 94 (step 336); and repeating the steps 332 to 336 as needed until cartilage in the cut region of cartilage is completely removed (step 338).

Figure 31:
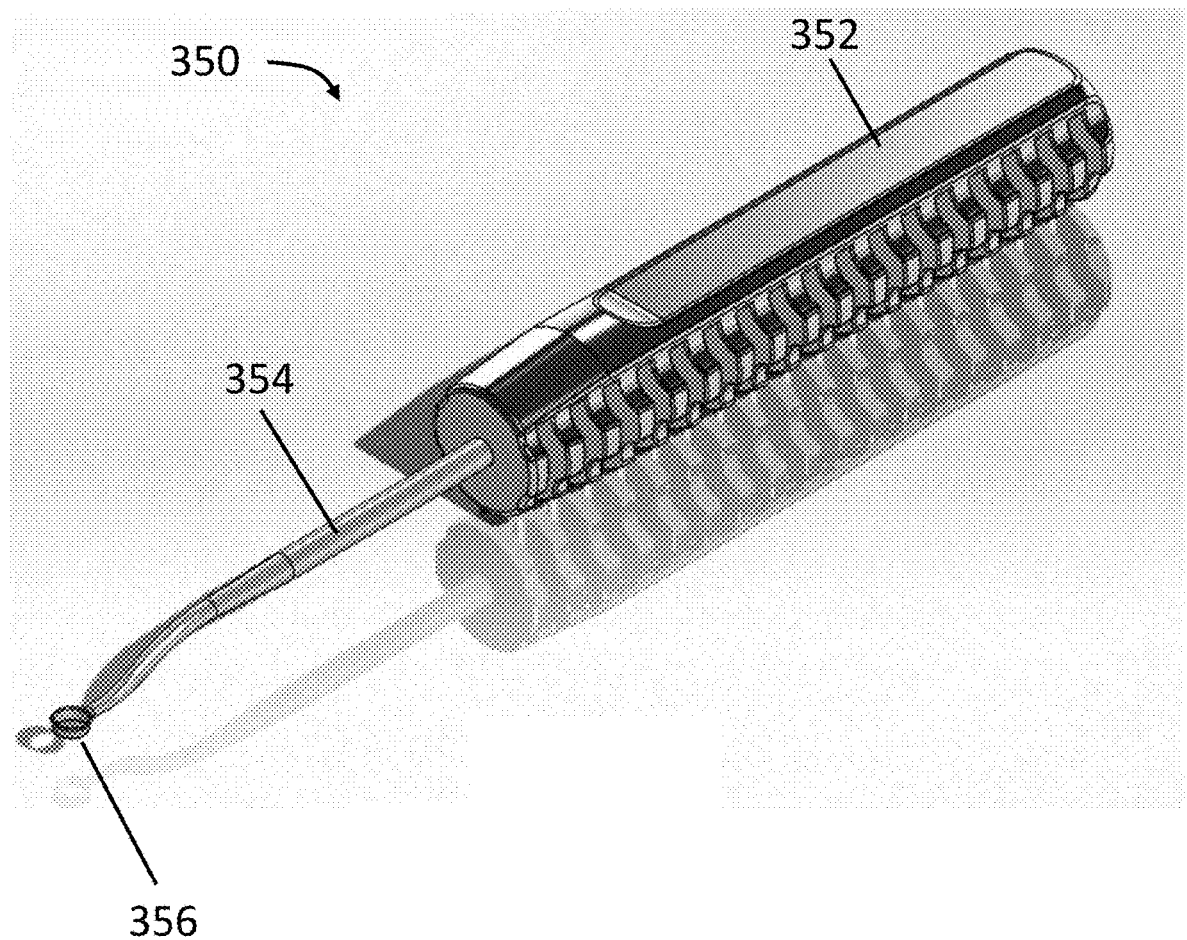
FIG. 31 illustrates a ring curette assembly, according to aspects of the present embodiments.

FIG. 31 illustrates a ring curette assembly 350, according to aspects of the present embodiments. In general, the ring curette assembly 350 includes a handle 352, a shaft 354 coupled to the distal end of the handle 352, and a ring curette blade 356 coupled to the distal end of the shaft 354. In some embodiments, the shaft 354 may comprise a cylindrical rod with at least two bends 362, 364, such that the distal end of the shaft has an axis that is parallel to and eccentric from a primary longitudinal axis of the shaft. In some embodiments, the ring curette blade 356 may comprise at least one surgically sharp edge 374.

Figure 32:
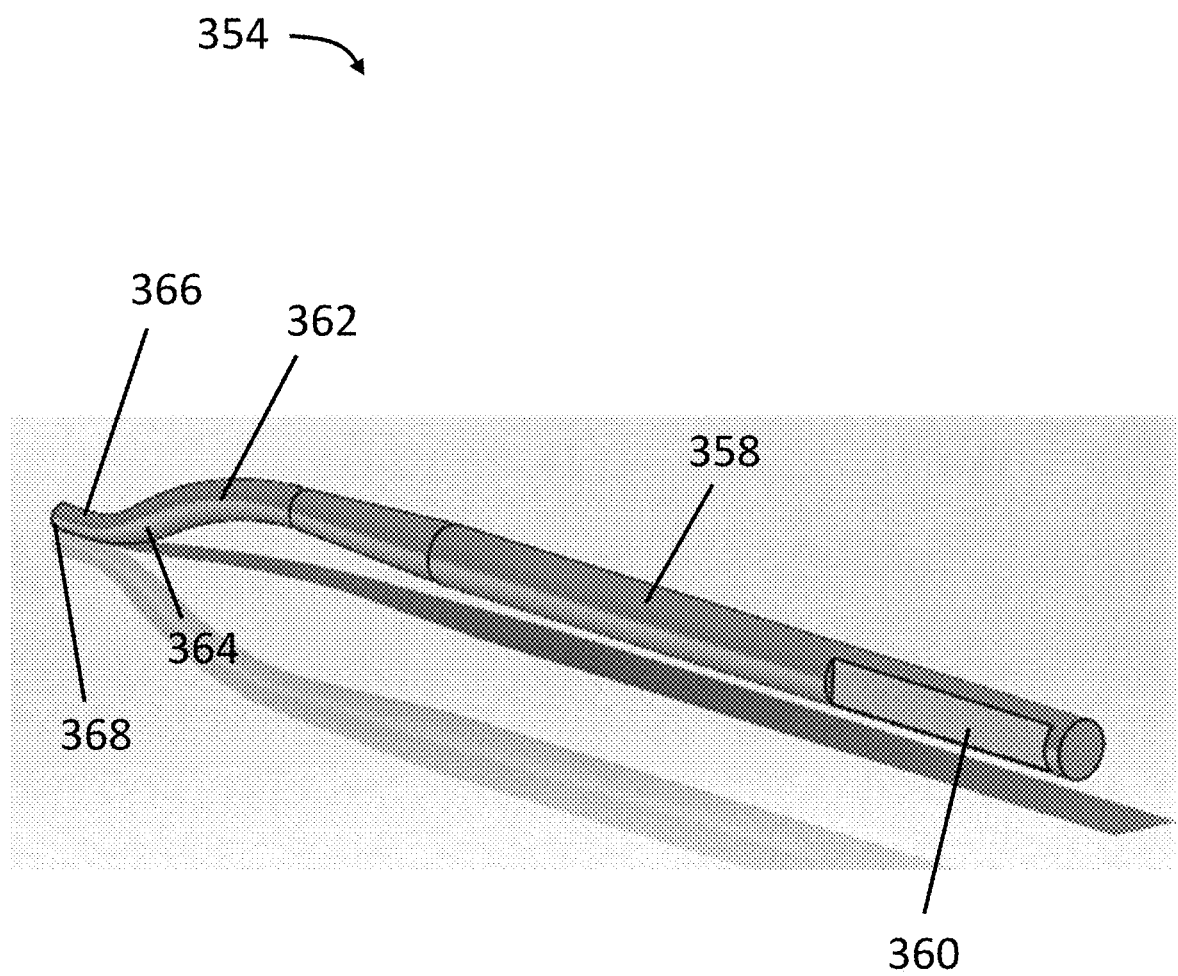
FIG. 32 illustrates a shaft that may be used for a ring curette assembly or a square curette assembly, according to aspects of the present embodiments.

FIG. 32 illustrates a shaft 354 that may be used for a ring curette assembly 350 or a square curette assembly 400, according to aspects of the present embodiments. In general, the shaft 354 comprises a cylindrical rod 358; a flat portion 360 at the proximal end of the cylindrical rod 358 that may be used to facilitate attachment within the handle 352; a first bend 362 in the cylindrical rod 358 near the distal end of the rod such that the rod axis is angled away from a primary longitudinal axis of the cylindrical rod; a second bend 364 in the cylindrical rod further toward the distal end of the rod such that the rod axis is angled parallel to and positioned eccentrically from the primary longitudinal axis of the cylindrical rod; a cylindrical portion with reduced diameter 366 near the distal end of the rod; and a recessed opening 368 at the distal end of the shaft with flat interior surfaces.

Figure 33:
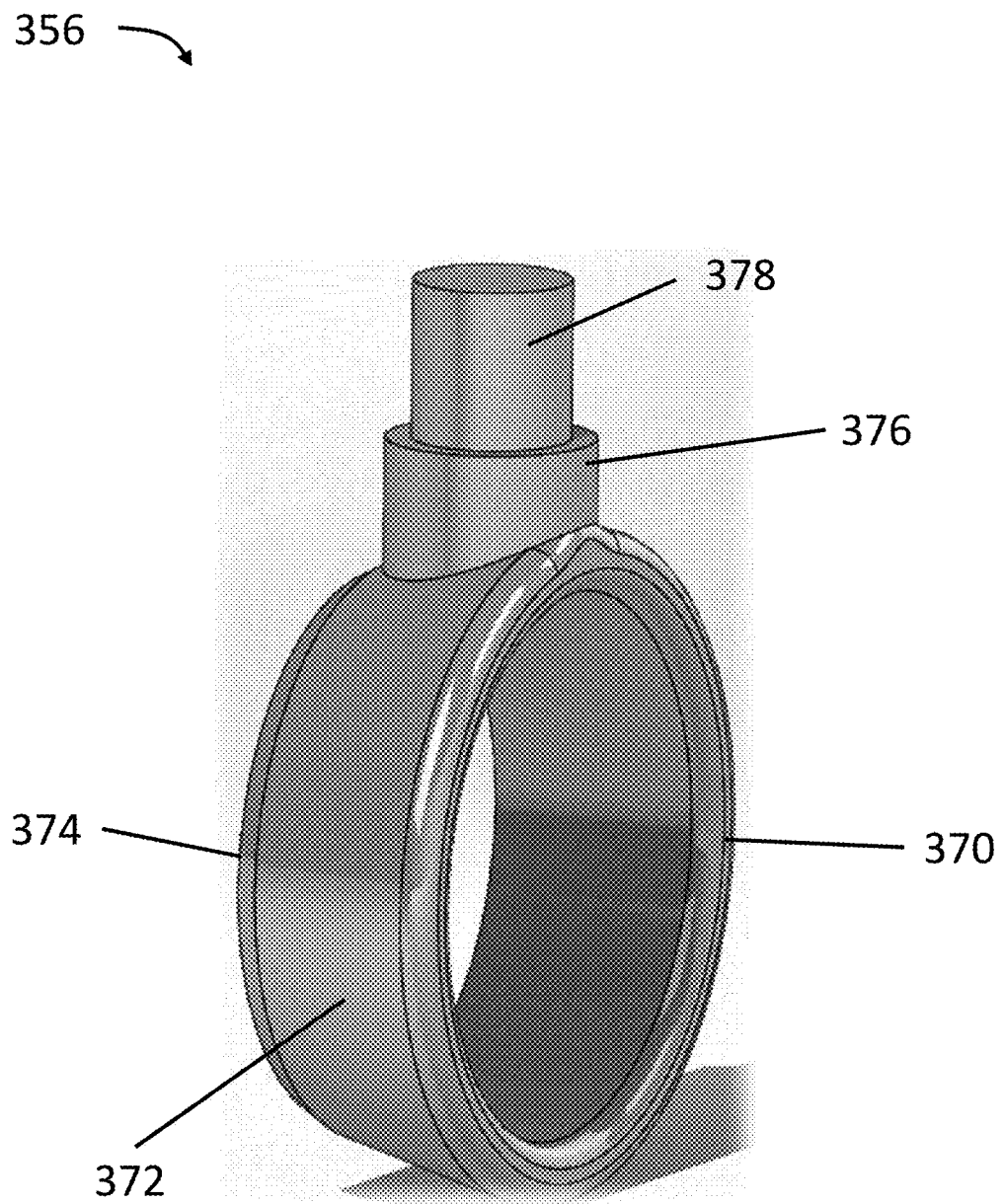
FIG. 33 illustrates a perspective view of a ring curette blade, according to aspects of the present embodiments.

FIG. 33 illustrates a perspective view of a ring curette blade 356, according to aspects of the present embodiments. In general, the ring curette blade 356 may comprise a ring 372 in the shape of a hollow right circular conical frustum; a rounded edge 370 around the larger circumference of the ring 372; a surgically sharp edge 374 around the larger circumference of the ring 372; a cylindrical connection shaft 376 disposed pointing radially out at an outer wall of the ring 372; and a cylindrical welding shaft 378 disposed coaxially with the connection shaft 376. In some embodiments, the cylindrical welding shaft 378 may have a smaller diameter than the cylindrical connection shaft 376, which is fitted with the recessed opening 368 such that the distill edge of the shaft 354 interfaces with the a proximal edge of the cylindrical welding shaft 378, thereby allowing the two surfaces to be bonded via welding (for example, laser welding)

Referring still to FIG. 32 and FIG. 33, in some embodiments the shaft 354 and ring curette blade 356 may comprise or be composed of stainless steel type 17-4PH (630) or equivalent, UNS S17400, per ASTM A564. In some embodiments, the shaft 354 and ring curette blade 356 may comprise or be composed of one of a metal, a metallic alloy, titanium, carbon steel, stainless steel, tool steel, chrome steel, or ceramic. In some embodiments, the welding shaft 378 of the ring curette blade 356 may be disposed within the recessed opening 368 at the distal end of the shaft 354, and may be joined by laser welding.

Figure 34:
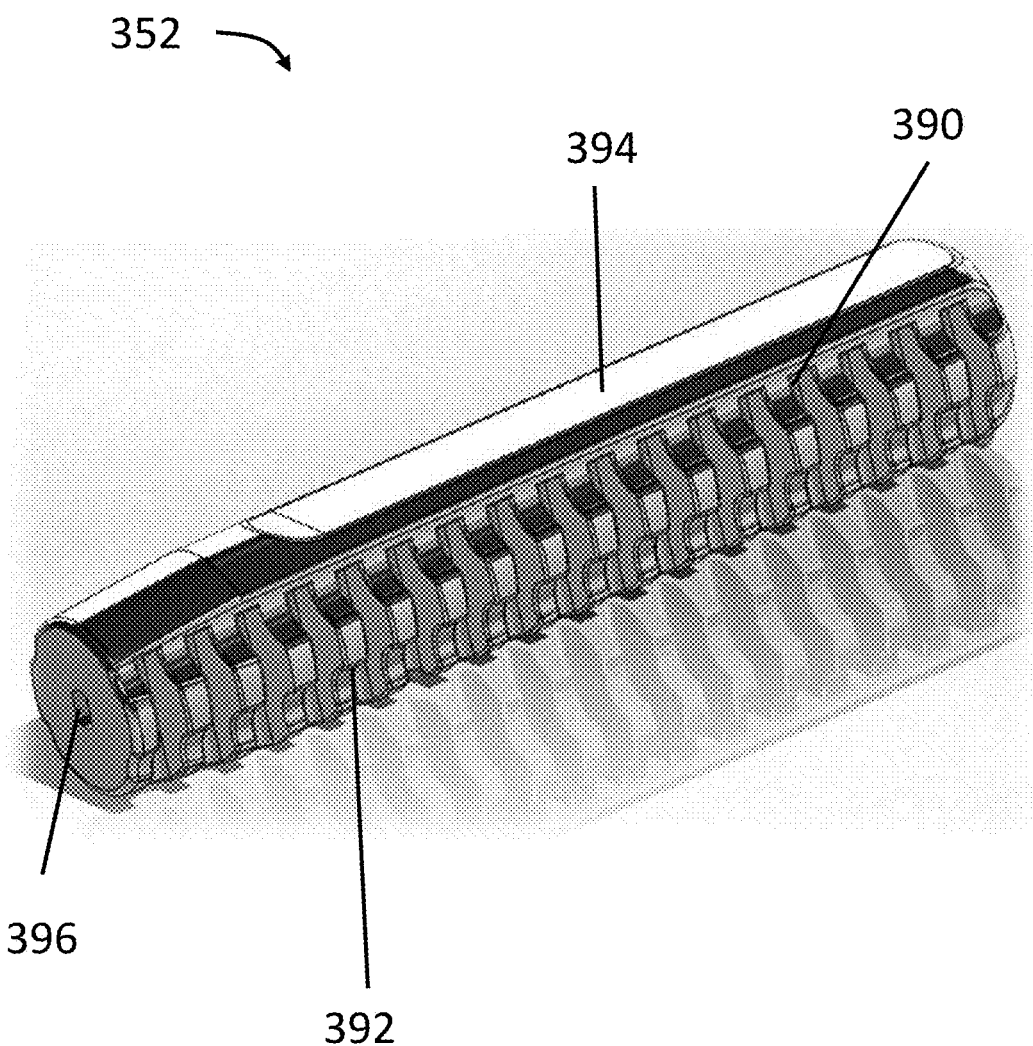
FIG. 34 illustrates a handle assembly that may be used for a ring curette, a square curette, or a rake curette, according to aspects of the present embodiments.

FIG. 34 illustrates a handle assembly 352 that may be used for a ring curette 350, a square curette 400, or a rake curette 430, according to aspects of the present embodiments. In general, the handle assembly 352 may comprise a cylindrical body 390; a plurality of ridges 392 on exterior lateral and bottom surfaces of the cylindrical body 390 arranged perpendicular to the longitudinal axis of the cylindrical body 390; a flat surface 394 along a top surface of the cylindrical body; and a circular opening 396 in the distal end of the cylindrical body 390. In some embodiments, the handle assembly 352 may comprise or be composed of acrylonitrile butadiene styrene (ABS) or other plastic or polymeric materials or equivalent.

Figure 35:
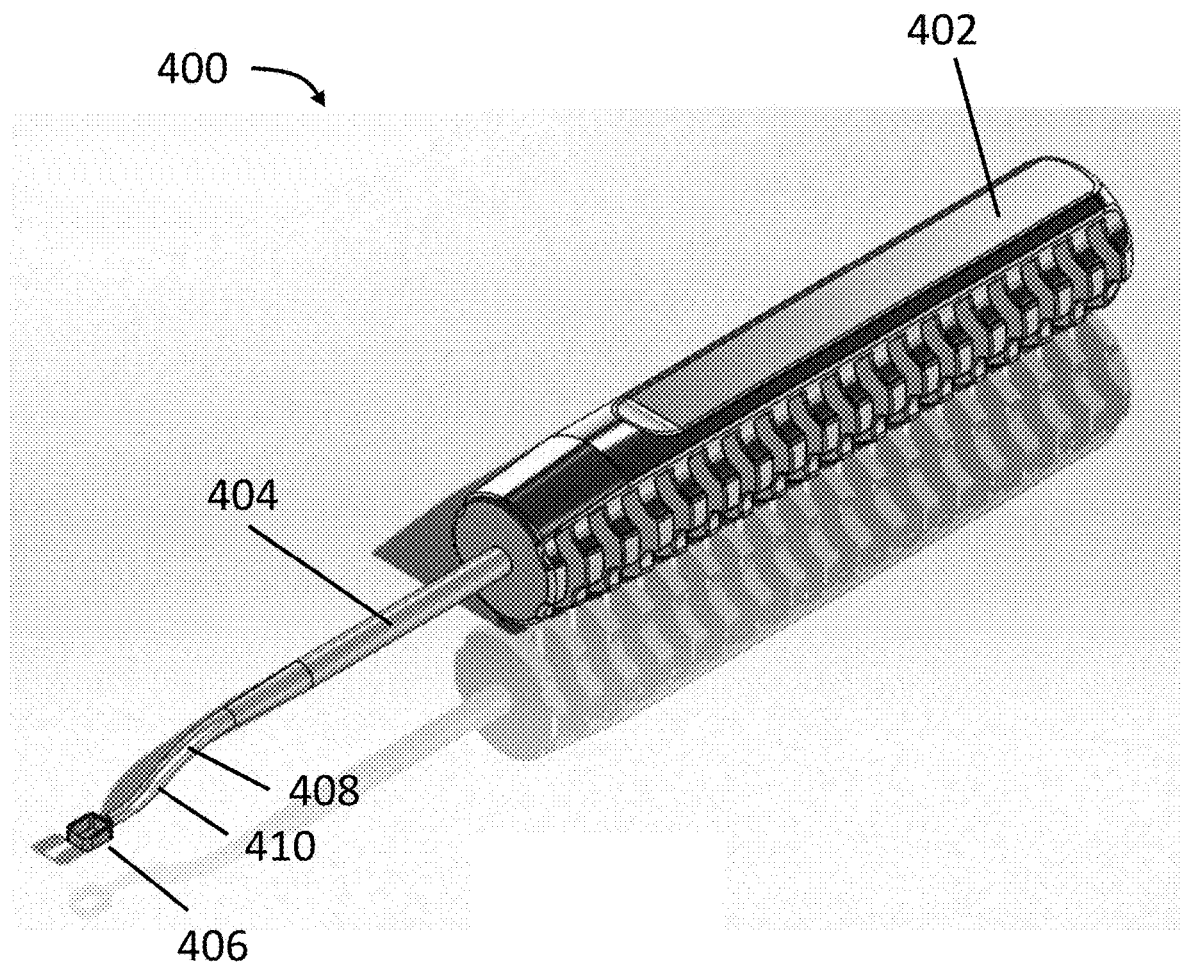
FIG. 35 illustrates a square curette assembly, according to aspects of the present embodiments.

FIG. 35 illustrates a square curette assembly 400, according to aspects of the present embodiments. In general, the square curette assembly 400 may comprise a handle 402; a shaft 404 coupled to the distal end of the handle 402; and a square curette blade 406 coupled to the distal end of the shaft 404. In some embodiments, the shaft 404 may comprise a cylindrical rod with at least two bends 408, 410, such that the end of the shaft has an axis that is parallel to and eccentric from a primary longitudinal axis of the shaft. In some embodiments, the shaft 404 may comprise the same structure as the shaft 354 illustrated in FIG. 32. In some embodiments, the square curette blade 406 comprises at least two surgically sharp edges 412, 414 at the distal end of the square curette blade (as shown in FIG. 36).

Figure 36:
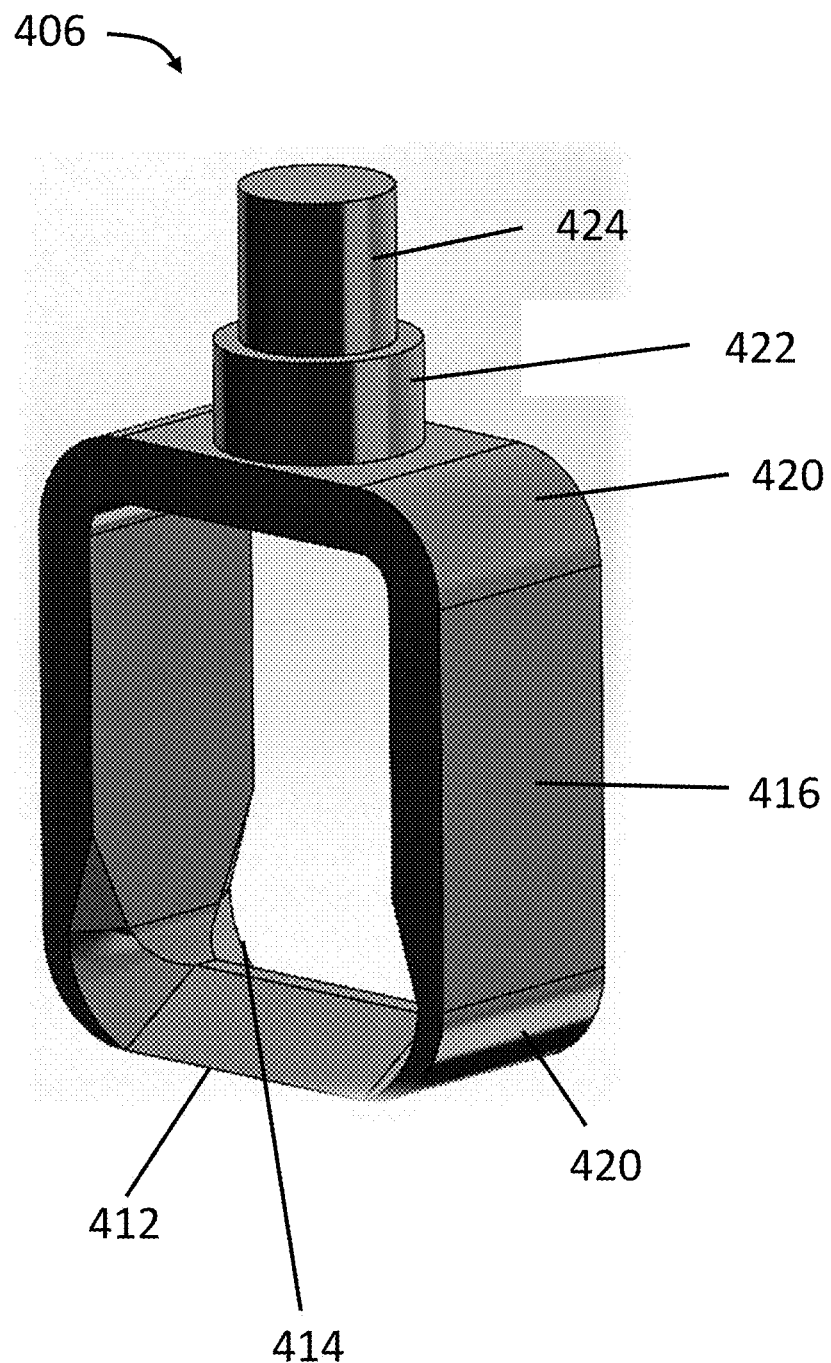
FIG. 36 illustrates a square curette blade for a square curette assembly, according to aspects of the present embodiments.

FIG. 36 illustrates a square curette blade 406 for a square curette assembly 400, according to aspects of the present embodiments. In general, the square curette blade 406 may comprise a ring 416 in the shape of a hollow, rounded, rectangular prism; at least two surgically sharp edges 412, 414 at a top and a bottom edge of the ring at the distal side of the rectangular prism; a cylindrical connection shaft 422 disposed pointing outward at an outer wall of the ring at a position on the ring that is opposite to the location of the two surgically sharp edges; and a cylindrical welding shaft 424 disposed coaxially with the connection shaft 422. In some embodiments, the cylindrical welding shaft 424 has a smaller diameter than the connection shaft 422, and may connect to the shaft 404 via laser weld similar to the embodiment illustrated in FIG. 33.

Referring still to FIG. 35 and FIG. 36, in some embodiments the shaft 404 and the square curette blade 406 may comprise or be composed of stainless steel type 17-4PH (630) or equivalent, UNS S17400, per ASTM A564. In some embodiments, the shaft 404 and the square curette blade 406 may comprise or be composed of one of a metal, a metallic alloy, titanium, carbon steel, stainless steel, tool steel, chrome steel, or ceramic. In some embodiments, the welding shaft 424 of the square curette blade 406 may be disposed within the recessed opening 368 at the distal end of the shaft 354, and may be joined by laser welding.

Figure 37:
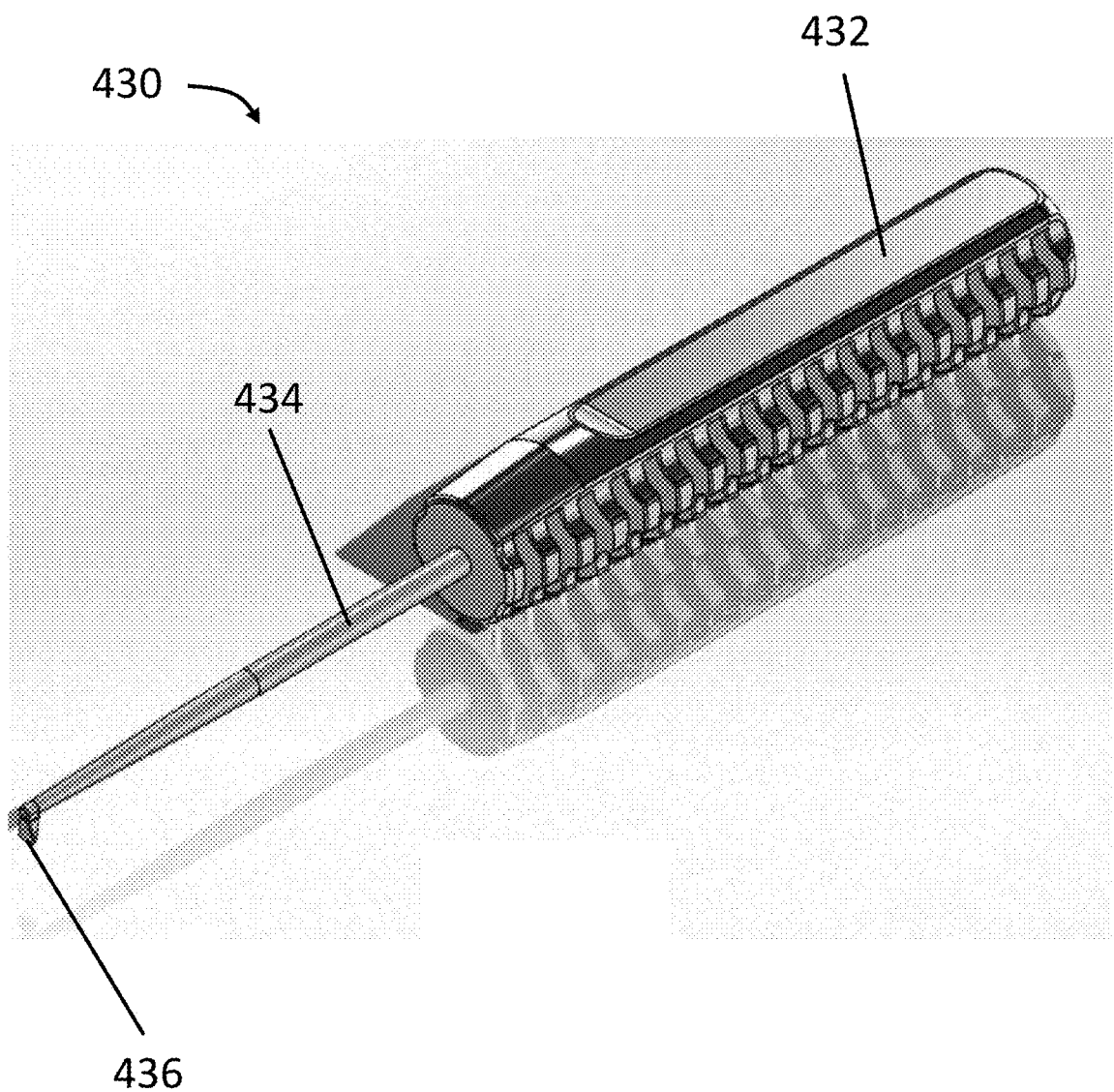
FIG. 37 illustrates a rake curette assembly, according to aspects of the present embodiments.

FIG. 37 illustrates a rake curette assembly 430, according to aspects of the present embodiments. In general, a rake curette assembly 430 may comprise a handle 423; a shaft 434 coupled to the distal end of the handle 432; and a rake head blade 436 coupled to the distal end of the shaft 434. In some embodiments, the shaft may comprise a cylindrical rod that tapers to a smaller diameter near the distal end of the shaft 434. In some embodiments, the rake head blade 436 may comprise a tapered wedge with at least one surgically sharp edge 454. In some embodiments, the rake head blade 436 may be disposed such that it points perpendicularly and radially away from the longitudinal axis of the shaft 434, and such that the surgically sharp edge 454 is disposed perpendicular to the longitudinal axis of the shaft 434, and as such the rake curette comprises an adze-like tool rather than an axe-like tool.

Figure 38:
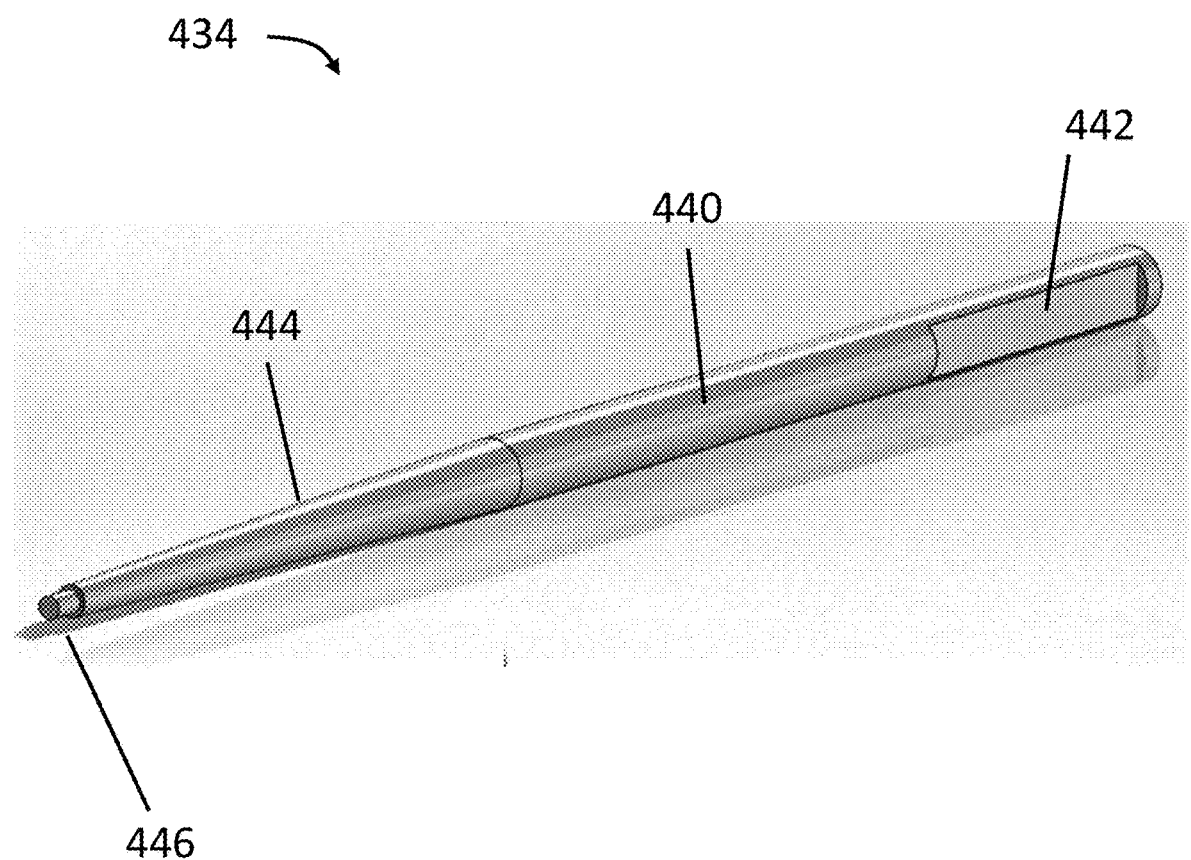
FIG. 38 illustrates a rake shaft for a rake curette assembly, according to aspects of the present embodiments.

FIG. 38 illustrates a rake shaft 434 for a rake curette assembly 430, according to aspects of the present embodiments. The rake shaft 434 comprises a cylindrical rod 440; a flat portion 442 at the proximal end of the shaft for attachment within the handle 432; a tapered portion 444 where a diameter of the cylindrical rod 440 decreases gradually toward the distal end of the shaft; and a cylindrical welding shaft 446 disposed coaxially within the tapered portion 444 of the shaft 434, with a further reduced diameter.

Figure 39:
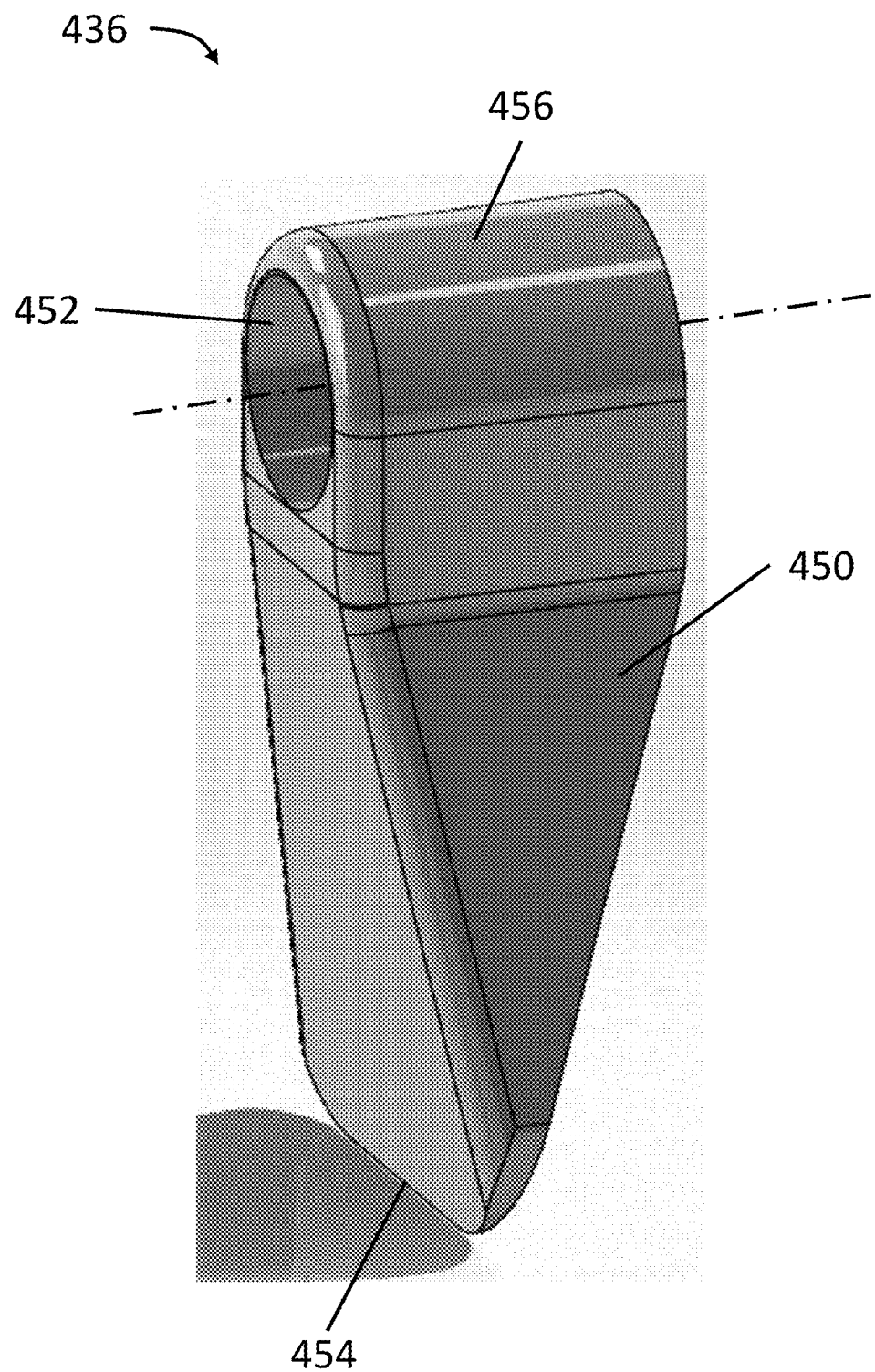
FIG. 39 illustrates a rake head blade for a rake curette assembly, according to aspects of the present embodiments.

FIG. 39 illustrates a rake head blade 436 for a rake curette assembly 430, according to aspects of the present embodiments. In general, the rake head blade 436 may comprise a wedge-shaped body 450 that decreases in thickness while increasing in depth; a rounded top portion 456 with a cylindrical opening 452 for laser welding, and a surgically sharp edge 454 at the end of the wedge-shaped body.

Referring still to FIG. 38 and FIG. 39, in some embodiments the shaft 434 and rake head blade 436 may comprise or be composed of stainless steel type 17-4PH (630) or equivalent, UNS S17400, per ASTM A564. In some embodiments, the shaft 434 and rake head blade 436 may comprise or be composed of one of a metal, a metallic alloy, titanium, carbon steel, stainless steel, tool steel, chrome steel, or ceramic. In some embodiments, the cylindrical welding shaft 446 of the shaft 434 may be inserted into the cylindrical opening 452 of the rake head blade 436 and may be joined by laser welding.

Figure 40:
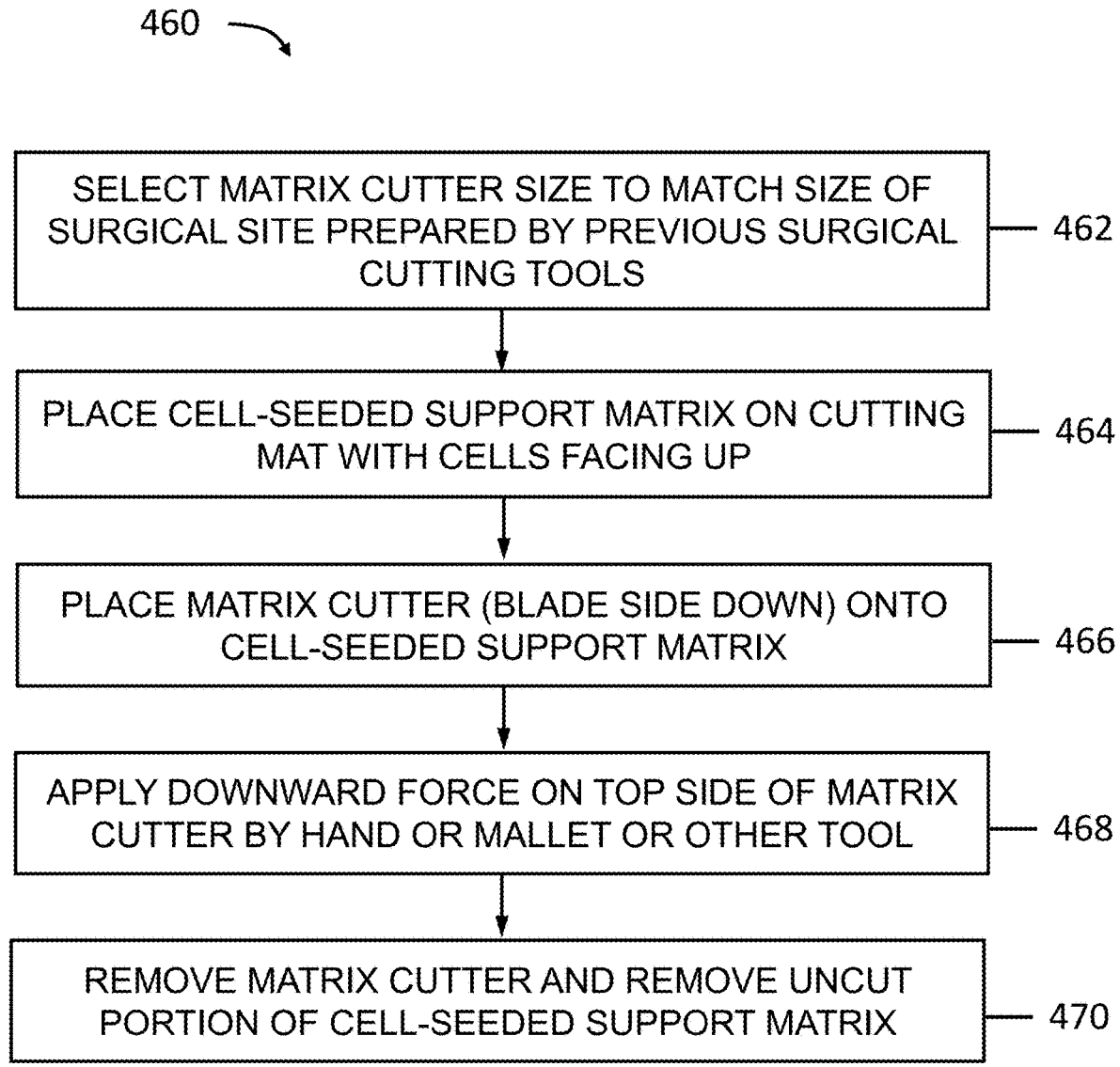
FIG. 40 illustrates a schematic of a method to prepare a cell-seeded matrix composition for use during an arthroscopic surgical procedure, according to aspects of the present embodiments.

FIG. 40 illustrates a schematic of a method 460 to prepare a cell-seeded matrix composition for use during an arthroscopic surgical procedure, according to aspects of the present embodiments. Generally, method 460 may comprise selecting a matrix cutter size to match a surgical site prepared by cutting and cleaning away cartilage surrounding a defect or lesion using surgical cutting tools in previous method 330 (step 462); placing a cell-seeded support matrix on a cutting mat, with the cells on the matrix facing upward (step 464); placing the selected matrix cutter onto the cell-seeded support matrix, with a surgically sharp edge facing downward (step 466); applying downward force on a top side of the matrix cutter using at least one of a hand, a mallet, a hammer, and/or other tool (step 468); and removing the matrix cutter and removing an uncut portion of the cell-seeded support matrix (step 470). In some embodiments, the remaining cut portion of cell-seeded support matrix may comprise an oval shape or other shape matching the shape of the matrix cutter.

FIG. 41A illustrates a view demonstrating a preparation of a cell-seeded support matrix composition, according to aspects of the present embodiments. In this view, a portion of cell-seeded support matrix 482 is placed cell-seeded side facing upward on a cutting mat 480; a matrix cutter 484 is placed blade-side facing downward on top of the cell-seeded support matrix 462; and an operator is holding a mallet 486.

FIG. 41B illustrates a view demonstrating a preparation of a cell-seeded support matrix composition, according to aspects of the present embodiments. In this view, the mallet and matrix cutter 484 are in contact at location 488, downward force is being applied through the mallet 486, and a pair of tweezers 490 is visible nearby.

FIG. 41C illustrates a view demonstrating a preparation of a cell-seeded support matrix composition, according to aspects of the present embodiments. In this view, an uncut portion of the cell-seeded support matrix 482 is removed from the cutting mat 480, and the cut portion of matrix 492 is remaining, with a shape that matches the matrix cutter 484. The tweezers 490 may be used to handle the cell-seeded support matrix pieces 482, 492.

Figure 42:
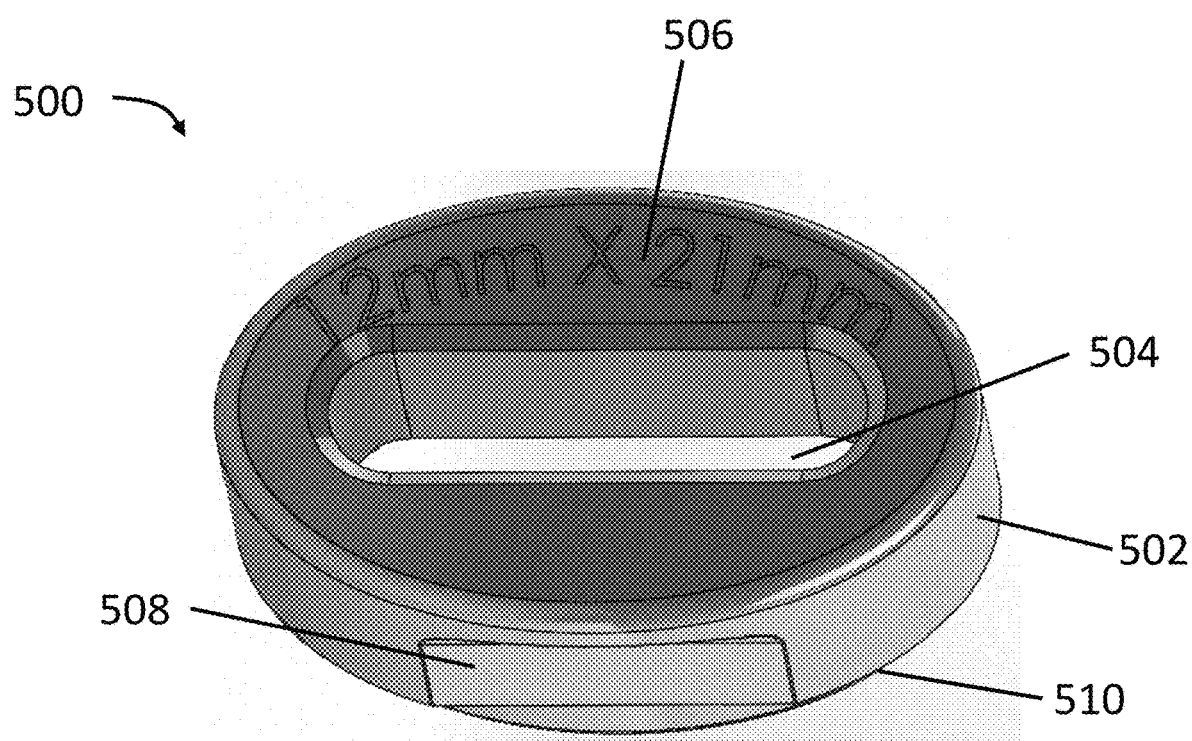
FIG. 42 illustrates a top-down perspective view of a matrix cutter, according to aspects of the present embodiments.

FIG. 42 illustrates a top-down perspective view of a matrix cutter 500, according to aspects of the present embodiments. In general, the matrix cutter 500 may comprise an elliptic cylinder body 502; an internal hole 504 shaped as a stadium aligned parallel with the semi-major axis of the elliptic cylinder body 502, and longitudinally aligned parallel with the longitudinal axis of the elliptic cylinder body 502; a flat top surface 506 of the elliptic cylinder body; at least two flat gripping notches 508 at opposite exterior sides of the elliptic cylinder body; and a surgically sharp edge 510 around a bottom circumference of the elliptic cylinder body 502. In some embodiments, the matrix cutter 500 may comprise or be composed of stainless steel type 17-4PH (630), UNS S17400, per ASTM A564. In some embodiments, the matrix cutter 500 may comprise or be composed of one of a metal, a metallic alloy, titanium, carbon steel, stainless steel, tool steel, chrome steel, or ceramic. In some embodiments, dimensions or other information may be etched or printed on the flat top surface 506. The internal hole 504 may also be shaped as an oblong or oval.

Figure 43:
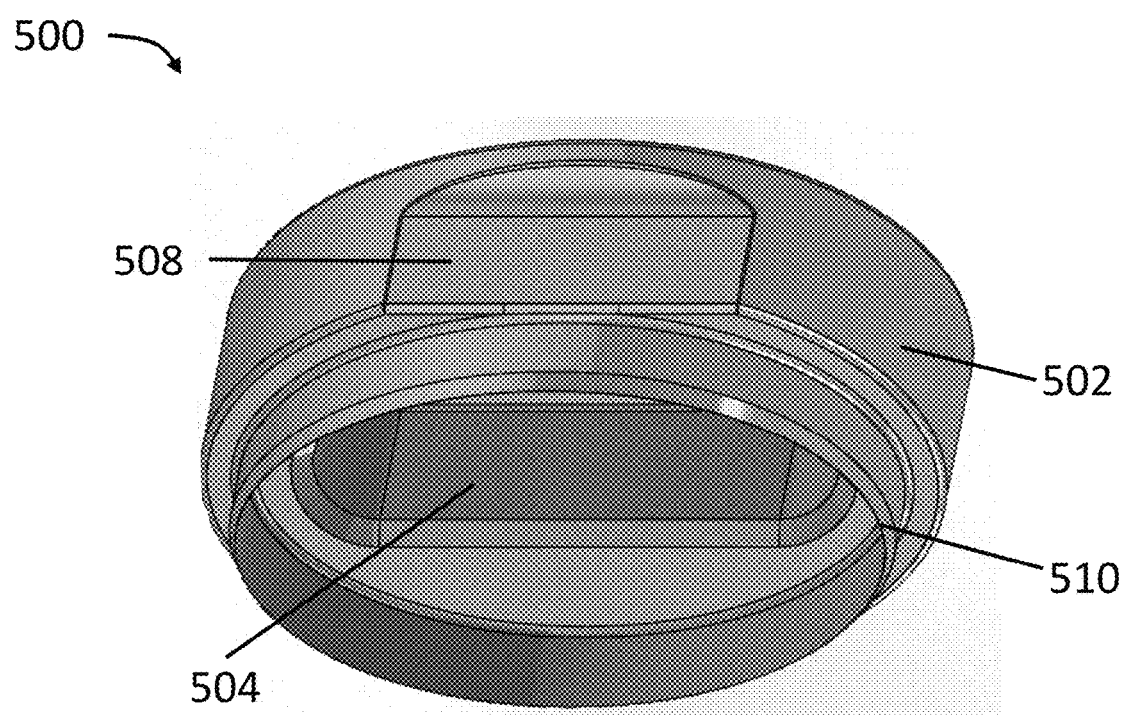
FIG. 43 illustrates a bottom-up perspective view of a matrix cutter, according to aspects of the present embodiments.

FIG. 43 illustrates a bottom-up perspective view of a matrix cutter 500, according to aspects of the present embodiments. The surgically sharp edge 510 is visible along a bottom circumference of the cutter body 502. In some embodiments, the flat gripping notches 508 may be used to pick up or handle the matrix cutter 500.

Figure 44:
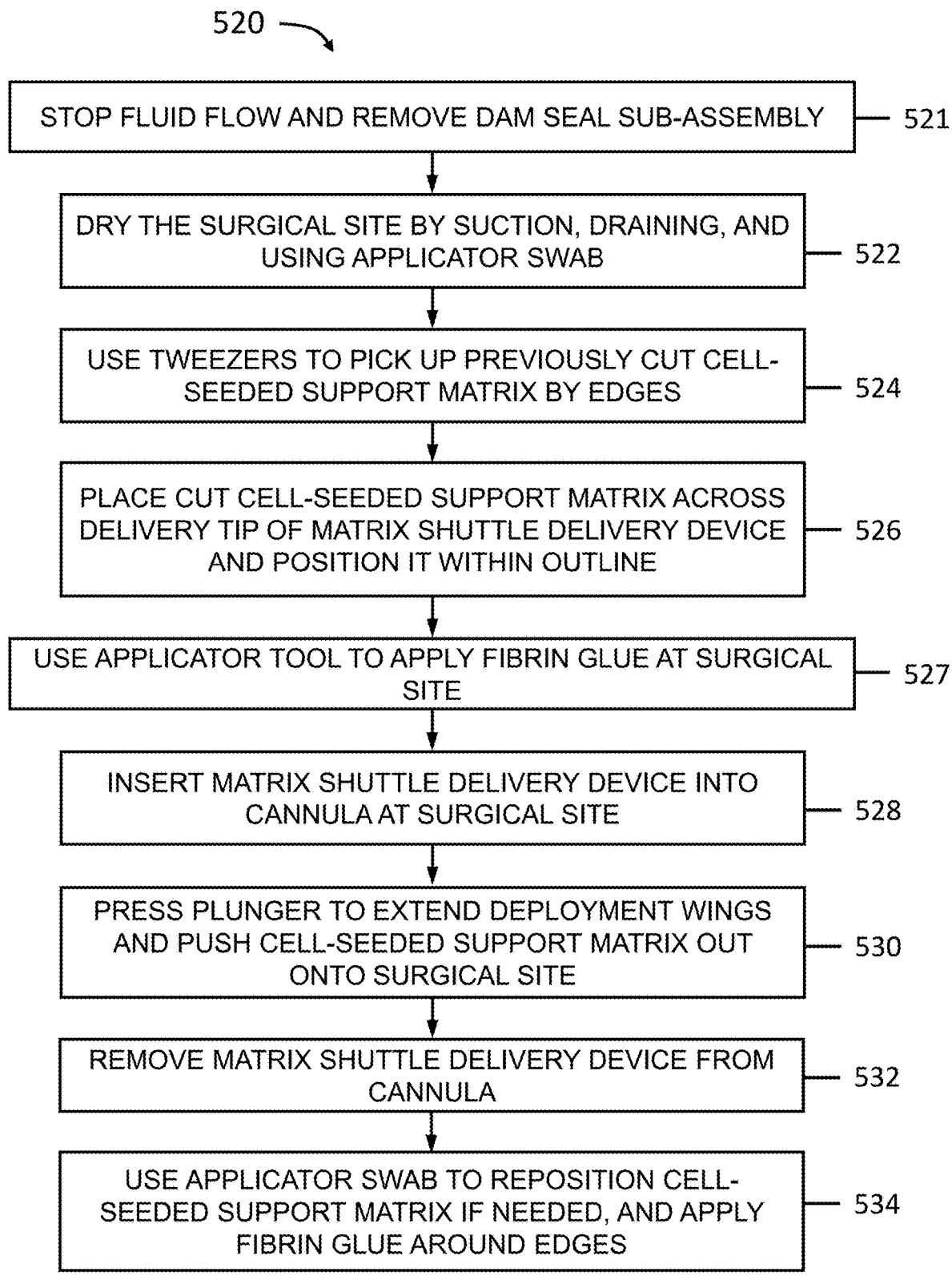
FIG. 44 illustrates a schematic of a method to implant a cell-seeded matrix composition, according to aspects of the present embodiments.

FIG. 44 illustrates a schematic of a method 520 to implant a cell-seeded matrix composition, according to aspects of the present embodiments. Generally, the method 520 may comprise stopping fluid flow, removing a dam seal subassembly (step 521), drying the surgical site where cartilage was previously cut and removed by suction, draining, and using a first applicator swab to clean and dry a surgical site (step 522); using tweezers to pick up a piece of previously cut cell-seeded support matrix by grasping an edge of the matrix (step 524); placing the cell-seeded support matrix across a delivery tip of a matrix shuttle device such that the matrix lies within an outline at the delivery tip and such that a cell-containing side of the matrix is facing away from the delivery tip (step 526); applying fibrin glue at the surgical site using an applicator tool (step 527); inserting the matrix shuttle device into a cannula at a surgical site (step 528); depressing a plunger on the matrix shuttle device to extend at least one antenna from within the delivery tip of the matrix shuttle device to push the cell-seeded support matrix out and onto the surgical site (step 530); removing the matrix shuttle device from the cannula (step 532); using a second applicator swab to reposition the cell-seeded support matrix if needed, and using the second applicator swab to apply fibrin glue around an edge of the cell-seeded support matrix at the surgical site (step 534).

Figures 45, 46:
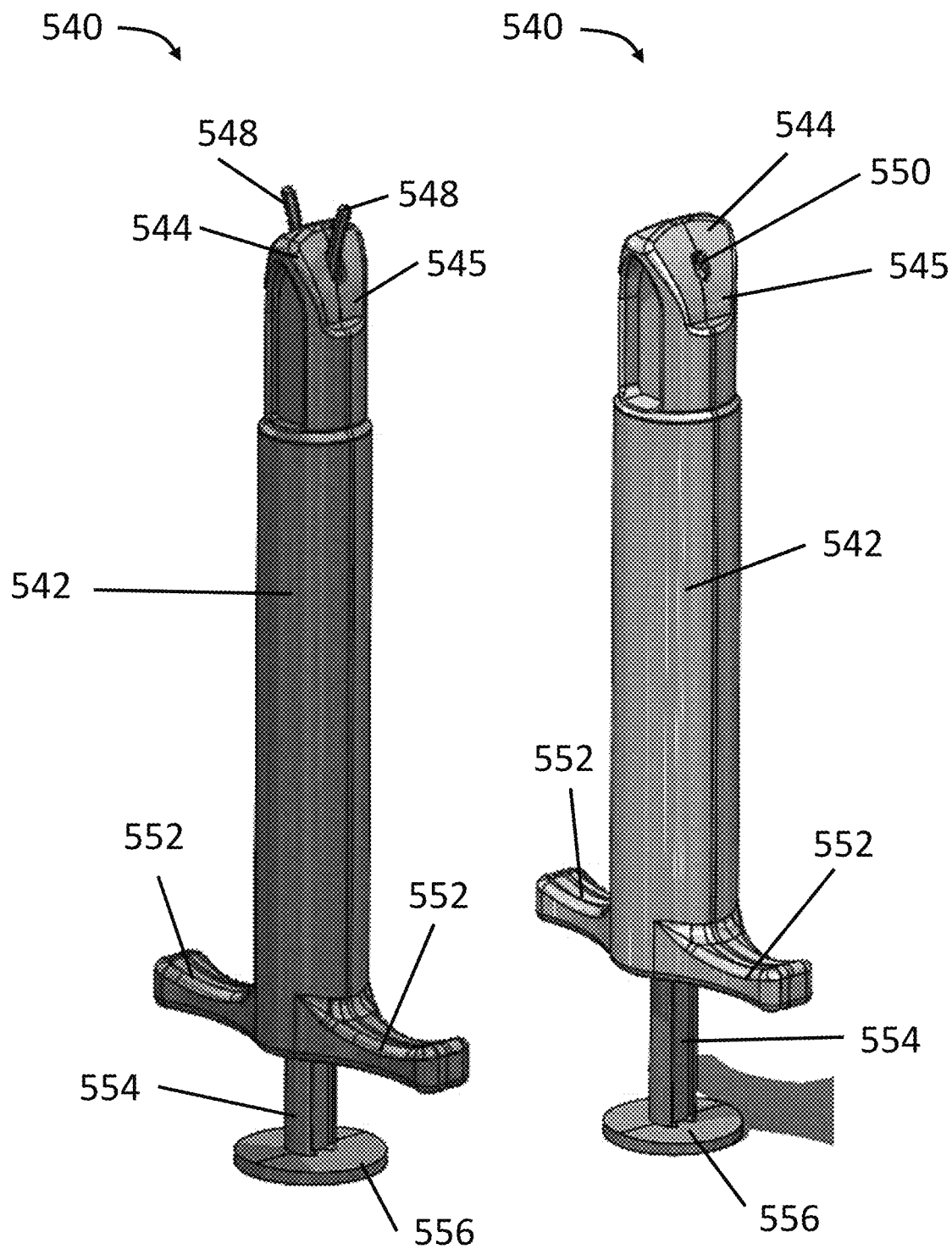
FIG. 45 illustrates a perspective view of a matrix shuttle delivery device with deployment wings extended, according to aspects of the present embodiments.
FIG. 46 illustrates a perspective view of a matrix shuttle delivery device with deployment wings retracted, according to aspects of the present embodiments.

FIG. 45 illustrates a perspective view of a matrix shuttle device 540 with deployment wings 548 extended, according to aspects of the present embodiments. FIG. 46 illustrates a perspective view of a matrix shuttle device 540 with deployment wings 548 retracted, according to aspects of the present embodiments. Referring to both FIG. 45 and FIG. 46, in general the matrix shuttle device 540 comprises a shuttle body 542; a delivery tip 544 at the distal end of the shuttle body 542; a plunger 554 disposed longitudinally within the shuttle body 542 and protruding out of the proximal end of the shuttle body 542 with a flat disc portion 556 (e.g., a thumb rest or a flange) at the proximal end of the plunger 554; at least two deployment wings 548 disposed inside the delivery tip 544 and attached to the plunger 554; at least two holes 550 on a distal surface of the delivery tip 544; a spring 558 (illustrated in FIG. 49) disposed longitudinally inside the shuttle body 542 and attached to the plunger 554; and one or more finger grips 552 disposed at the proximal end of the shuttle body 542. In some embodiments, pushing the plunger 554 longitudinally into the shuttle body 542 causes the at least two deployment wings 548 to extend externally through the at least two holes 550 of the delivery tip. In some embodiments, a proximal end of the spring 558 may be positioned or biased against an intermediate portion of the plunger 554 (for example, positioned so as to be in contact with cylindrical body 560). In some embodiments, a distal end of spring 558 may be positioned or biased against an interior surface of the shuttle body (for example, internal surfaces of shells 562, 564). Pushing and releasing the plunger 554 respectively compresses and expands the spring 558 along a longitudinal direction. In some embodiments, the spring causes the at least two deployment wings to retract inside the at least two holes when the plunger is released.

In some embodiments, the spring 558 may be formed from stainless steel or type 302 stainless steel and/or other metal. In some embodiments, the spring 558 may be about 1.25 inches long (or between about 1 inch and 2 inches, or between about 1 inch and 1.5 inches, or between about 1.1 and 1.3 inches, or between about 1.2 and 1.4 inches long). In some embodiments, the spring may have an outer diameter (OD) of about 0.36 inches (or between about 0.3 and 0.4 inches, or between about 0.25 and 0.5 inches) and may have an inner diameter of about 0.298 inches (or between about 0.2 inches and 0.3 inches, or between about 0.2 inches and 0.4 inches, where the inner diameter is less than the inner diameter of the spring).

FIG. 47 illustrates a side view of a delivery tip 544 of a matrix shuttle device 540 with cell-seeded support matrix 492 placed across the delivery tip 544, according to aspects of the present embodiments. In some embodiments, the cell-seeded support matrix 492 may be cut using a matrix cutter following method 460 and may be shaped like an oval or other shape. The arrow indicates the placement of the cell-seeded support matrix 492 across the delivery tip 544. In some embodiments, the delivery tip 544 may further comprise a cylindrical portion 543 that is connected to the shuttle body 542 at the proximal end of the delivery tip 544; a tapered portion 545 that ends in a flat edge 549 at the distal end of the delivery tip 544; and an outline ledge 547 across the top and distal end of the delivery tip 544 that comprises an elliptical or oblong shape.

FIG. 48 illustrates a side view of a matrix shuttle device 540 with deployment wings 548 extended and a plunger 554 pressed to deliver a cell-seeded support matrix 492, according to aspects of the present embodiments. The arrow near the plunger 554 indicates pushing of the plunger 554 into the matrix shuttle device body 542. In some embodiments, the operator may use a thumb for pushing the plunger 554 and flat disc portion 556 while using one or more other fingers to pull on the finger grips 552. When the plunger 554 is pushed, in some embodiments it may cause the deployment wings 548 to extend out of the holes 550 at the distal end of the delivery tip 544. The extension of the deployment wings 548, in some embodiments, may push the cell-seeded support matrix 492 off the delivery tip 544.

Referring to FIG. 47 and FIG. 48, in some embodiments, the movements described above may allow the cell-seeded support matrix to be delivered to a surgical site as described in step 530 of the method 520, where the surgical site may be prepared by the method 330. The shape of tapered portion 545 at the distal end of the matrix shuttle device 540 allows surface area to be minimized to reduce the likelihood that the cell-seeded support matrix 492 will adhere to the matrix shuttle device 540, and possibly be damaged in the process of being delivered from the matrix shuttle device 540.

Figure 49:
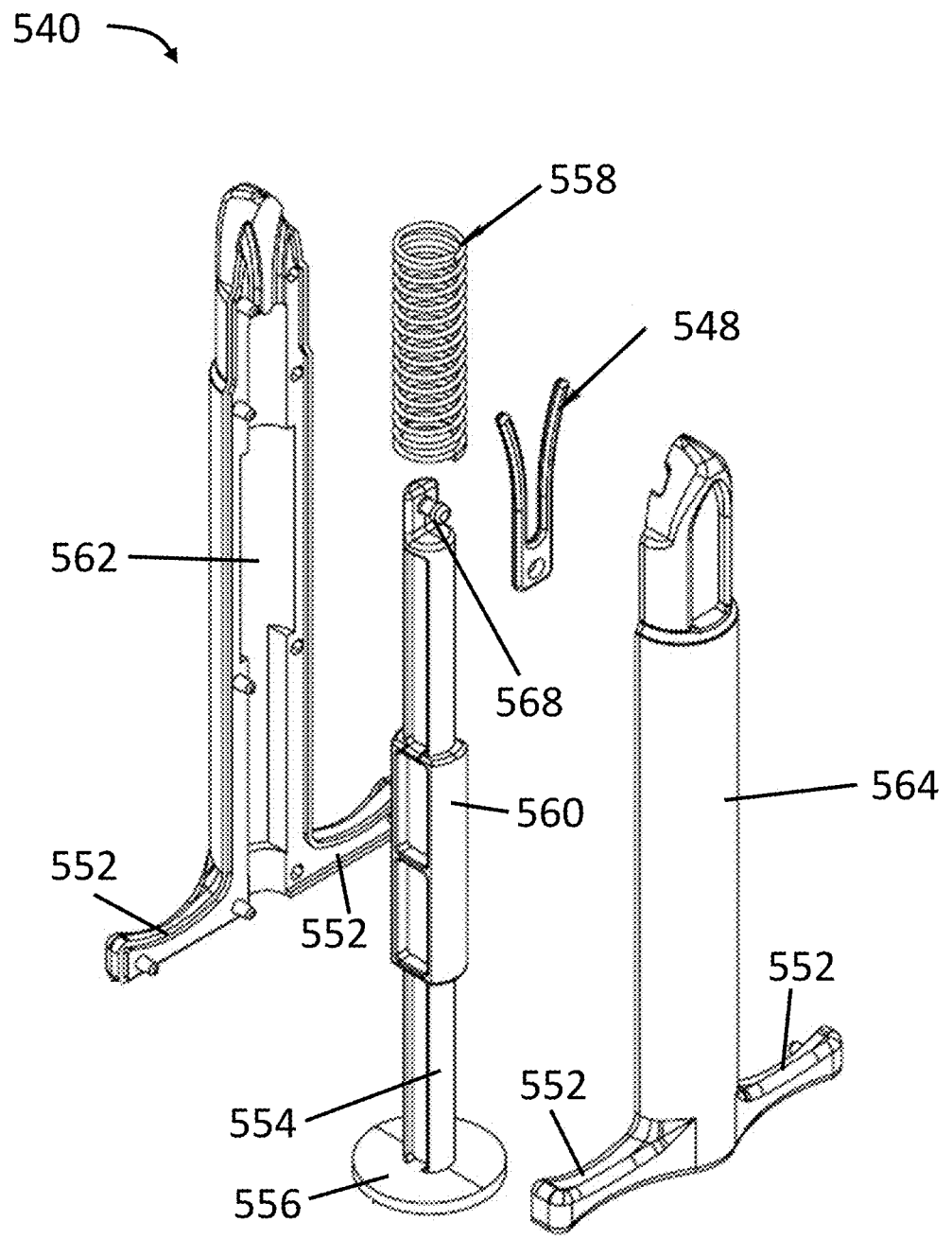
FIG. 49 illustrates a perspective exploded view of parts of a matrix shuttle delivery device according to aspects of the present embodiments.

FIG. 49 illustrates a perspective exploded view of parts of a matrix shuttle device 540 according to aspects of the present embodiments. In addition to the parts described above, in some embodiments the shuttle body may comprise two shells 562, 564. In some embodiments, the plunger 554 comprises: a cylindrical body 560; a flat disc portion 556 at the proximal end of the cylindrical body 560; and a recessed portion with protruding pin 568 at the proximal end of the cylindrical body 560. In some embodiments, the protruding pin 568 comprises a small cylinder disposed perpendicular to the longitudinal axis of the cylindrical body 560 and a rounded knob with a diameter larger than that of the small cylinder. In some embodiments, the protruding pin 568 with the rounded knob may be inserted into a circular hole 572 of the deployment wings 548 (shown in FIG. 50) in order to attach the deployment wings 548 to the plunger 554 such that the movement of the plunger may cause the deployment wings 548 to be actuated.

Referring still to FIG. 45 to FIG. 49, the matrix shuttle body 542 and plunger 554 may comprise or be composed of acrylonitrile butadiene styrene (ABS) or other polymeric or plastic material or equivalent.

Figure 50:
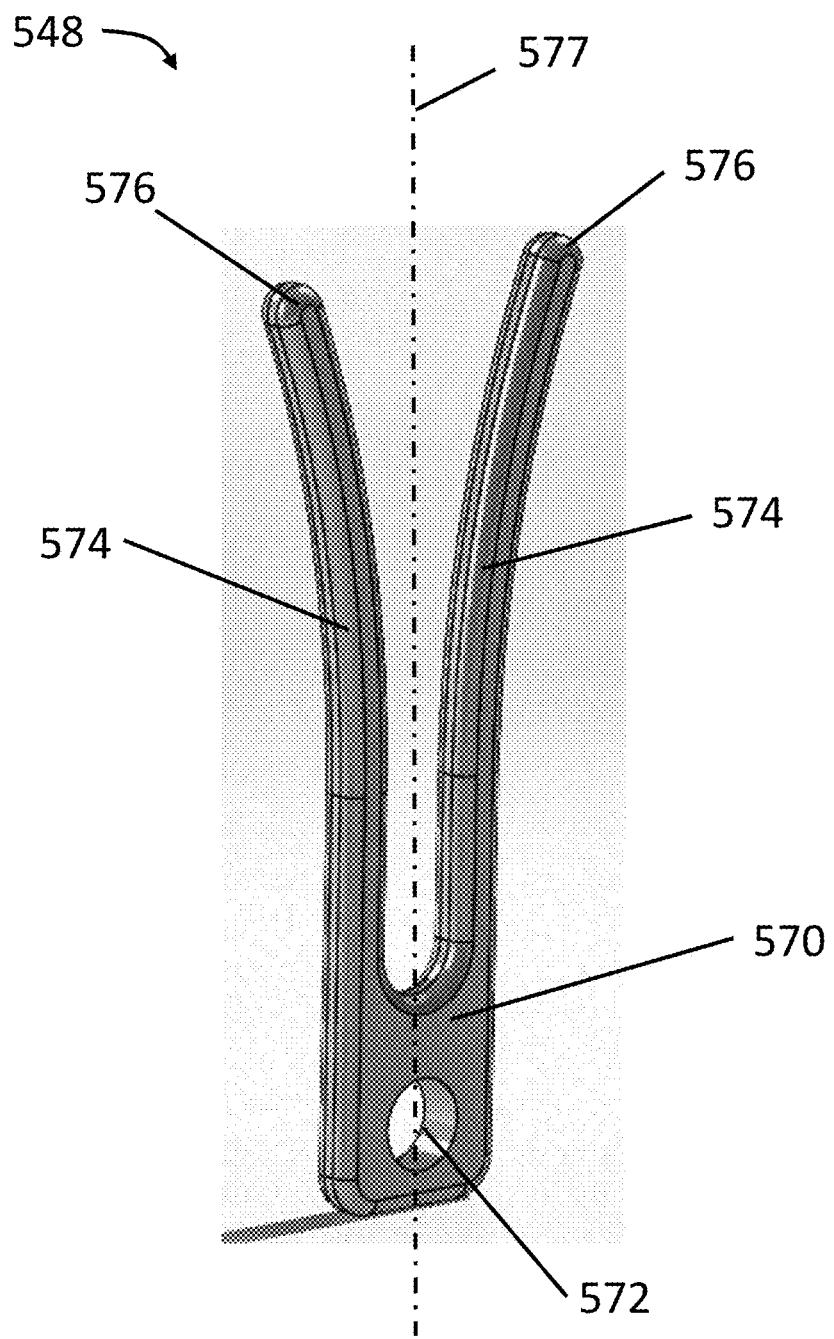
FIG. 50 illustrates a perspective view of deployment wings for use with a matrix shuttle delivery device, according to aspects of the present embodiments.

FIG. 50 illustrates a perspective view of deployment wings 548 for use with a matrix shuttle device 540, according to aspects of the present embodiments. In general, the deployment wings comprise a U-shaped body (570); at least two wing arms (574) comprising cylindrical rods that extend in parallel out of the U-shaped body (570) and curve outwards away from the U-shaped body (570); at least two rounded tips (576) at the distal ends of the at least two wing arms (574); and a circular hole at the proximal bottom of the U-shaped body (572). In some embodiments, the deployment wings 548 may comprise or be composed of silicone or ethylene propylene diene monomer (EPDM) rubber or other polymeric, plastic, or equivalent material. The two rounded tips 576 help to prevent damage to the cell-seeded support matrix 492 (and/or cells disposed thereon) when the two wing arms 574 are being deployed (or extended) to push the cell-seeded support matrix 492 off the matrix shuttle device 540.

As shown in FIGS. 49 and 50, each of the rounded tips 576 angles outwardly at an angle from about 1 to about 20 degrees (for example, about 5-10 degrees, about 3-20 degrees, about 5-18 degrees, about 6-12 degrees, about 15-20 degrees, about 10-15 degrees, about 2-6 degrees, about 3-30 degrees, between 1-45 degrees and other subranges therebetween) from a centerline 577 of the deployment wings 548. In some embodiments, when the deployment wings 548 are stored within the shuttle body, the rounded tips 576 are compressed radially inwardly by interior surfaces of the shells 562, 564. When the deployment wings 548 are deploy externally, inherent elasticity in the deployment wings 548 pushes the rounded tips radially outwardly (for example, as shown by the arrows in FIG. 48) thereby pushing the support matrix 492 off the distal delivery tip portion 544 of the matrix shuttle delivery device 540. Stated otherwise, when the rounded tips 576 are not compressed inwardly by the interior surfaces of the shuttle device 540 (that is, when they are in a deployed position) they expand outwardly to their uncompressed shape (that is, the shape shown in FIG. 50). By pushing the plunger 554 distally, the rounded tips 576 are deployed both distally as well as radially outwardly, thereby facilitating release of the support matrix 492 from the tapered portion 545. In addition, the radially outward action of the rounded tips 576 (i.e., in addition to the distal movement of the rounded tips 576) helps to spread out the support matrix 492 prior to application at the target site.

Figure 51:
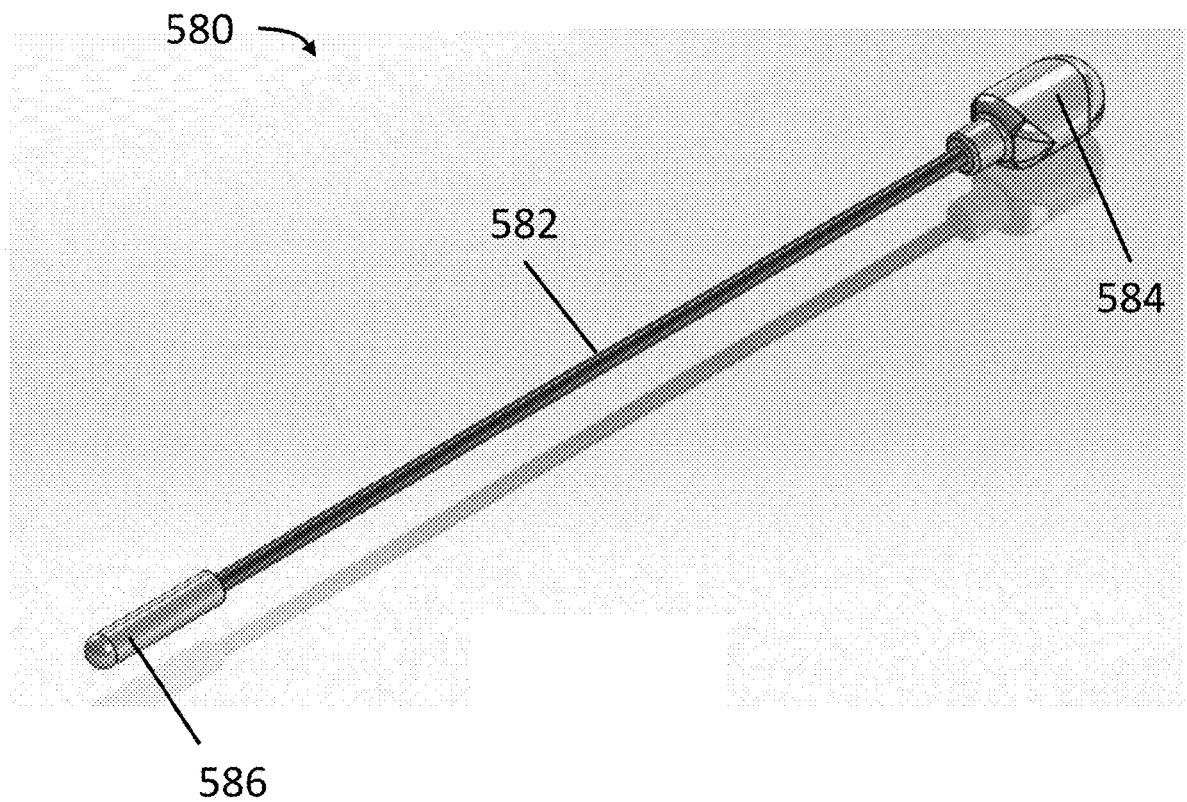
FIG. 51 illustrates a perspective view of an applicator tool, according to aspects of the present embodiments.

FIG. 51 illustrates a perspective view of an applicator tool 580, according to aspects of the present embodiments. In general, the applicator tool 580 may comprise a cylindrical rod 582; an applicator swab 584 attached by adhesive to one end of the cylindrical rod 582; and an applicator tip 586 attached by adhesive to another end of the cylindrical rod 582. In some embodiments, the applicator swab 584 may comprise cotton or polyurethane foam or other similar soft, absorbent material. In some embodiments, the applicator tip 586 may comprise soft silicone or other similar compliant material. In some embodiments, the cylindrical rod 582 may comprise a plastic material. In some embodiments, the adhesive may include Loctite 4011 glue.

Figure 52:
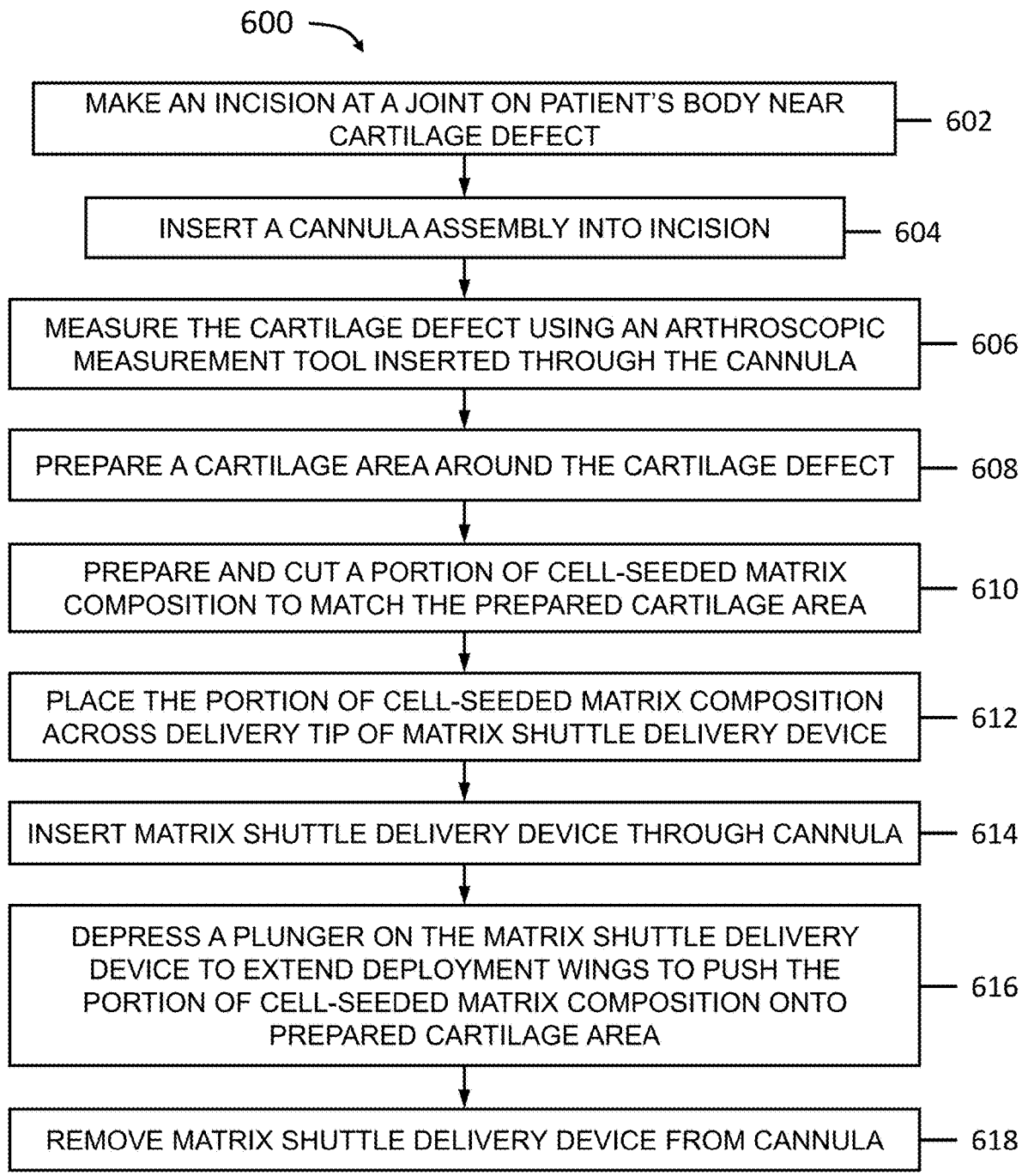
FIG. 52 illustrates a schematic of an arthroscopic surgical method to repair a cartilage defect, according to aspects of the present embodiments.

FIG. 52 illustrates a schematic of an arthroscopic surgical method 600 to repair a cartilage defect, according to aspects of the present embodiments. Generally, the method 600 may include making an incision at a joint on a patient's body near the cartilage defect (step 602); inserting a cannula assembly into the incision (step 604); measuring the cartilage defect at the joint using an arthroscopic measurement tool inserted through the cannula (step 606); preparing a cartilage area around the cartilage defect (step 608); preparing and cutting a portion of cell-seeded matrix composition using a matrix cutter tool to match the shape of the prepared cartilage area (step 610); placing the portion of cell-seeded matrix composition across a delivery tip of a matrix shuttle delivery device (step 612); inserting the matrix shuttle delivery device through the cannula (step 614); depressing a plunger on the matrix shuttle delivery device to extend at least two deployment wings from within the delivery tip to push the portion of cell-seeded matrix composition off the delivery tip and onto the prepared cartilage area (step 616); and removing the matrix shuttle delivery device from the cannula (step 618).

In some embodiments, step 608 may include defining a region of cartilage surrounding the cartilage defect using a first cutting tool; and scraping, cutting, debriding and/or removing cartilage using one or more additional surgical cutting tools within the region of cartilage defined by the first cutting tool. In some embodiments, the cell-seeded matrix composition of step 610 may include chondrocytes seeded on one side of a bioresorbable matrix. In some embodiments, in step 610 the side of the cell-seeded matrix composition with chondrocytes is facing away from the delivery tip of the matrix shuttle delivery device. In some embodiments, the method 600 may include additional steps of applying fibrin glue to the prepared cartilage prior to delivery of the cell-seeded matrix composition; applying fibrin glue around an edge of the cell-seeded matrix composition after the cell-seeded matrix composition is delivered to the prepared cartilage; removing the cannula from the incision; and surgically closing the incision.

In some embodiments, an instrument system may include cells seeded on a surface of a matrix. In some embodiments, cells may include allogeneic chondrocyte cells. In some embodiments, cells may include cells obtained from a non-human source.

In some embodiments, an instrument system may include one or more tools for measuring a cartilage defect, cutting cartilage and preparing a surgical site, cutting a cell-seeded support matrix, and delivering and implanting a cell-seeded support matrix. In some embodiments, an instrument system may include custom cutters (including for example articulated arthroscopic cutting tools, ring curettes, square curettes, and rake curettes), matrix cutters, a measurement tool, and/or cutting blocks. Additional tools and materials that a surgeon or user may use during surgical materials may include scissors, razor blades, scalpels, surgical mallets, and/or cutting needles.

In some embodiments, an instrument system may include a device that is or comprises a custom cannula assembly. In some embodiments, a custom cannula assembly provided in a kit may have an inner diameter in a range from about 15 mm to about 20 mm. The custom cannula assembly may comprise an obturator, a dam seal sub-assembly, and/or a cannula body.

In some embodiments, an instrument system may include one or more tools for securing an implanted composition in a surgical site. In some embodiments, tools for securing an implanted composition may include one or more probes. In some embodiments, tools for securing an implanted composition may include an applicator tool.

In some embodiments, additional materials and tools that a surgeon or user may use to perform the methods in this disclosure may include forceps, tweezers, Adson forceps, neurosurgical patties, sutures, sterile dishes, sterile flasks, sterile solutions, epinephrine, and/or sterile saline.

It will be appreciated by persons skilled in the art that numerous variations and/or modifications may be made to the invention shown in the specific embodiments without departing form the spirit and scope of the invention as broadly described.

All publications, patent applications, patents and other references mentioned herein are incorporated by reference in their entirety. In addition, the materials, methods and examples are illustrative only and not intended to be limiting. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described herein.

EXAMPLES

Example 1: Defect Preparation

The present example (Example 1) describes the preparation of a knee cartilage defect in surgical site to be treated using the technologies provided in the present disclosure. First, a surgical site may be flushed and washed with isotonic saline. A cartilage defect and the cartilage surrounding the defect may be assessed physically and visually via an arthroscopic device (e.g., arthroscopic camera) inserted into the first surgical site adjacent to the defect via a cannula 96 positioned in the site. Attention should be paid to discoloration, irregular surface areas, absence of normal resiliency, cartilage thinning, and/or unstable and undermined cartilage. After inspection, the size of the defect should be measured using an arthroscopic measurement probe 210, which is a tool with an extensible and rotatable ruler 218 at its distal end that is inserted into a cannula 96 disposed at the surgical site. The surgeon or operator should use the markings 232 on the ruler 218 to measure the dimensions of the defect in order to select the appropriate cutting tools in the next step.

After measurement of the defect, an area of the cartilage surrounding the defect may be outlined and sculpted using, for example, without limitation, a set of surgical cutting tools that are inserted into a cannula 92 in a second surgical site. The first tool is an articulated arthroscopic cutting tool 270 that has a curved oval blade 278 at the distal end. The size of the blade 278 should be selected based on the measurements so that the blade can completely surround the defect. The operator or surgeon may use a thumb slider 274 on the cutting tool 270 to adjust the tilt angle of the blade 278, and then press the blade into the cartilage to form a clear outline 52 in the cartilage.

Next, the defect should be debrided down to the subchondral bone and peripherally until vertical walls of healthy, stable cartilage 52 surrounds the defect site. The debriding may be done with a second, third, and/or fourth surgical cutting tool. These tools may include a ring curette 350, a square curette 400, and/or a rake curette 430. Each of these tools can be inserted through a cannula 92, have at least one surgically sharp cutting edge or blade mounted at the end of a shaft, and a handle that protrudes outside the cannula. These cutting tools may be manipulated by the user or operator to position the surgically sharp cutting edges at the defect site to cut or scrape away the cartilage. All damaged and fibrous tissue on the defect bed should be removed. Care should be taken such that removal of healthy cartilage is minimal outside the outline formed by the shape defined by the articulated arthroscopic cutting tool 270. Care should also be taken to avoid penetrating the subchondral bone. The resulting exposed region of subchondral bone 54 and surrounding stable cartilage 42 may form a clearly defined shape 52, such as an oval, that matches the shape of the curved blade of the articulated arthroscopic cutting tool. A knee joint may be drained of fluid through an incision or via suction, in preparation for the delivery of an implant to a defect in a surgical site. Excess fluid around the defect can also be dried using kitners ("peanuts"), in effect wicking excess fluid away from the cartilage defect. For punctate bleeding from the subchondral bone, hemostasis may be achieved by pressure with diluted epinephrine-soaked neurosurgical patties (e.g., 1 cc of 1:1000 Epinephrine diluted with 20 cc of sterile saline, etc.) or by applying fibrin sealant at the point of bleeding.

Example 2: Preparation of Cell-Seeded Support Matrix

The cell-seeded support matrix should be prepared prior to delivery and implantation at the surgical site by cutting it to an appropriate size and shape. In the above Example 1, a defect site was prepared by forming a clearly defined shape 52 of an exposed region of subchondral bone with surrounding stable cartilage. The next step is to prepare a portion of cell-seeded support matrix that matches the shape of the prepared defect site so that it may be delivered to cover the subchondral bone with minimal gaps or overlaps. A matrix cutter 500 with a dimension and shape that matches the prepared site may be chosen. A piece of cell-seeded support matrix 482 may be placed on a cutting mat 480 with the cells facing upward. The cutting mat may 480 comprise a soft or compliant material such as silicone or rubber. The cells should be facing upward and contact with the cell-seeded surface should be minimized to avoid damage to the cells. The matrix cutter 500 is then placed with blade side 510 facing downward onto the cell-seeded support matrix 482. Downward force is then applied to the top surface 506 of the matrix cutter 500 using at least one of a hand, a hammer, a mallet 486, and/or other tool by the user or operator. The downward force causes the blade 510 of the matrix cutter 500 to cut into the cell-seeded support matrix 482 in a manner similar to a cookie cutter cutting a cookie out of a sheet of dough. The matrix cutter 500 is then removed, and a portion of the cell-seeded support matrix cut to the same shape 492 as the matrix cutter 500 is available to be retrieved by tweezers 490 and/or other handling tool. Handling of the cell-seeded support matrix should be primarily be at the cut edges to minimize damage to the cells.

Example 3: Delivery of Cell-Seeded Support Matrix Using Matrix Shuttle Delivery Device Following the preparation of the cell-seeded support matrix 492 using the matrix cutter tool 500 presented in Example 2 by cutting it using a matrix cutter 500, the cell-seeded support matrix 492 may be delivered to the surgical defect site prepared in Example 1. The user or operator may pick up the prepared cell-seeded support matrix 492 using tweezers to gently grip one or more edges of the cell-seeded support matrix 492, taking care to minimize contact with the interior of the matrix and to handle the matrix gently, in order to minimize damage to the cells. The cell-seeded support matrix 492 may then be carefully placed across a distal delivery tip portion 544 of a matrix shuttle delivery device 540, with the cell-seeded side facing upward. The delivery tip portion 544 has an outline 547 imprinted as a depression so that it accommodates the shape and size of the prepared cell-seeded support matrix. Different sizes of matrix shuttle delivery devices are available to match different sizes of cell-seeded support matrix pieces. The delivery tip portion also has a narrow flat tip region 549 at its furthest distal end in order to minimize the contact area between the device and the cell-seeded support matrix 492. The cell-seeded support matrix 492 remains in contact with the matrix shuttle delivery device 540 by capillary forces due to moisture between the shuttle and the matrix, and no further mechanism for attachment is needed.

The matrix shuttle delivery device 540 with cell-seeded support matrix 492 placed on the delivery tip 544 is then inserted into a cannula 92 at a surgical site. The user or operator should then position the delivery tip 544 by moving and rotating the matrix shuttle delivery device 540 such that the cell-seeded support matrix 492 closely aligns with the prepared defect site 52. A plunger 556 on the matrix shuttle delivery device 540 is then pushed by the user or operator into the body of the matrix shuttle delivery device 540, while using the finger grips to provide opposing force. Upon pushing of the plunger 556, at least two deployment wings 548 within the delivery tip 544 protrude outward from at least two holes 550 and push against the bottom cell-less side of the cell-seeded support matrix 492. The tips 576 of the deployment wings 548 are rounded and small in radius in order to minimize contact area with the cell-seeded support matrix 492. The cell-seeded support matrix 492 is then pushed off the delivery tip 544 of the matrix shuttle delivery device 540 and onto the prepared defect site 52. The cell-seeded side of the matrix should be in contact with the exposed subchondral bone at the prepared defect site. The user or operator may use an applicator tool 580 to gently reposition the cell-seeded support matrix 492 so that it is well aligned within the prepared defect site 52.

Example 4: Securing a Cell-Seeded Support Matrix in a Cartilage Defect

The present example (Example 4) describes a method for securing a cell-seeded support matrix 492 in a defect in a surgical site. A cell-seeded support matrix 492 may be secured using a fibrin glue fixation step that may be performed following arthroscopic delivery of a cell-seeded support matrix 492 to a defect in a patient. After the cell-seeded support matrix 492 is inserted into the defect, with the cell-seeded side of the implant facing the defect, fibrin sealant (such as Tisseel®, fibrin based adhesive available from Baxter, Austria) may be applied to the rim (i.e., periphery) of the implant. Light pressure may then be applied using an applicator tool 580 or another tool.

The security of the implant should be tested by fully flexing and extending the knee several times, and then inspecting the implant to ensure that it has remained in place. The joint may than be irrigated in order to remove any remaining free particles of bone or cartilage in the site. Care should be taken to ensure that the implant is protected and not dislodged during irrigation. The wound may then be closed using standard techniques known to those skilled in the art.

In general, the Examples above describe how an arthroscopic surgery at a knee joint may be performed to repair a cartilage defect using the present embodiments. The defect site is measured using an arthroscopic measurement tool 210. An appropriately sized cutting tool 270 is selected and used to cut an outline around the defect. The defect site is prepared using one or more surgical cutting tools to remove damaged cartilage and form a well-defined region 52 of exposed subchondral bone surrounded by healthy cartilage. A portion of cell-seeded support matrix 492 is prepared by cutting it with a matrix cutter 500 to match the size and shape of the prepared defect site 52. The cell-seeded support matrix 492 is delivered to the defect site using a matrix delivery shuttle device 540 to minimize contacting or damaging the cells. The cell-seeded support matrix 492 is then secured using fibrin glue, the joint is cleaned and irrigated, and the wound site is closed.

Example 5: Cell Viability Bench Testing

In the present Example (Example 5), the delivery methods described in Examples 3, 4, and 5 are compared on the basis of their impact to cell number and viability following simulated delivery to a defect in a surgical site in knee joint tissue. The present experiments were performed using a human cadaver knee model. Positive controls include a condition in which a cell-seeded matrix was not delivered to a site by any method, as well as a condition in which a cell-seeded matrix was delivered to a site using a traditional open surgical technique.

Delivery of the cell-seeded support matrix implants via the methods, tools, and devices in the present disclosure yielded the unexpected and surprising results of improved cell numbers and cell viability values compared to traditional surgical methods, measured qualitatively.

As a qualitative visual measure of cell viability, cell metabolic activity was determined by staining cells on a matrix with 3-(4,5-dimethylthiazol-2-yl)-2,5-diphenyltetrazolium bromide (MTT), and visually examining cells positive for insoluble formazan, a dark-colored conversion product that marks actively respiring cells. Compared to the other methods tested, matrices delivered using the current methods and tools retained the highest number of metabolically active cells, approaching that of undelivered positive control matrices. The MTT assays also showed the importance of minimizing contact and handling of the cell-seeded support matrices in order to achieve the highest cell viabilities across the cell-seeded support matrices.

Conventional methods for implanting MACI (and/or cell-seeded support matrices 492) have resulted in cell viability below 4% using arthroscopic methods, and cell viability below 40% using open techniques. (See Biant et al. (Biant, L. C., Simons, M., Gillespie, T. and McNicholas, M. J., 2017. Cell viability in arthroscopic versus open autologous chondrocyte implantation. *The American Journal of Sports Medicine*, 45(1), pp. 77-81.)).

Table 1 includes bench testing results using the devices and methodologies described herein. The table includes a summary of minimum cell number (MCN) and cell viability results from various exemplary steps including delivery of the cell-seeded matrix 492 via the shuttle delivery device 540, manipulation of the cell-seeded matrix 492 with a silicone tip 586 (also shown in some embodiments as an applicator tip), and manipulation of the cell-seeded matrix 492 with a spongy tip 584 (also shown in some embodiments as an applicator swab). The MCN and cell viability were also reported for control experiments, applying thumb pressure to the cell-seeded matrix 492 at various pressures (for example, from about 370 grams to about 1635 grams) for 30 seconds. In each case, both the minimum cell number (MCN, as measured in relative fluorescence units, RFU) as well as the cell viability (measured in percent and assessed as an overall average) met the relevant acceptance criteria (i.e., greater than 5000 RFU and greater than or equal to 80% cell viability, respectively). It should be noted that the cell viability values were all within a range between 94% and 99%.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

What is claimed is:

1. A matrix shuttle delivery device, comprising:
   a shuttle body, wherein the shuttle body comprises a substantially hollow cylinder;
   a delivery tip at a distal end of the shuttle body;
   a plunger disposed longitudinally within the shuttle body and protruding out of a proximal end of the shuttle body;
   at least two deployment wings disposed inside the delivery tip and attached to the plunger; and
   at least two holes on a distal surface of the delivery tip;
   wherein pushing the plunger longitudinally into the shuttle body causes the at least two deployment wings to extend externally through the at least two holes of the delivery tip.

2. The matrix shuttle delivery device of claim 1, wherein the matrix shuttle device further comprises a spring disposed longitudinally inside the shuttle body and attached to the plunger.

3. The matrix shuttle delivery device of claim 2, wherein the spring causes the at least two deployment wings to retract inside the at least two holes when the plunger is released.

4. The matrix shuttle delivery device of claim 1, wherein the matrix shuttle device further comprises one or more finger grips disposed at the proximal end of the shuttle body.

5. The matrix shuttle delivery device of claim 4, wherein the one or more finger grips each comprise a rod that is connected at one end to an exterior surface of the shuttle body and extends radially outward away from the shuttle body, wherein the distal side of each rod is curved to accommodate a user's finger.

6. The matrix shuttle delivery device of claim 4, wherein the shuttle body, delivery tip, and finger grips are formed as two continuous, identical shells that come together to form the matrix shuttle delivery device.

TABLE 1

| Bench Testing Results | | |
|---|---|---|
| Test Condition | MCN (RFU) | Viability (%) |
| Control | 21762.9 | 98.7% |
| Thumb Pressure (30 sec) | 21652.5 | 98.4% |
| Shuttle Delivery Device | 16202.3 | 96.8% |
| Manipulation with Silicone Tip | 29537.1 | 96.1% |
| Manipulation with Spongy Tip | 26451.4 | 94.4% |
| Acceptance Criteria: | >5000 | ≥80% |

7. The matrix shuttle delivery device of claim 1, wherein the delivery tip comprises:
- a cylindrical portion that is connected to the shuttle body at the proximal end of the delivery tip;
- a tapered portion comprising two sloped sides that come together in a flat surface at the distal end of the delivery tip; and
- an outline ledge around the distal end of the delivery tip that comprises an elliptical or oblong shape,
- wherein a centerline of the outline ledge is substantially parallel to the flat surface at the distal end of the delivery tip.

8. The matrix shuttle delivery device of claim 7, wherein the at least two holes are each positioned on the two sloped sides of the delivery tip, so that when the deployment wings are extended, a line connecting the rounded tips of the deployment wings is substantially perpendicular to the flat surface at the distal end of the delivery tip.

9. The matrix shuttle delivery device of claim 1, wherein the at least two holes each comprise a diameter that is larger than a diameter of each of the at least two deployment wings.

10. The matrix shuttle delivery device of claim 1, wherein the deployment wings comprise:
- a U-shaped body;
- at least two wing arms comprising cylindrical rods that extend in parallel out of the U-shaped body and curve outwards away from the U-shaped body;
- at least two rounded tips at the distal ends of the at least two wing arms; and
- a circular hole at the proximal bottom of the U-shaped body.

11. The matrix shuttle delivery device of claim 10, wherein the plunger comprises:
- a cylindrical body;
- a flat disc portion at the proximal end of the cylindrical body; and
- a recessed portion with a protruding pin at the proximal end of the cylindrical body,
- wherein the protruding pin comprises a small cylinder disposed perpendicular to the longitudinal axis of the cylindrical body and a rounded knob with a diameter larger than that of the small cylinder.

12. The matrix shuttle delivery device of claim 11, wherein the protruding pin of the plunger passes through the circular hole at the proximal bottom of the U-shaped body of the deployment wings.

13. The matrix shuttle delivery device of claim 1, wherein the deployment wings comprise at least one member of the group consisting of silicone, ethylene propylene diene monomer (EPDM) rubber, plastic, and a flexible polymeric material.

14. The matrix shuttle delivery device of claim 1, wherein the plunger and shuttle body comprise at least one of acrylonitrile butadiene styrene (ABS) or plastic.

15. A matrix shuttle delivery device, comprising:
- a shuttle body, wherein the shuttle body comprises a substantially a hollow cylinder;
- a delivery tip at the distal end of the shuttle body, comprising:
  - a cylindrical portion that is connected to the shuttle body at the proximal end of the delivery tip;
  - a tapered portion comprising two sloped sides that come together in a flat surface at the distal end of the delivery tip; and
  - an outline ledge across the top and distal end of the delivery tip that comprises an elliptical or oblong shape;
- a plunger disposed longitudinally within the shuttle body and protruding out of the proximal end of the shuttle body, the plunger comprising:
  - a cylindrical body;
  - a flat disc portion at the proximal end of the cylindrical body; and
  - a recessed portion with protruding pin at the proximal end of the cylindrical body,
  - wherein the protruding pin comprises a small cylinder disposed perpendicular to the longitudinal axis of the cylindrical body and a rounded knob with a diameter larger than that of the small cylinder.

16. The matrix shuttle delivery device of claim 15, further comprising:
- at least two deployment wings disposed inside the delivery tip and attached to the plunger, the deployment wings comprising:
  - a U-shaped body;
  - at least two wing arms comprising cylindrical rods that extend in parallel out of the U-shaped body and curve outwards away from the U-shaped body;
  - at least two rounded tips at the distal ends of the at least two wing arms; and
  - a circular hole at the proximal bottom of the U-shaped body; and
- one or more finger grips disposed at the proximal end of the shuttle body,
the device further comprising:
- at least two holes, each hole positioned on one of the two sloped sides of the delivery tip; and
- a spring disposed longitudinally inside the shuttle body and attached to the plunger,
- wherein pushing the plunger longitudinally into the shuttle body causes the at least two deployment wings to exit the at least two holes of the delivery tip, and
- wherein the spring causes the at least two deployment wings to retract inside the at least two holes when the plunger is released.

* * * * *